US009493420B2

(12) United States Patent
Peyton et al.

(10) Patent No.: US 9,493,420 B2
(45) Date of Patent: Nov. 15, 2016

(54) QUINOLINE DERIVATIVES AND USES THEREOF

(71) Applicants: David H. Peyton, Portland, OR (US); Steven Burgess, Tualatin, OR (US)

(72) Inventors: David H. Peyton, Portland, OR (US); Steven Burgess, Tualatin, OR (US)

(73) Assignee: Portland State University, Portland, OR (US)

( * ) Notice: Subject to any disclaimer, the term of this patent is extended or adjusted under 35 U.S.C. 154(b) by 319 days.

(21) Appl. No.: 13/951,340

(22) Filed: Jul. 25, 2013

(65) Prior Publication Data

US 2013/0310348 A1 Nov. 21, 2013

Related U.S. Application Data

(62) Division of application No. 13/093,261, filed on Apr. 25, 2011, now Pat. No. 8,524,739, which is a division of application No. 11/884,547, filed as application No. PCT/US2005/044978 on Dec. 12, 2005, now Pat. No. 7,968,539.

(60) Provisional application No. 60/654,207, filed on Feb. 17, 2005.

(51) Int. Cl.
*C07D 215/46* (2006.01)
*A61K 31/551* (2006.01)
*C07D 215/44* (2006.01)
*C07D 401/12* (2006.01)
*C07D 401/14* (2006.01)
*C07D 405/14* (2006.01)
*C07D 409/12* (2006.01)
*C07D 417/12* (2006.01)
*C07D 471/04* (2006.01)
*A61K 31/4706* (2006.01)
*A61K 31/4709* (2006.01)
*A61K 31/496* (2006.01)
*A61K 31/5415* (2006.01)
*A61K 31/55* (2006.01)
*A61K 45/06* (2006.01)
*C07D 405/12* (2006.01)
*C07D 409/14* (2006.01)
*C07D 417/14* (2006.01)

(52) U.S. Cl.
CPC ......... *C07D 215/46* (2013.01); *A61K 31/4706* (2013.01); *A61K 31/4709* (2013.01); *A61K 31/496* (2013.01); *A61K 31/5415* (2013.01); *A61K 31/55* (2013.01); *A61K 31/551* (2013.01); *A61K 45/06* (2013.01); *C07D 215/44* (2013.01); *C07D 401/12* (2013.01); *C07D 401/14* (2013.01); *C07D 405/12* (2013.01); *C07D 405/14* (2013.01); *C07D 409/12* (2013.01); *C07D 409/14* (2013.01); *C07D 417/12* (2013.01); *C07D 417/14* (2013.01); *C07D 471/04* (2013.01)

(58) Field of Classification Search
None
See application file for complete search history.

(56) References Cited

U.S. PATENT DOCUMENTS

| 5,510,356 A | 4/1996 | Vennerstrom |
| 5,596,002 A | 1/1997 | Hofheinz et al. |
| 6,166,015 A | 12/2000 | Rogers et al. |
| 7,968,539 B2 | 6/2011 | Peyton et al. |

FOREIGN PATENT DOCUMENTS

| EP | 0 326 331 A2 | 8/1989 |
| EP | 363212 | 4/1990 |
| EP | 0 876 346 B1 | 7/2001 |
| WO | WO 96/40138 | 12/1996 |
| WO | WO 2004/099179 A1 | 11/2004 |
| WO | PCT/US2005/044978 | 8/2006 |

OTHER PUBLICATIONS

Atteke et al., "In Vitro susceptibility to a new antimalarial organometallic analogue, ferroquine, of *Plasmodium falciparum* isolates from the Haut-Ogooué region of Gabon," *Journal of Antimicrobial Chemotherapy* 51:1021-1024, 2003.
Bhattacharjee et al., "A 3D QSAR Pharmacophore Model and Quantum Chemical Structure—Activity Analysis of Chloroquine(CQ)-Resistance Reversal," *J. Chem. Inf. Comput. Sci.* 42:1212-1220, 2002.
Burgess et al., "A Chloroquine-like Molecule Designed to Reverse Resistance in *Plasmodium falciparum*," *Journal of Medicinal Chemistry*, 49, pp. 5623-5625, 2006.
Chen et al., "Structure-Based Design of Potent Inhibitors of Scytalone Dehydratase: Displacement of a Water Molecule from the Active Site," *Biochemistry* 37:17735-17744, 1998.
Ciach et al., "Reversal of Mefloquine and Quinine Resistance in *Plasmodium falciparum* with NP30," *Antimicrobial Agents and Chemotherapy* 47(8):2393-2396, 2003.
Crandall et al., "Nonylphenolethoxylates as Malarial Chloroquine Resistance Reversal Agents," *Antimicrobial Agents and Chemotherapy* 44(9):2431-2434, 2000.
International Preliminary Report on Patentability, dated Aug. 21, 2007, issued by the International Searching Authority/US for related PCT Patent Application No. PCT/US2005/044978, filed Dec. 12, 2005, 5 pp.

(Continued)

*Primary Examiner* — Noble Jarrell
(74) *Attorney, Agent, or Firm* — Klarquist Sparkman, LLP

(57) ABSTRACT

This disclosure provides a new class of compounds referred to as "reversed chloroquines" (RCQs), which are highly effective against $CQ^R$ and $CQ^S$ malaria parasites. RCQs are hybrid molecules, which include an antimalarial quinoline analog (such as chloroquine) moiety and a $CQ^R$ reversal moiety. Exemplary RCQ chemical structures are provided. Also provided are pharmaceutical compositions including the disclosed RCQ compounds, and methods of using such compounds and compositions for the treatment of malaria and inhibition of $CQ^R$ or $CQ^S$ *Plasmodium* sp. (such as *P. falciparum*).

29 Claims, 4 Drawing Sheets

(56) References Cited

OTHER PUBLICATIONS

International Search Report and Written Opinion, dated Sep. 21, 2006, issued by the International Searching Authority/US for related PCT Patent Application No. PCT/US2005/044978, filed Dec. 12, 2005, 2 pp.

Madrid et al., "Parallel Synthesis and Antimalarial Screening of a 4-Aminoquinoline Library," *J. Comb. Chem.* 6:437-442, 2004.

"Malaria-Symptoms, Treatment, and Prevention," Health Encyclopedia—Diseases and Conditions, http://www.healthscout.com/ency/68/347/main.html#PreventionofMalaria, 5 pp., accessed Aug. 6, 2010.

Menezes et al., "In Vitro Chloroquine Resistance Modulation Study on Fresh Isolates of Brazilian *Plasmodium falciparum*: Intrinsic Antimalarial Activity of Phenotiazine Drugs," *Mem Inst Oswaldo Cruz*, Rio de Janeiro 97(7):1033-1039, 2002.

Oduola et al., "In Vitro and In Vivo Reversal of Chloroquine Resistance in *Plasmodium falciparum* with Promethazine," *Am. J Trop. Med. Hyg.* 58(5):625-629, 1998.

O'Neill, "Isoquine and Related Amodiaquine Analogues: A New Generation of Improved 4-Aminoquinoline Antimalarials," *Journal of Medicinal Chemistry*, 2003, 46, 4933-45.

Pradines et al., "In Vitro Reversal of Chloroquine Resistance in *Plasmodium falciparum* with Dihydroethanoanthracene Derivatives," *Am. J. Trop. Med. Hyg.* 66(6):661-666, 2002.

Stocks, "Novel Short Chain Chloroquine Analogues Retain Activity Against Chloroquine Resistant K1 *Plasmodium falciparum*," *Journal of Medicinal Chemistry*, 2002, 45, 4975-83.

Wermuth, "Molecular Variations Based on Isosteric Replacements," *The Practice of Medicinal Chemistry*, pp. 203-237, 1996.

QUINOLINE DERIVATIVES AND USES THEREOF

CROSS REFERENCE TO RELATED APPLICATIONS

This is a division of U.S. application Ser. No. 13/093,261, filed Apr. 25, 2011, now issued as U.S. Pat. No. 8,524,739, which is a division of U.S. application Ser. No. 11/884,547, filed Aug. 16, 2007, now issued as U.S. Pat. No. 7,968,539, which was the National Stage of International Application No. PCT/US2005/044978, filed Dec. 12, 2005, which claims the benefit of U.S. Provisional Application No. 60/654,207, filed Feb. 17, 2005, all of which are incorporated herein by reference in their entirety.

STATEMENT OF GOVERNMENT SUPPORT

This invention was made with United States government support pursuant to Grant No. AI051509-01A2 from the National Institutes of Health; the United States Government has certain rights in the invention.

FIELD OF THE DISCLOSURE

This disclosure relates to quinoline derivatives (such as chloroquine derivatives) useful in the treatment of chloroquine-resistant ($CQ^R$) and chloroquine-sensitive ($CQ^S$) malaria parasites.

BACKGROUND

Malaria is a disease caused by various species of hemosporidian blood parasites of the genus *Plasmodium* (including *P. falciparium*, *P. vivax*, *P. ovale*, and *P. malariae*). The human disease process begins with the bite of an infected female *Anopheline* mosquito. *Plasmodium* sp. sporozoites released from the salivary glands of the mosquito enter the bloodstream and quickly (within about 30 minutes) invade liver cells (hepatocytes). The liver-stage parasites differentiate and undergo asexual multiplication resulting in tens of thousands of merozoites which burst from the hepatoctye. Merozoites then invade red blood cells (erythrocytes) where they undergo an additional round of multiplication. The clinical signs of malaria, fever and chills, are associated with the synchronous rupture of infected erythrocytes.

Malaria is a worldwide public health problem. Up to 3 million people die of malaria each year, and the total number of people infected with malaria worldwide approaches half a billion. The impact of this disease, in terms of suffering and economics, is huge. In the past, the inexpensive and orally administered antimalarial drug, chloroquine (CQ), was the "gold standard" treatment.

During its blood stage, the malaria parasite metabolizes (in its digestive vacuole (DV)) hemoglobin present in erythrocytes. A by-product of this metabolic process is heme, which would be toxic to the parasite except for heme detoxification mechanisms developed by the organism. CQ is believed to inhibit heme detoxification in the DV by binding to heme and/or to hemozoin (Ginsburg et al., *Parasitol. Today*, 15:357, 1999; Chong and Sullivan, *Biochem. Pharmacol.*, 66(11):2201-2212, 2003; Leed et al., *Biochem.*, 41(32):10245-10255, 2002; Egan et al., *Biochem.*, 40(1):204-213, 2001; Raynes, *Int. J. Parasitol.*, 29(3):367-379, 1999; Egan et al., *J. Med. Chem.*, 43(2):283-291, 2000). This binding, in part, is thought to drive the thermodynamics that concentrates CQ in the parasite DV. Chloroquine-dependent heme accumulation in the DV may inhibit or kill the parasites.

Unfortunately, certain *Plasmodium* sp. strains have evolved resistance to CQ. In fact, the spread of chloroquine-resistant ($CQ^R$) *Plasmodium* sp. parasites has rendered CQ almost useless for malaria treatment. In addition, *Plasmodium* sp. resistance to other antimalarial drugs, such as artemisinin and its derivatives, has been reported (Xiao et al., *Parasitol. Res.*, 92(3):215-219, 2004). These are particularly devastating problems in many impoverished parts of the world where such drugs are most needed (Krogstad, *Epidemiol. Rev.*, 18(1):77-89, 1996).

*Plasmodium* sp. $CQ^R$ is correlated with mutations in the parasite's DV membrane transporter protein (PfCRT). PfCRT is thought to enhance CQ export from the DV (Zhang et al., *Biochem.*, 43(26):8290-8296, 2004; Bennett et al., *Mol. Biochem. Parasitol.*, 133(1):99-114, 2004; Martin and Kirk, *Mol. Biol. Evol.*, 21(10):1938-1949, 2004). A particularly well-studied PfCRT mutation is K76T, which is correlated with $CQ^R$ (Martin and Kirk, *Mol. Biol. Evol.*, 21(10): 1938-1949, 2004; Johnson et al., *Mol. Cell*, 15(6):867-877, 2004; Durrand et al., *Mol. Biochem. Parasitol.*, 136(2):273-285, 2004; Ranjit et al., *Trop. Med. Int. Health*, 9(8):857-861, 2004; Durand et al., *Antimicrob. Agents Chemother.*, 46(8):2684-2686, 2002; Durand et al., *Mol. Biochem. Parasitol.*, 114(1):95-102, 2001; Cooper et al., *Mol. Pharmacol.*, 61(1):35-42, 2002; Djimde et al., *N. Engl. J. Med.*, 344(4): 257-263, 2001).

Alternative therapies for treatment of chloroquine-resistant ($CQ^R$) malaria parasites have been developed, including combination therapies (Kumar et al., *Curr. Med. Chem.*, 10(13):1137-1150, 2003). However, none of these therapies meet CQ's simplicity of use and low cost.

One approach to treatment of $CQ^R$ parasites involves the use of chemicals known as "reversal agents." Reversal agents are chemicals that have been found to quash CQ resistance (Krogstad et al., *Science*, 238(4831):1283-1285, 1987; Martin et al., *Science*, 235(4791):899-901, 1987; Ryall, *Parasitol. Today*, 3(8):256, 1987); thus, making $CQ^R$ strains sensitive again to CQ. $CQ^R$ reversal agents do not appear to have independent therapeutic value against *Plasmodium* sp. because the therapeutically useful dose for CQ applied to a $CQ^S$ strain in the presence of a reversal agent is nearly the same as in the absence of the reversal agent.

At least some reversal agents are believed to act by inhibiting CQ export from the DV (Krogstad et al., *Science*, 238(4831):1283-1285, 1987; Martin et al., *Science*, 235 (4791):899-901, 1987). However, despite their effectiveness against $CQ^R$ *Plasmodium* sp. strains in vitro, therapeutically effective doses of many reversal agents would have to be quite high (with associated side effects) to reverse $CQ^R$ in vivo (van Schalkwyk et al., *Antimicrob. Agents Chemother.*, 45(11):3171-3174, 2001; Millet et al., *Antimicrob. Agents Chemother.*, 48(7):2753-2756, 2004).

New compositions and methods for the treatment of malaria, particularly for the treatment of $CQ^R$ malaria parasites, are needed.

SUMMARY OF THE DISCLOSURE

This disclosure concerns the discovery of a class of compounds referred to as "reversed chloroquines" (RCQs), which are highly effective against $CQ^R$ and $CQ^S$ malaria parasites. RCQs are hybrid molecules, which include an antimalarial quinoline analog (such as chloroquine) moiety and a $CQ^R$ reversal moiety. An antimalarial quinoline analog moiety of a RCQ is believed to inhibit the growth of *Plasmodium* sp. (the malaria pathogens), and a $CQ^R$ reversal moiety of a RCQ is believed to sensitize $CQ^R$ *Plasmodium* sp. strains to the RCQ inhibitory moiety. Without being limited to one theory, covalently linking these moieties may increase the local concentration of growth-inhibitory and/or $CQ^R$-reversal functionalities in the pathogen to effectively inhibit their growth and/or treat $CQ^R$ and $CQ^S$ malaria strains.

Exemplary RCQ chemical structures are provided throughout the disclosure. By way of example, such compounds are represented by the following general tripartite formula

Q-L-G including an antimalarial quinoline analog "Q" covalently linked via a linker "L" to a $CQ^R$ reversal moiety designated by the group "G":

Pharmaceutical compositions containing, and methods of using, the disclosed RCQs are also provided. For example, the disclosed RCQs are effective to treat malaria and/or inhibit the growth of $CQ^S$ and $CQ^R$ *Plasmodium* sp. strains.

The foregoing and other features and advantages will become more apparent from the following detailed description of several embodiments, which proceeds with reference to the accompanying figures.

BRIEF DESCRIPTION OF THE FIGURES

FIG. 3A shows dose response curves for CQ as applied to D6 (closed diamonds) and Dd2 (closed squares) strains. FIG. 3B shows dose response curves for RCQ_02 as applied to D6 (closed diamonds) and Dd2 (closed squares) strains. Y-axes in panels A and B are "Relative Fluorescence Units" (i.e., from 0 to 100; see, e.g., De et al., *J. Med. Chem.*, 41(25):4918-4926, 1998; De et al., *Am. J. Trop. Med. Hyg.*, 55(6):579-583, 1996; Smilkstein et al., *Antimicrob. Agents Chemother.*, 48(5):1803-1806, 2004). The x-axes in FIGS. 3A and 3B are log(concentration); hence negative numbers are expected. FIG. 3C is a bar graph consolidating the data from FIGS. 3A and 3B.

DETAILED DESCRIPTION

I. Introduction

Figure 1:
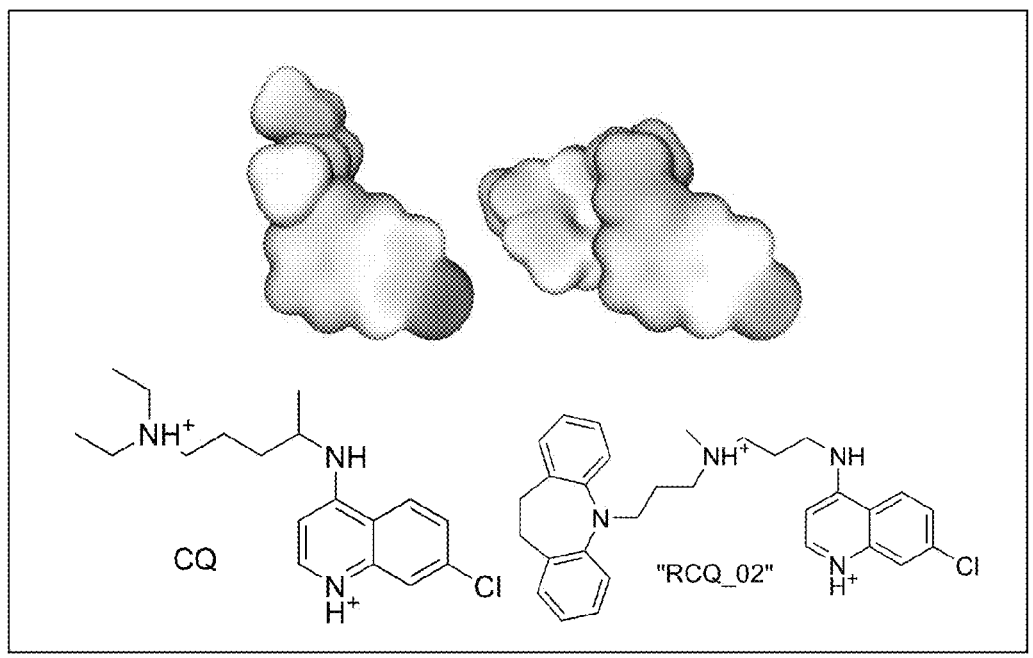
FIG. 1 shows electrostatic potential ranges (from negative (dark) to positive (light)) for chloroquine (top left) and RCQ_02 (top right) mapped onto a surface that is defined by a density of 0.002 of an electron (also referred to as a 0.002 density surface).

Disclosed herein are compounds that have been recently discovered that are highly effective against $CQ^R$ and $CQ^S$ malaria parasites. Such compounds may be used, at least, in pharmaceutical compositions, and to treat malaria and inhibit the growth of *Plasmodium* sp.

In certain examples, the compounds RCQ compounds include compounds of the general, tripartite formula

Q-L-G

Such disclosed compounds include a quinoline analog Q (such as a chloroquine derivative) covalently linked to a $CQ^R$ reversal moiety G via a linker L. In some examples, the $C_4$ dimethylamine side chain of chloroquine is covalently linked to the $CQ^R$ reversal moiety. In other examples, the $CQ^R$ reversal moiety is amitriptyline, amlodipine, azatadine, chlorpheniramine, citalopram, cyclosporine, cyproheptadine, cyproheptadine, desipramine, diethyl-{3-[3-(4-methoxy-benzylidene)-pyrrolidin-1-yl]-propyl}-amine, erythromycin, fantofarone, fluoxetine, haloperidol, icajine, imipramine, isoretuline, ivermectin, ketotefin, ketotifen, nomifensine, NP30: $C_9H_{19}$-Phenyl-(O—$CH_2CH_2$)$_{30}$OH, oxaprotiline, probenecid, progesterone, promethazine, strychnobrasiline, BG958, trifluoperazine, verapamil, or WR 268954.

In yet other embodiments, any of the foregoing or other disclosed compounds may be incorporated into pharmaceutical compositions that include a therapeutically effective amount of the compound or extract, and a pharmaceutically acceptable carrier. In some instances, a disclosed pharmaceutical composition further includes at least one additional antimalarial therapeutic agent (such as artesunate, mefloquine, sulfadoxine, or pyrimethamine, or combinations thereof).

The present disclosure also concerns methods of treating a subject for malaria or *Plasmodium* sp. infection by administering to the subject a therapeutically effective amount (such as from about 1 to about 50 mg/kg) of any of the compounds disclosed herein. In some cases, the compound is administered prophylactically. In other embodiments, the malarial pathogen is *P. falciparum*.

Also disclosed are methods for inhibiting the growth of *Plasmodium* sp. involving contacting at least one *Plasmodium* sp. parasite with a growth inhibitory amount (such as from about 1 to about 50 nM) of at least one disclosed compound. In some method embodiments, the *Plasmodium* sp. is *P. falciparum, P. vivax, P. ovale,* or *P. malariae,* or a combination thereof.

II. Abbreviations and Terms

CQ chloroquine
$CQ^R$ chloroquine resistant (or chloroquine resistance)
$CQ^S$ chloroquine sensitive
DV digestive vacuole
$IC_{50}$ concentration of an agent resulting in 50% inhibition of parasite growth
RCQ reversed chloroquine Unless otherwise noted, technical terms are used according to conventional usage. Definitions of common terms in chemistry terms may be found in *The McGraw-Hill Dictionary of Chemical Terms,* 1985, and The Condensed Chemical Dictionary, 1981. The singular terms "a," "an," and "the" include plural referents unless context clearly indicates otherwise. "Comprising" means "including"; hence, "comprising A or B" means "including A or B" or "including A and B."

In order to facilitate review of the various embodiments of the invention, the following explanations of specific terms are provided:

Acyl: A group of the formula RC(O)— wherein R is an organic group.

Aliphatic: An acyclic, straight- or branched-chain alkane, alkene, or alkyne, which, unless expressly stated otherwise, contains from one to twenty-five carbon atoms; for example, from one to fifteen, from one to ten, from one to six, or from one to four carbon atoms. The term "lower aliphatic" refers to an aliphatic group containing from one to ten carbon atoms. An aliphatic chain may be substituted or unsubstituted. Unless expressly referred to as an "unsubstituted aliphatic," an aliphatic groups can either be unsubstituted or substituted. An aliphatic group can be substituted with one or more substituents (up to two substituents for each methylene carbon in an aliphatic chain, or up to one substituent for each carbon of a —C=C— double bond in an aliphatic chain, or up to one substituent for a carbon of a terminal methine group). Exemplary aliphatic substituents include, for instance, amine, amide, sulfonamide, halogen, cyano, carboxy, hydroxy, mercapto, trifluoromethyl, alkyl, alkoxy, alkylthio, thioalkoxy, arylalkyl, heteroaryl, alkylamino, dialkylamino, or other functionality.

Alkenyl: An acyclic, straight- or branched-chain aliphatic radical containing at least two carbon atoms and having at least one carbon-carbon double bond; for example, containing from two to six carbon atoms, including (but not limited to) vinyl, 2-propenyl, 2-methyl-2-propenyl, 3-butenyl, 4-pentenyl, and 5-hexenyl.

Alkoxy: A radical (or substituent) having the structure —O—R, where R is a substituted or unsubstituted alkyl. Methoxy (—OCH$_3$) is an exemplary alkoxy group. In a substituted alkoxy, R is alkyl substituted with a non-interfering substituent. "Thioalkoxy" refers to —S—R, where R is substituted or unsubstituted alkyl. "Haloalkyloxy" means a radical —OR where R is a haloalkyl.

Alkyl: An acyclic, saturated, branched- or straight-chain hydrocarbon radical, which, unless expressly stated otherwise, contains from one to fifteen carbon atoms; for example, from one to ten, from one to six, or from one to four carbon atoms. This term includes, for example, groups such as methyl, ethyl, n-propyl, isopropyl, isobutyl, t-butyl, pentyl, heptyl, octyl, nonyl, decyl, or dodecyl. The term "lower alkyl" refers to an alkyl group containing from one to ten carbon atoms. Unless expressly referred to as an "unsubstituted alkyl," alkyl groups can either be unsubstituted or substituted. An alkyl group can be substituted with one or more substituents (for example, up to two substituents for each methylene carbon in an alkyl chain). Exemplary alkyl substituents include, for instance, amine, amide, sulfonamide, halogen, cyano, carboxy, hydroxy, mercapto, trifluoromethyl, alkyl, alkoxy (such as methoxy), alkylthio, thioalkoxy, arylalkyl, heteroaryl, alkylamino, dialkylamino, alkylsulfano, keto, or other functionality.

Alkylamino: An alkyl group where at least one hydrogen is substituted with an amino, mono-substituted amino or di-substituted amino group.

Amino: A chemical functionality —N(R)R' where R and R' are independently hydrogen, alkyl, heteroalkyl, haloalkyl, aliphatic, heteroaliphatic, aryl (such as optionally substituted phenyl or benzyl), heteroaryl, alkylsulfano, or other functionality. A "primary amino" group is —NH$_2$. "Monosubstituted amino" means a radical —N(H)R substituted as above and includes, e.g., methylamino, (1-methylethyl) amino, phenylamino, and the like. "Di-substituted amino" means a radical —N(R)R' substituted as above and includes, e.g., dimethylamino, methylethylamino, di(1-methylethyl) amino, and the like.

Analog: A molecule that differs in chemical structure from a parent compound, for example a homolog (differing by an increment in the chemical structure, such as a difference in the length of an alkyl chain), a molecular fragment, a structure that differs by one or more functional groups, or a change in ionization. Structural analogs are often found using quantitative structure activity relationships (QSAR), with techniques such as those disclosed in *Remington: The Science and Practice of Pharmacy,* 19th Edition, Chapter 28, 1995.

Animal: Living multi-cellular vertebrate organisms, a category that includes, for example, mammals and birds. The term mammal includes both human and non-human mammals. Similarly, the term "subject" includes all animals, including humans, simians, dogs, cats, horses, cows, rodents, etc. Likewise, the term "mammal" includes both human and non-human mammals.

Aralkyl: an aryl group (such as a phenyl group) appended to an alkyl radical including, but not limited to, benzyl, ethylbenzene, propylbenzene, butylbenzene, pentylbenzene, and the like. Conversely the term "phenylalkyl" refers to a phenyl group appended to an alkyl radical. Aralkyl groups, such as benzyl groups, may be unsubstituted or substituted with one, two or three substituents, with substituent(s) independently selected from alkyl, heteroalkyl, aliphatic, heteroaliphatic, thioalkoxy, haloalkyl (such as —CF$_3$), halo, nitro, cyano, —OR (where R is hydrogen or alkyl), —N(R)R' (where R and R' are independently of each other hydrogen or alkyl), —COOR (where R is hydrogen or alkyl) or —C(O)N(R')R" (where R' and R" are independently selected from hydrogen or alkyl). Non-limiting examples, include o-, m-, and/or p-chlorobenzyl, o-, m-, and/or p-methoxybenzyl, and o-, m-, and/or p-(trifluoromethyl) benzyl.

Aryl: The term aryl is used to refer to monocyclic and polycyclic aromatic ring systems. Certain examples of aryl groups include a non-aromatic ring fused with one or more aromatic rings. Aryl groups also may be optionally substituted independently with one or more substituents, such as one, two or three substituents per ring selected from alkyl, haloalkyl, alkylthio, heteroalkyl, aliphatic, heteroaliphatic, alkoxy, cycloalkyl, hydroxy, halo, cyano, nitro, optionally substituted phenyl, optionally substituted aralkyl (such as phenylalkyl), optionally substituted heteroaryl, optionally substituted heteroaralkyl, amino, monosubstituted amino, disubstituted amino, hydroxylamino, —OR (where R is hydrogen, haloalkyl, optionally substituted phenyl, optionally substituted phenylalkyl, optionally substituted heteroaryl or optionally substituted heteroaralkyl), —S(O)$_n$R (where n is an integer from 0 to 2 and R is alkyl, haloalkyl, optionally substituted phenyl, optionally substituted phenylalkyl, optionally substituted heteroaryl, optionally substituted heteroaralkyl, amino, monosubstituted or disubstituted amino), —N(R)C(O)R' (where R is hydrogen or alkyl and R' is hydrogen, alkyl, heteroalkyl, haloalkyl, optionally substituted phenyl, or monosubstituted or disubstituted amino), —N(R)SO$_2$R' (where R is hydrogen or alkyl and R' is alkyl, amino, monosubstituted or disubstituted amino), —C(O)R (where R is hydrogen, alkyl, haloalkyl, optionally substituted phenyl or optionally substituted heteroaryl), —COOR (where R is hydrogen, alkyl, optionally substituted phenyl, optionally substituted phenylalkyl, optionally substituted heteroaryl or optionally substituted heteroaralkyl), —C(O)N(R')R" (where R' and R" are independently selected from hydrogen, alkyl, haloalkyl, optionally substituted phenyl, optionally substituted phenylalkyl, optionally substituted heteroaryl or optionally substituted heteroaralkyl). In specific examples, the term aryl includes, for example, phenyl, benzyl, phenol, naphthyl, anthracenyl, phenanthrenyl, and substituted derivatives thereof.

Carbocycle: A saturated or unsaturated cyclic radical of 3 to 8 ring atoms in which each of the ring atoms are carbon. Such carbocyclic groups may be optionally substituted independently with one, two or three substituents selected from alkyl, heteroalkyl, haloalkyl, cycloalkyl, cycloalkylalkyl, aliphatic, heteroaliphatic, aryl, aralkyl, heteroaryl, heteroaralkyl, halo, cyano, acyl, acylamino, amino, monosubstituted amino, disubstituted amino, —COOR (where R is hydrogen or alkyl), —XR (where X is O or S(O)—, where n is an integer from 0 to 2, and R is hydrogen, alkyl, haloalkyl, cycloalkyl, aralkyl, aryl, heteroaryl or heteroaralkyl), or —C(O)N(R')R" (where R' and R" are independently selected from hydrogen or alkyl). Representative examples include, but are not limited to, cyclopentyl, cyclohexyl, cycloheptyl, cycloheptenyl, or cycloheptyl-2, 3, or 4-one, and the like.

Carbonyl: A radical of the formula —C(O)—. Carbonyl-containing groups include any substituent containing a carbon-oxygen double bond (C=O), including acyl groups, amides, carboxy groups, esters, ureas, carbamates, carbonates and ketones and aldehydes, such as substituents based on —COR or —RCHO where R is an aliphatic, heteroaliphatic, alkyl, heteroalkyl, hydroxyl, or a secondary, tertiary, or quaternary amine.

Carboxyl: A —COOH radical. Substituted carboxyl refers to —COOR where R is aliphatic, heteroaliphatic, alkyl, heteroalkyl, or a carboxylic acid or ester.

Cycloalkyl: A saturated monovalent cyclic hydrocarbon radical of three to seven ring carbons, e.g., cyclopentyl, cyclohexyl, cycloheptyl and the like.

Derivative: A chemical substance that differs from another chemical substance by one or more functional groups. Preferably, a derivative (such as a RCQ) retains a biological activity of a molecule from which it was derived (such as a quinoline analog, like chloroquine, or a $CQ^R$ reversal agent). In some cases, a derivative may be a hybrid of at least two otherwise separate chemical substances (such as a hybrid molecule containing a chloroquine moiety and a $CQ^R$ reversal moiety).

Haloalkyl: An alkyl group substituted with one or more same or different halo atoms, e.g., —CH$_2$Cl, —CF$_3$, —CH$_2$CF$_3$, —CF$_2$CF$_3$, —CH$_2$CCl$_3$, and the like.

Halogen: The elements fluorine, bromine, chlorine, and/or iodine. The term "halo" refers to fluoro, bromo, chloro and/or iodo substituents.

Heteroalkyl: An alkyl or cycloalkyl radical as defined above containing at least one heteroatom, such as N, O, S, or S(O)$_n$ (where n is 1 or 2).

Heteroaliphatic: An aliphatic group as defined above containing at least one heteroatom, such as N, O, S, or S(O)$_n$ (where n is 1 or 2).

Heteroaryl: A monovalent monocyclic or bicyclic aromatic radical of 5 to 10 ring atoms with each ring containing one, two, or three ring heteroatoms selected from N, O, or S, the remaining ring atoms being C. The aromatic radical is optionally fused to a phenyl or an optionally substituted heteroaryl ring or it is optionally substituted independently with one or more substituents, such as one or two substituents selected from alkyl, haloalkyl, heteroalkyl, aliphatic, heteroaliphatic, alkoxy, halo, cyano, nitro, aryl, optionally substituted heteroaryl, amino, monosubstituted amino, disubstituted amino, hydroxyamino, —OR (where R is hydrogen, haloalkyl, or optionally substituted phenyl), —S(O)$_n$R (where n is an integer from 0 to 2 and R is alkyl, haloalkyl, optionally substituted phenyl, amino, mono or disubstituted amino), —C(O)R (where R is hydrogen, alkyl, haloalkyl or optionally substituted phenyl), —COOR (where R is hydrogen, alkyl or optionally substituted phenyl), —C(O)N(R')R" (where R' and R" are independently selected from hydrogen, alkyl, haloalkyl, or optionally substituted phenyl). In specific examples, the term heteroaryl includes, but is not limited to pyridyl, pyrrolyl, thiophene, pyrazolyl, thiazolyl, imidazolyl, pyrimidinyl, thiadiazolyl, indolyl, carbazolyl, azaindolyl, benzofuranyl, benzimidazolyl, benzthiazolyl, quinoxalinyl, benzotriazolyl, benzisoxazolyl, purinyl, quinolinyl, isoquinolinyl, benzopyranyl, and derivatives thereof.

Heterocycle: A saturated or unsaturated cyclic radical of 3 to 8 ring atoms in which one or two ring atoms are heteroatomic groups selected from N, O, or S(O)$_n$ (where n is an integer from 0 to 2), the remaining ring atoms being C. The heterocyclic ring may be optionally substituted independently with one, two or three substituents selected from alkyl, heteroalkyl, haloalkyl, cycloalkyl, cycloalkylalkyl, aliphatic, heteroaliphatic, aryl, aralkyl, heteroaryl, heteroaralkyl, halo, cyano, acyl, acylamino, amino, monosubstituted amino, disubstituted amino, —COOR (where R is hydrogen or alkyl), —XR (where X is O or S(O)$_n$, where n is an integer from 0 to 2, and R is hydrogen, alkyl, haloalkyl, cycloalkyl, aralkyl, aryl, heteroaryl or heteroaralkyl), or —C(O)N(R')R" (where R' and R" are independently selected from hydrogen or alkyl). Representative examples include, but are not limited to, tetrahydropyranyl, piperidino, piperazino, pyrrolidino, and the like.

Hydroxyalkyl: An alkyl group as defined above substituted with at least one hydroxyl group, provided that if two or more hydroxyl groups are present no two hydroxyl groups are on the same carbon atom.

Inhibiting parasite growth: The phrase "inhibiting parasite growth" (and analogous phrases, such as inhibition of parasite growth or inhibition of parasite proliferation) conveys a wide-range of inhibitory effects that an agent (e.g., an antimalarial composition) may have on a normal (for example, untreated or control) rate of parasite growth. The phrase "inhibiting parasite growth" (or like terminology) may be considered relative to a normal (for example, untreated or control) rate of growth of a particular parasite species (such as *Plasmodium* sp.) or a particular life stage of a parasite (such as a blood-stage and/or liver-stage *Plasmodium* sp. parasite). Thus, inhibiting parasite growth includes situations wherein the normal growth rate of a parasite or a particular life-stage of a parasite has slowed (such that parasite number increases over time, but not as rapidly as in a control population), equals zero (such that there is substantially no change in number of parasites in the population over time, e.g., parasite growth is approximately equal to parasite death), or becomes negative (such that the number of parasites decreases over time, e.g., parasite death exceeds parasite growth). A negative rate of parasite growth can (but need not) result in the death of all parasites in a population. For example, an antimalarial agent may inhibit the rate of parasite growth in a manner such that it may or may not result over time in a decrease in the absolute numbers of parasites in the overall population relative to the numbers of parasites present just prior to administering the agent.

Oxygen-containing group: An R-group containing at least one oxygen atom. Exemplary, non-limiting oxygen containing groups include oxygen alone (which may be attached to the molecule by a single or double bond), hydroxyl, hydroxylalkyl, ether, ester, or any group containing a carbonyl moiety.

Optional: Means that the subsequently described event or circumstance may but need not occur, and that the description includes instances where the event or circumstance occurs and instances in which it does not. For example, "heterocyclo group optionally mono- or di-substituted with an alkyl group" means that the alkyl may but need not be present, and the description includes situations where the heterocyclo group is mono- or disubstituted with an alkyl group and situations where the heterocyclo group is not substituted with the alkyl group.

Phenyl: Phenyl groups may be unsubstituted or substituted with one, two or three substituents, with substituent(s) independently selected from alkyl, heteroalkyl, aliphatic, heteroaliphatic, thioalkoxy, halo, haloalkyl (such as —$CF_3$), nitro, cyano, —OR (where R is hydrogen or alkyl), —N(R)R' (where R and R' are independently of each other hydrogen or alkyl), —COOR (where R is hydrogen or alkyl) or —C(O)N(R')R" (where R' and R" are independently selected from hydrogen or alkyl). Non-limiting examples, include o-, m-, and/or p-chlorophenyl, o-, m-, and/or p-methoxyphenyl, and o-, m-, and/or p-(trifluoromethyl) phenyl.

Sulfonyl: refers to the radical —$SO_2$—. The sulfonyl group can be further substituted with a variety of groups to form, for example, sulfonic acids, sulfonamides, sulfonate esters and sulfones.

Thioalkoxyalkyl: A thioalkoxy group appended to an alkyl radical.

Treating or treatment: With respect to disease, either term includes (1) preventing the disease, e.g., causing the clinical symptoms of the disease not to develop in an animal that may be exposed to or predisposed to the disease but does not yet experience or display symptoms of the disease, (2) inhibiting the disease, e.g., arresting the development of the disease or its clinical symptoms, or (3) relieving the disease, e.g., causing regression of the disease or its clinical symptoms.

Tricyclic ring system: A ring system containing three independently carbocyclic or heterocyclic rings including a central ring and two peripheral rings. Each peripheral ring is fused to the central ring, but neither peripheral ring is fused to the other. Each peripheral ring is aromatic (e.g., phenyl) and can be unsubstituted or substituted as described above for a phenyl group. The central ring can be aromatic or aliphatic, unsaturated or partially saturated (for example, with bridgehead carbons being unsaturated and one or more other ring bonds being saturated), and can be unsubstituted or substituted as described for carbocyclic or heterocyclic rings (and as valence rules allow). Non-limiting examples of a tricyclic ring system include N-xanthenyl, N-phenothiazinyl, N-phenoxazinyl, N-carbazolyl; 10H-acridin-9-one-10-yl; 5,11-dihydro-dibenzo[a,d]cyclohepten-10-one-5-yl; 10,11-dihydro-5H-dibenzo[a,d]cycloheptene-5-yl; 10H-benzo[b][1,8]naphthyridin-5-one-N-yl; 6,11-dihydro-5H-benzo[5,6]cyclohepta[1,2b]pyridine-11-yl.

Compounds that have the same molecular formula but differ in the nature or sequence of bonding of their atoms or the arrangement of their atoms in space are termed "isomers". Isomers that differ in the arrangement of their atoms in space are termed "stereoisomers". Stereoisomers that are not mirror images of one another are termed "diastereomers" and those that are non-superimposable mirror images of each other are termed "enantiomers." When a compound has an asymmetric center, for example, if a carbon atom is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−) isomers respectively). A chiral compound can exist as either individual enantiomer or as a mixture thereof. A mixture containing equal proportions of the enantiomers is called a "racemic mixture."

The compounds described herein may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see, e.g., March, *Advanced Organic Chemistry*, 4th edition, New York:John Wiley and Sons, 1992, Chapter 4).

It is further to be understood that any molecular weight or molecular mass values are approximate and are provided only for description. All publications, patent applications, patents, and other references mentioned herein are incorporated by reference in their entirety. In case of conflict, the present specification, including explanations of terms, will control.

Except as otherwise noted, the methods and techniques of the present invention are generally performed according to conventional methods well known in the art and as described in various general and more specific references that are cited and discussed throughout the present specification. See, e.g., Loudon, *Organic Chemistry*, Fourth Edition, New York: Oxford University Press, 2002, pp. 360-361, 1084-1085; Smith and March, *March's Advanced Organic Chemistry: Reactions, Mechanisms, and Structure*, Fifth Edition, Wiley-Interscience, 2001; or Vogel, *A Textbook of Practical Organic Chemistry, Including Qualitative Organic Analysis*, Fourth Edition, New York:Longman, 1978.

III. RCQ Compounds

Disclosed herein are compounds (referred to as RCQs) useful for the treatment of malaria and *Plasmodium* sp. infection. Such compounds are equally effective against $CQ^R$ and $CQ^S$ strains of *Plasmodium* sp., and provide another weapon in the arsenal against malaria, which cumulatively has killed more people than any other infectious disease in history (e.g., Resolution 61-02, Association of American Physicians and Surgeons, Inc., Tucson, Ariz., 2004; available at the website having the address www.aapsonline.org/resolutions/2004-2.htm). The disclosed compounds can be prepared by any methods known to those of skill in the art; for example by chemical synthesis. Non-limiting exemplary methods for synthesis of particular RCQ embodiments are provided herein.

A. Chemical Formulas

Examples of the disclosed RCQ compounds include compounds of the general, tripartite formula:

Q-L-G wherein Q represents a quinoline derivative of the formula

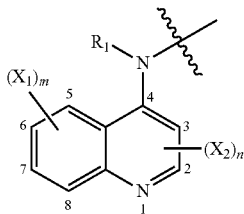

wherein $X_1$ and $X_2$ are independently alkoxy, optionally substituted amino, halo, haloalkyl, hydroxy; n is from 0 to 2; m is from 0 to 4; and $R_1$ is H, optionally substituted alkyl, heteroalkyl, alkylamino, sulfonyl (such as alkyl or aryl sulfonyl), haloalkyl, or carbonyl.

With continued reference to the general formula above, L represents a linker, typically constituting a hydrocarbon chain, optionally branched and/or including heteroatoms, such as nitrogen and/or oxygen. Where the linker group is a hydrocarbon chain, the group typically includes from 2 to about 12 carbon atoms, optionally interrupted by one or more heteroatom. For example, the L can include one or more ethylene glycol groups, ethanolamine groups and/or diaminoethane moieties. Similarly, linkers can include a propyl derivative optionally containing one or more heteroatoms, such as a 1,3-diaminopropyl group. The chain can comprise aliphatic and aryl groups and can comprise straight chain, branched chain and/or cyclic groups, such as heterocyclic groups.

With reference to the general formula above, G represents a reversal agent moiety. Typically, suitable G groups include derivatives of reversal agents having one or more cyclic groups.

In some embodiments, a disclosed RCQ conforms to the chemical structure:

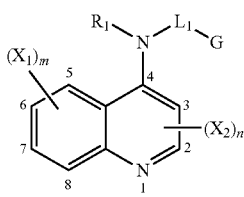

wherein G is

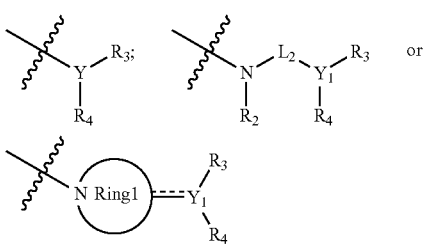

$(X_1)_m$, and $(X_2)_n$ are independently halo, haloalkyl (such as trifluoromethyl), amino, hydroxyl, alkoxy (such as methoxy), alkylamino, or arylamino; m is 0 to 4 (such as 0 to 2, 1 or 2, or 1); n is 0 to 2 (all ring valences are filled by H where m and/or n is 0);

$R_1$ is H, alkyl, heteroalkyl, alkylamino (such as methylamino), haloalkyl (such as trifluoromethyl), amide (such as —C(O)NH$_2$), alkylamide, or alkylsulfonamide;

$R_2$ is H, alkyl (such as methyl or ethyl), heteroalkyl, alkylamino (such as methylamino), haloalkyl (such as trifluoromethyl), alkylsulfonamide, amide, alkylamide (such as —(CH$_2$)$_n$—C(O)NH$_2$, where n is 1, 2, 3, or 4), cyano, furyl, or alkylfuran (such as —(CH$_2$)$_n$-furan, where n is 1, 2, 3, or 4); $L_1$ and $L_2$ are independently alkyl or heteroalkyl;

Y and $Y_1$ independently are N; CH; CH$_2$CH or C(O)CH;

$R_3$ and $R_4$ are independently alkyl, cycloalkyl, heterocyclyl, aryl (such as substituted or unsubstituted phenyl or benzyl), heteroaryl (such as pyridyl, pyridylalkyl, pyrazinyl, furyl, or indolyl) or together with $Y_1$ form a polycyclic ring system, such as a bicyclic or tricyclic ring system; and ring 1 is a five-, six-, or seven-membered heterocyclic ring.

In some examples, $(X_1)_m$ and $(X_2)_n$ are independently halo (such as chloro), haloalkyl (such as trifluoromethyl), or alkoxy (such as methoxy). In other examples, $(X_1)_m$ are independently halo (such as chloro), or haloalkyl (such as trifluoromethyl) and n is 0 (i.e., all ring valences satisfied by H). In more particular examples, n is 0, m is 2, and $(X_1)_1$ and $(X_1)_2$ are $C_7$ and $C_6$ substituents, respectively, which are independently selected from halo (such as chloro), or haloalkyl (such as trifluoromethyl). In even more particular examples, n is 0, m is 1, and $(X_1)_1$ is chloro at position $C_7$. Some non-limiting representative chemical structures illustrating exemplary variations of $(X_1)_m$ and/or $(X_2)_n$ are shown in the following Table 1. The Table 1 structures can also be described as representative antimalarial quinoline derivatives.

TABLE 1

Exemplary Antimalarial Quinoline Moieties

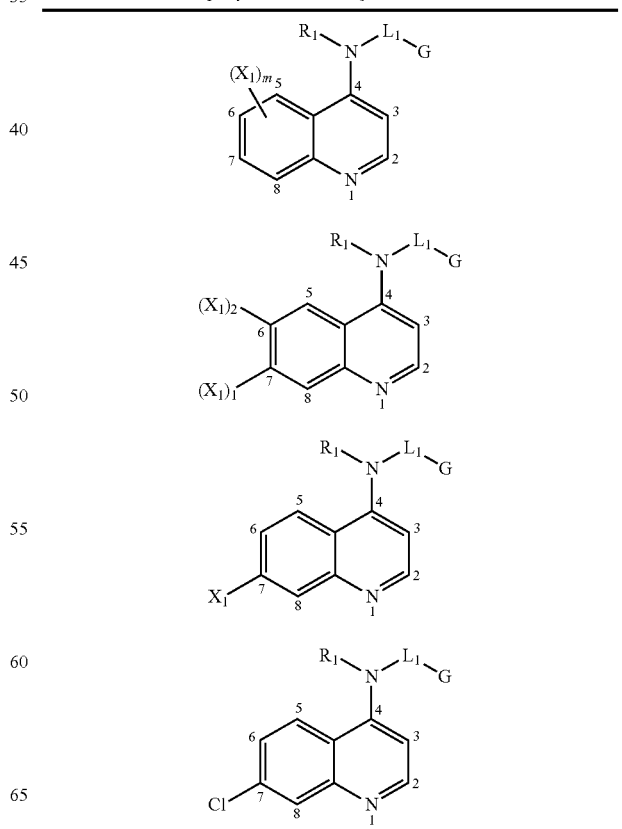

TABLE 1-continued

Exemplary Antimalarial Quinoline Moieties

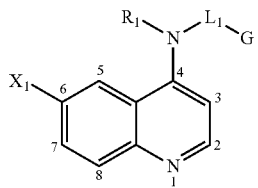

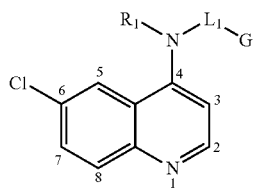

In some embodiments, $R_1$ and $R_2$ are independently H, alkyl having from 1 to 4 carbon atoms (such as from 1 to 2, or 1 carbon atom), or heteroalkyl having from 1 to 4 carbon atoms and at least one heteroatom (such as N, S, or O). In particular examples, $R_1$ and $R_2$ are independently selected from H, methyl, trifluoromethyl, —$CH_2CH_2CF_3$, —$CH_2CF_3$, alkylamine (such as —$CH_2CH_2NH_2$, —$CH_2NH_2$), or alkylamide (such as —$(CH_2)_n$—$C(O)NH_2$, where n is 1, 2, 3, or 4). In more particular examples, $R_1$ and $R_2$ are independently selected from H, methyl or methylamine. In even more particular examples, $R_1$ and $R_2$ are each H. In some embodiments, $R_2$ is further selected from cyano, furyl, or alkylfuran (such as —$(CH_2)_n$-furan, where n is 1, 2, 3, or 4). In specific embodiments, $R_1$ is H and $R_2$ is H, methyl, amine, alkylamine (such as —$(CH_2)_n$—$NH_2$, where n is 1, 2, 3, or 4), amide, alkylamide (such as —$(CH_2)_n$—$C(O)NH_2$, where n is 1, 2, 3, or 4), furyl, alkylfuran (such as —$(CH2)_n$-furan, where n is 1, 2, 3, or 4), or cyano. In other specific embodiments, $R_1$ is H and $R_2$ is H, methyl, methylamine, ethylamine, amide, methylamide, ethylamide, methylfuran, or cyano.

$L_1$ and $L_2$ are each linkers, which are believed to tolerate considerable variation in structure without substantial effect on a biological activity of the RCQ molecule (such as inhibition of $CQ^R$ and/or $CQ^S$ Plasmodium sp. growth). For example, it is known that CQ with only 3 methylene units (at a position analogous to $L_1$ in Formula I) and no branching methyl between the CQ aliphatic amines (at a position analogous to $R_1$ in Formula I) is effective against $CQ^R$ P. falciparum strains (De et al., J. Med. Chem., 41(25):4918-4926, 1998; De et al., Am. J. Trop. Med. Hyg., 55(6):579-583, 1996).

In some embodiments, $L_1$ and $L_2$ are alkyl or heteroalkyl independently having from 1 to 12 atoms (such as from 1 to 7 carbons, from 2 to 5 carbons, or from 3 to 4 carbons). In other embodiments, each carbon in $L_1$ and $L_2$ has two substituents, each of which substituents is independently selected from H, alkyl (such as methyl or ethyl), haloalkyl (such as trifluoromethyl), alkoxy (such as methoxy), amino (such as —$NH_2$), or halo (such as —F or —Cl). In particular embodiments, substituents bonded to one carbon atom are the same so that neither $L_1$ nor $L_2$ include any chiral carbons. In other particular embodiments, $L_1$ and $L_2$ are independently from 1 to 12 atoms in length (such as from 2 to 6 atoms, for example ethyl, propyl, hexyl or the like), and each position of $L_1$ and $L_2$ is independently selected from methylene, dihalomethylene (such as difluoromethylene or dichloromethylene), di(methylamino), —NH—, and —O—. In specific embodiments, $L_1$ and $L_2$ are independently, ethyl, propyl, butyl, —$(CH_2)_{n1}$—O—$(CH_2)_{n2}$— (where n1 and n2 are independently 1, 2, 3, or 4), or —$(CH_2)_n$—NH— (where n is 1, 2, 3, or 4). In even more specific embodiments, $L_1$ is ethyl, propyl, or butyl, and $L_2$ is ethyl, propyl, butyl, —$CH_2$—O—$CH_2$—, or —$(CH_2)_2$—NH—. In still more specific embodiments, $L_1$ and $L_2$ are independently, ethyl, propyl, or butyl moieties.

Some non-limiting representative chemical structures illustrating exemplary variations of alkyl $L_1$ and/or $L_2$ are shown in the following table.

TABLE 2

Exemplary Alkyl Linkers

| R7 | R8 | R9 | R10 | o | p |
|---|---|---|---|---|---|
| H | H | H | H | 2, 3, or 4 | 2, 3, or 4 |
| —$CH_3$ | —$CH_3$ | —$CH_3$ | —$CH_3$ | 2, 3, or 4 | 2, 3, or 4 |
| —$CH_2CH_3$ | —$CH_2CH_3$ | —$CH_2CH_3$ | —$CH_2CH_3$ | 2, 3, or 4 | 2, 3, or 4 |
| —$CF_3$ | —$CF_3$ | —$CF_3$ | —$CF_3$ | 2, 3, or 4 | 2, 3, or 4 |
| —F | —F | —F | —F | 2, 3, or 4 | 2, 3, or 4 |
| —$NH_2$ | —$NH_2$ | —$NH_2$ | —$NH_2$ | 2, 3, or 4 | 2, 3, or 4 |
| H | H | —$CH_3$ | —$CH_3$ | 2, 3, or 4 | 2, 3, or 4 |
| H | H | —$CH_2CH_3$ | —$CH_2CH_3$ | 2, 3, or 4 | 2, 3, or 4 |
| H | H | —$CF_3$ | —$CF_3$ | 2, 3, or 4 | 2, 3, or 4 |
| H | H | —F | —F | 2, 3, or 4 | 2, 3, or 4 |
| H | H | —$NH_2$ | —$NH_2$ | 2, 3, or 4 | 2, 3, or 4 |
| —$CH_3$ | —$CH_3$ | H | H | 2, 3, or 4 | 2, 3, or 4 |
| —$CH_2CH_3$ | —$CH_2CH_3$ | H | H | 2, 3, or 4 | 2, 3, or 4 |
| —$CF_3$ | —$CF_3$ | H | H | 2, 3, or 4 | 2, 3, or 4 |
| —F | —F | H | H | 2, 3, or 4 | 2, 3, or 4 |
| —$NH_2$ | —$NH_2$ | H | H | 2, 3, or 4 | 2, 3, or 4 |
| —$CH_3$ | —$CH_3$ | —$CH_2CH_3$ | —$CH_2CH_3$ | 2, 3, or 4 | 2, 3, or 4 |
| —$CH_3$ | —$CH_3$ | —$CF_3$ | —$CF_3$ | 2, 3, or 4 | 2, 3, or 4 |
| —$CH_3$ | —$CH_3$ | —F | —F | 2, 3, or 4 | 2, 3, or 4 |
| —$CH_3$ | —$CH_3$ | —$NH_2$ | —$NH_2$ | 2, 3, or 4 | 2, 3, or 4 |
| —$CH_2CH_3$ | —$CH_2CH_3$ | —$CH_3$ | —$CH_3$ | 2, 3, or 4 | 2, 3, or 4 |
| —$CF_3$ | —$CF_3$ | —$CH_3$ | —$CH_3$ | 2, 3, or 4 | 2, 3, or 4 |
| —F | —F | —$CH_3$ | —$CH_3$ | 2, 3, or 4 | 2, 3, or 4 |
| —$NH_2$ | —$NH_2$ | —$CH_3$ | —$CH_3$ | 2, 3, or 4 | 2, 3, or 4 |
| —$CH_2CH_3$ | —$CH_2CH_3$ | —$CF_3$ | —$CF_3$ | 2, 3, or 4 | 2, 3, or 4 |
| —$CH_2CH_3$ | —$CH_2CH_3$ | —F | —F | 2, 3, or 4 | 2, 3, or 4 |
| —$CH_2CH_3$ | —$CH_2CH_3$ | —$NH_2$ | —$NH_2$ | 2, 3, or 4 | 2, 3, or 4 |
| —$CF_3$ | —$CF_3$ | —$CH_2CH_3$ | —$CH_2CH_3$ | 2, 3, or 4 | 2, 3, or 4 |
| —F | —F | —$CH_2CH_3$ | —$CH_2CH_3$ | 2, 3, or 4 | 2, 3, or 4 |
| —$NH_2$ | —$NH_2$ | —$CH_2CH_3$ | —$CH_2CH_3$ | 2, 3, or 4 | 2, 3, or 4 |
| —$CF_3$ | —$CF_3$ | —F | —F | 2, 3, or 4 | 2, 3, or 4 |
| —$CF_3$ | —$CF_3$ | —$NH_2$ | —$NH_2$ | 2, 3, or 4 | 2, 3, or 4 |
| —F | —F | —$CF_3$ | —$CF_3$ | 2, 3, or 4 | 2, 3, or 4 |
| —$NH_2$ | —$NH_2$ | —$CF_3$ | —$CF_3$ | 2, 3, or 4 | 2, 3, or 4 |
| —F | —F | —$NH_2$ | —$NH_2$ | 2, 3, or 4 | 2, 3, or 4 |
| —$NH_2$ | —$NH_2$ | —F | —F | 2, 3, or 4 | 2, 3, or 4 |

Exemplary $R_3$ and $R_4$ groups include aryl groups and substituted alkyl groups, such as cyclohexyl, methylcyclohexyl (—$CH_2C_6H_{11}$), adamantyl, methyl adamantyl and ethyl adamantyl. Typically, at least one of $R_3$ and $R_4$ is a sterically bulky group. Suitable sterically bulky groups for incorporation as $R_3$ and/or $R_4$ will be readily apparent to those of ordinary skill in the art upon consideration of the present disclosure.

Other exemplary compounds disclosed herein conform to the chemical structure:

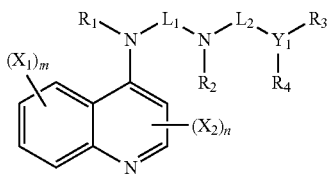

wherein $(X_1)_m$, $(X_2)_n$, $R_1$, $R_2$, $L_1$, $L_2$, $Y_1$, $R_3$ and $R_4$ are as described for above.

In one aspect of this formula $R_3$ and $R_4$ can represent arylalkyl groups, which may be the same or different. For example, a specific group of RCQ compound structures have the formula:

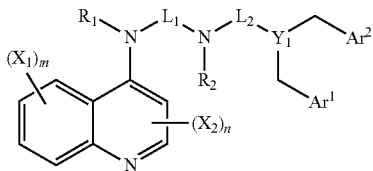

wherein $Ar^1$ and $Ar^2$ are independently selected aryl groups. In one embodiment, such compounds have an oxygen-containing linker group, for example:

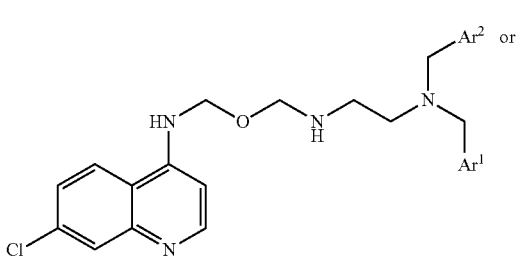

In some embodiments, $R_3$ and $R_4$ independently have a chemical structure as follows:

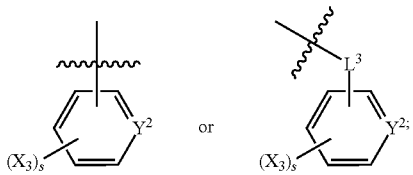

where each $X_3$ is independently halo, haloalkyl (such as trifluoromethyl), amino, hydroxyl, hydroxyalkyl, alkylamino, cyano, alkoxy, sulfonamide, mercapto, keto, or carboxyl; s is 0 to 5 as valence requirements permit (for example, when $Y_2$ is nitrogen, s is from 0 to 4); $Y_2$ is C, S, or N; $L_3$ is a linker, which is alkyl, heteroalkyl, —N—, —O—, or —S—.

In some examples, $(X_3)_s$ are independently fluoro, chloro, trifluoromethyl, methoxy, amine (e.g., —NH$_2$), carboxyl (e.g., —COOH), sulfonamide (e.g., —SO$_2$NH$_2$), hydroxylalkyl (e.g., —(CH2)$_n$—OH, where n is 1, 2, 3, or 4), and/or s is 0 to 3, 0 to 2, or 1. In other examples, $Y_2$ is nitrogen. In particular examples, $L_3$ is alkyl (such as methyl, ethyl, propyl, i-propyl, or butyl), alkoxy (such as methoxy or ethoxy), alkylamino (such as methylamino or ethylamino), —N—, or —O—. In some instances, $R_3$ and $R_4$ are the same (referred to as, symmetric) and, in other instances, $R_3$ and $R_4$ are different, such compounds are referred to herein as being asymmetric.

In other examples, $X_3$ is independently fluoro, chloro, trifluoromethyl, or methoxy. $X_3$ can be independently selected from these groups for each occurrence "s." In still other examples, $L_3$ is methyl, ethyl, methoxy, —N—, or —O—.

In some embodiments, $R_3$ and $R_4$ together with $Y_1$ form the central ring of a polycyclic ring system, such as a bicyclic or tricyclic ring system. In particular embodiments, the central ring formed by $R_3$, $R_4$, and $Y_1$ is a 5-, 6-, or 7-membered ring. Examples of suitable structures for a tricyclic ring system formed by $R_3$, $R_4$, and $Y_1$ include, without limitation:

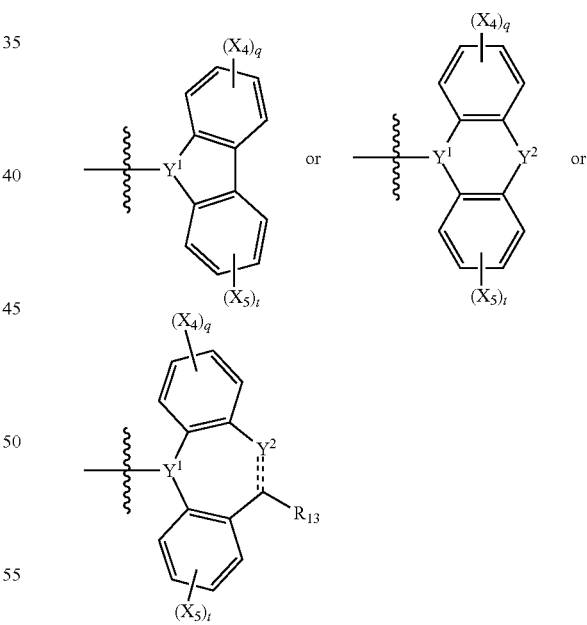

where $Y_2$ is $NR_{14}$, O, or S; $R_{13}$ is H, alkyl, heteroalkyl, =O, amino, amine, amide, sulfonamide, halo (such as F, Cl), cyano, hydroxy, mercapto, haloalkyl (such as trifluoromethyl), alkoxy (such as methoxy), alkylthio, thioalkoxy, arylalkyl, heteroaryl, alkylamino, dialkylamino, or alkylsulfano; $(X_4)_q$ and $(X_5)_t$ are independently H, alkyl, halo (such as F, Cl), haloalkyl (such as trifluoromethyl), alkoxy (such methoxy), amino, hydroxyl, alkylamino, cyano, or mercapto; $R_{14}$ is H, lower alkyl or acyl; q and t are independently 0 to 4 as valence requirements permit (such as 0 to 2, 1 or 2, or 1); and each of the peripheral rings can independently include at least one heteroatom (such as N) at any position that valence requirements permit. In some examples, $(X_4)_q$ and $(X_5)_t$ are independently H, methyl, fluoro, chloro, trifluoromethyl, methoxy, or cyano. In other examples, $Y_2$ is N or S. In particular examples, $R_{13}$ is H or =O (and the ring carbon, which is double bonded to oxygen is otherwise single bonded to adjacent atoms).

Some specific embodiments of RCQ compounds are provided in the following table.

TABLE 3

Exemplary RCQ Compounds

[Structure: RCQ core with $L_1$, $L_2$, $R_2$, $R_3$, $R_4$ substituents]

[Structure: RCQ_05]

[Structure: RCQ_06]

[Structure: RCQ_07]

TABLE 3-continued

Exemplary RCQ Compounds

[Structure: RCQ_08]

[Structure: RCQ_05(desMe)]

[Structure: RCQ_06(desMe)]

[Structure: RCQ_07(desMe)]

[Structure: RCQ_08(desMe)]

TABLE 3-continued
Exemplary RCQ Compounds
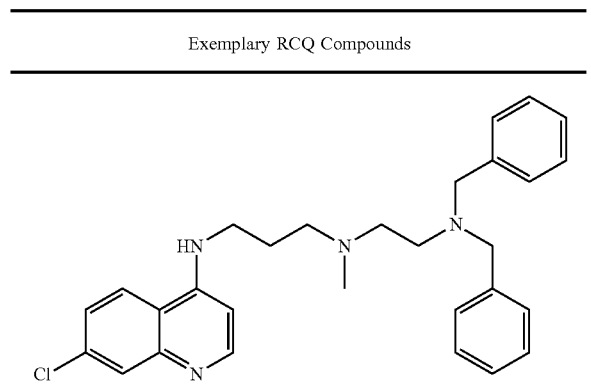
RCQ_09
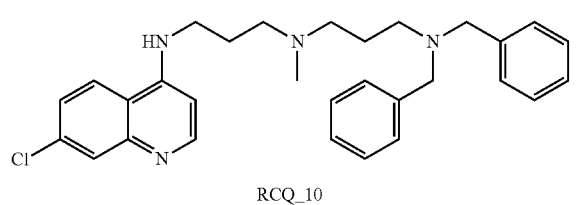 [SMILES: CN(CCCNc1ccnc2cc(Cl)ccc12)CCCN(Cc1ccccc1)Cc1ccccc1]
RCQ_10
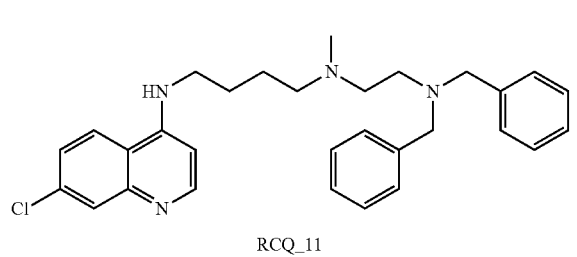 [SMILES: CN(CCCCNc1ccnc2cc(Cl)ccc12)CCN(Cc1ccccc1)Cc1ccccc1]
RCQ_11
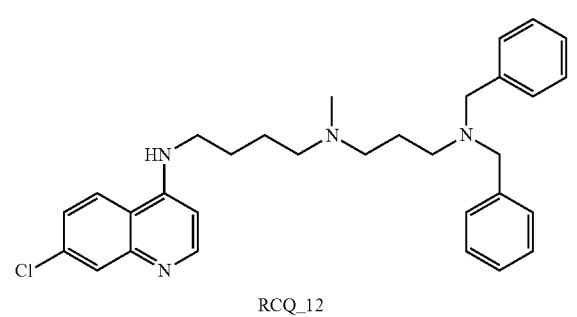 [SMILES: CN(CCCCNc1ccnc2cc(Cl)ccc12)CCCN(Cc1ccccc1)Cc1ccccc1]
RCQ_12
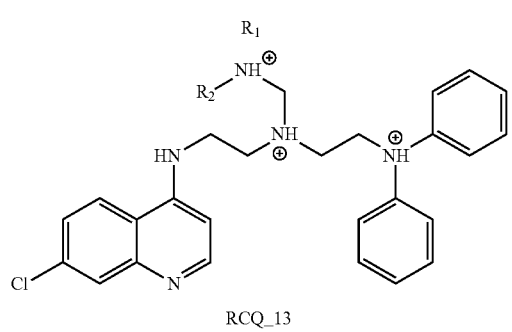
RCQ_13
TABLE 3-continued
Exemplary RCQ Compounds
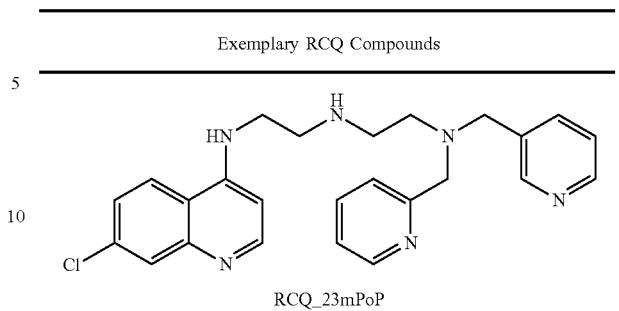
RCQ_23mPoP
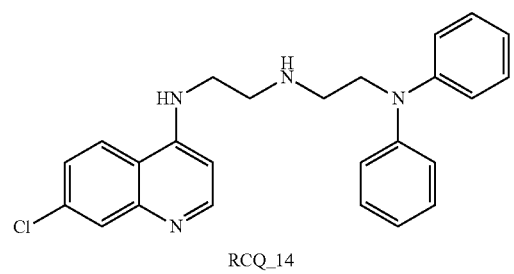 [SMILES: Clc1ccc2c(NCCNCCN(c3ccccc3)c3ccccc3)ccnc2c1]
RCQ_14
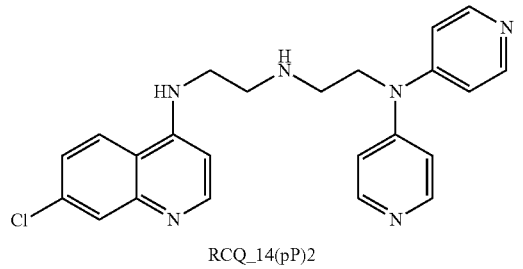 [SMILES: Clc1ccc2c(NCCNCCN(c3ccncc3)c3ccncc3)ccnc2c1]
RCQ_14(pP)2
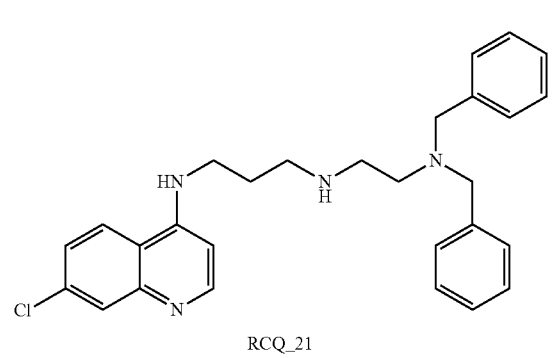 [SMILES: Clc1ccc2c(NCCCNCCN(Cc3ccccc3)Cc3ccccc3)ccnc2c1]
RCQ_21
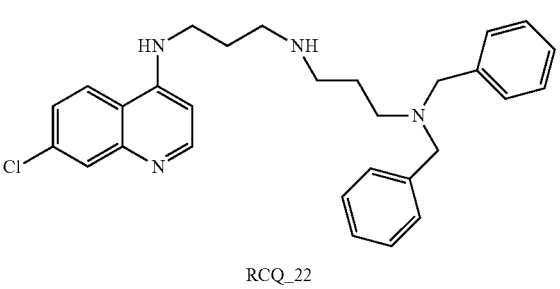 [SMILES: Clc1ccc2c(NCCCNCCCN(Cc3ccccc3)Cc3ccccc3)ccnc2c1]
RCQ_22

TABLE 3-continued
Exemplary RCQ Compounds
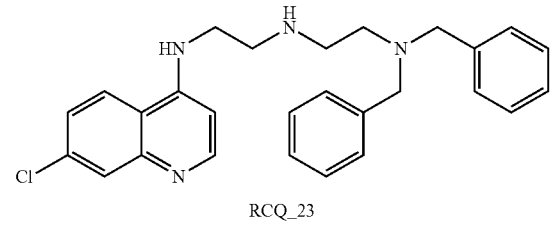 [SMILES: Clc1ccc2c(NCCNCCN(Cc3ccccc3)Cc3ccccc3)ccnc2c1]
RCQ_23
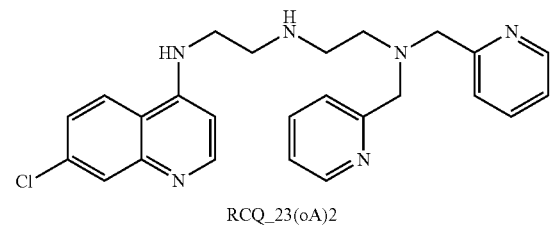 [SMILES: Clc1ccc2c(NCCNCCN(Cc3ccccn3)Cc3ccccn3)ccnc2c1]
RCQ_23(oA)2
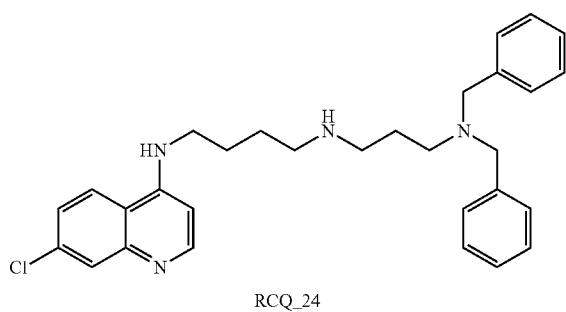 [SMILES: Clc1ccc2c(NCCCCNCCCN(Cc3ccccc3)Cc3ccccc3)ccnc2c1]
RCQ_24
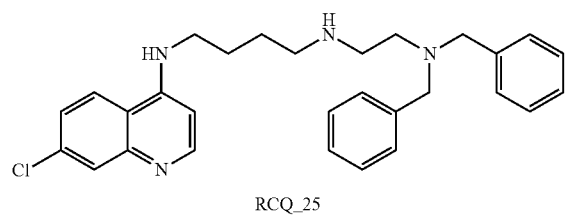 [SMILES: Clc1ccc2c(NCCCCNCCN(Cc3ccccc3)Cc3ccccc3)ccnc2c1]
RCQ_25
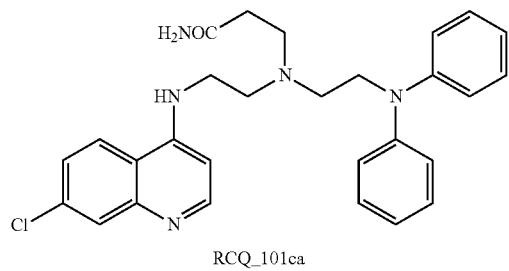 [SMILES: NC(=O)CCN(CCNc1ccnc2cc(Cl)ccc12)CCN(c1ccccc1)c1ccccc1]
RCQ_101ca
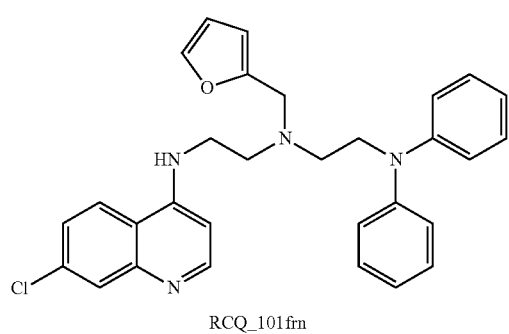 [SMILES: Clc1ccc2c(NCCN(CCN(c3ccccc3)c3ccccc3)Cc3ccco3)ccnc2c1]
RCQ_101frn
TABLE 3-continued
Exemplary RCQ Compounds
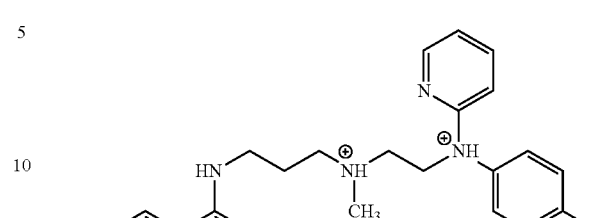
RCQ_102
(a chlorpheniramine derivative)
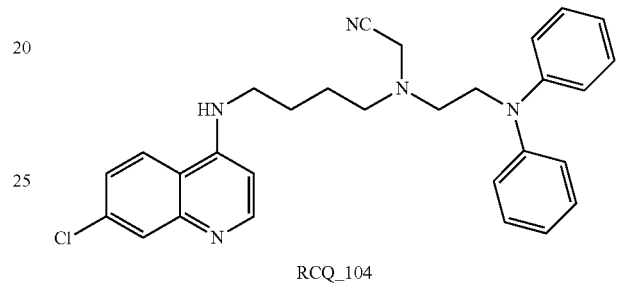
RCQ_104
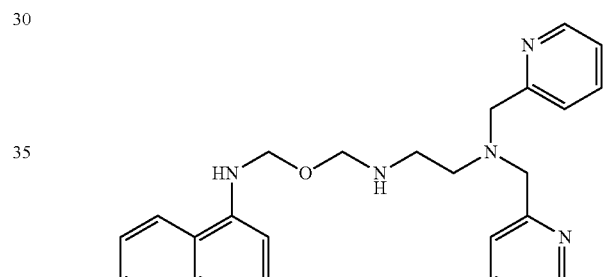
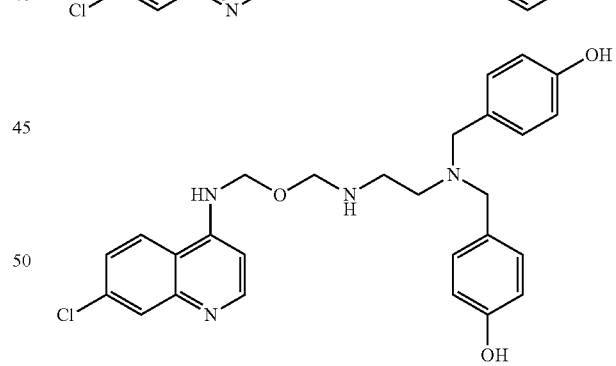
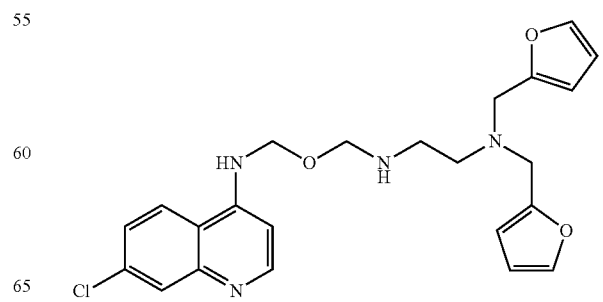

TABLE 3-continued
Exemplary RCQ Compounds
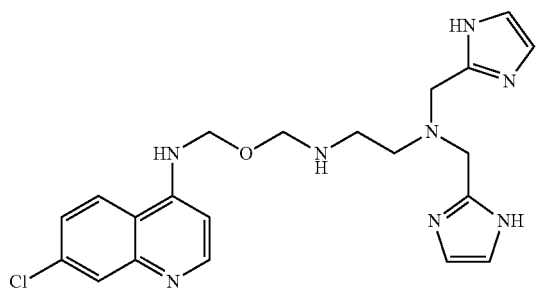 [SMILES: Clc1ccc2c(NCOCNCCN(Cc3ncc[nH]3)Cc3ncc[nH]3)ccnc2c1]
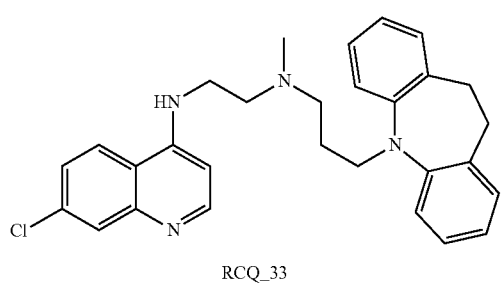
RCQ_33
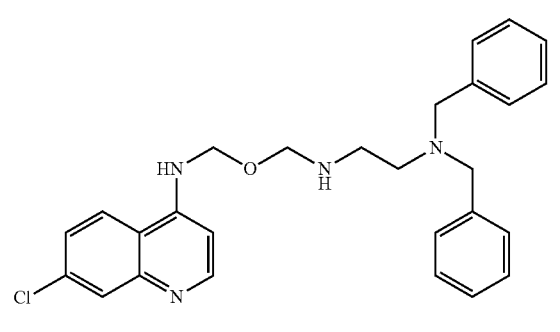 [SMILES: Clc1ccc2c(NCOCNCCN(Cc3ccccc3)Cc3ccccc3)ccnc2c1]
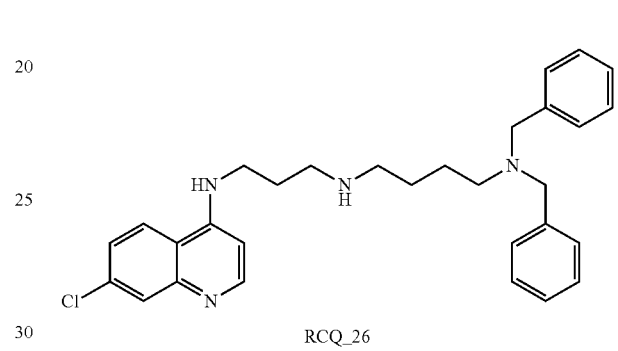
RCQ_26
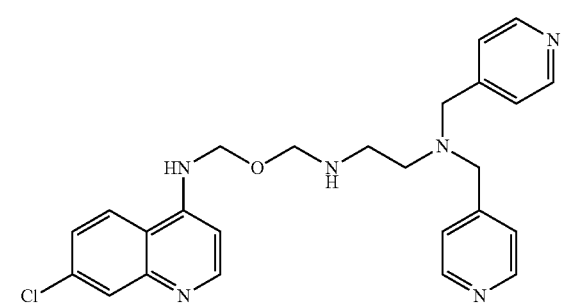 [SMILES: Clc1ccc2c(NCOCNCCN(Cc3ccncc3)Cc3ccncc3)ccnc2c1]
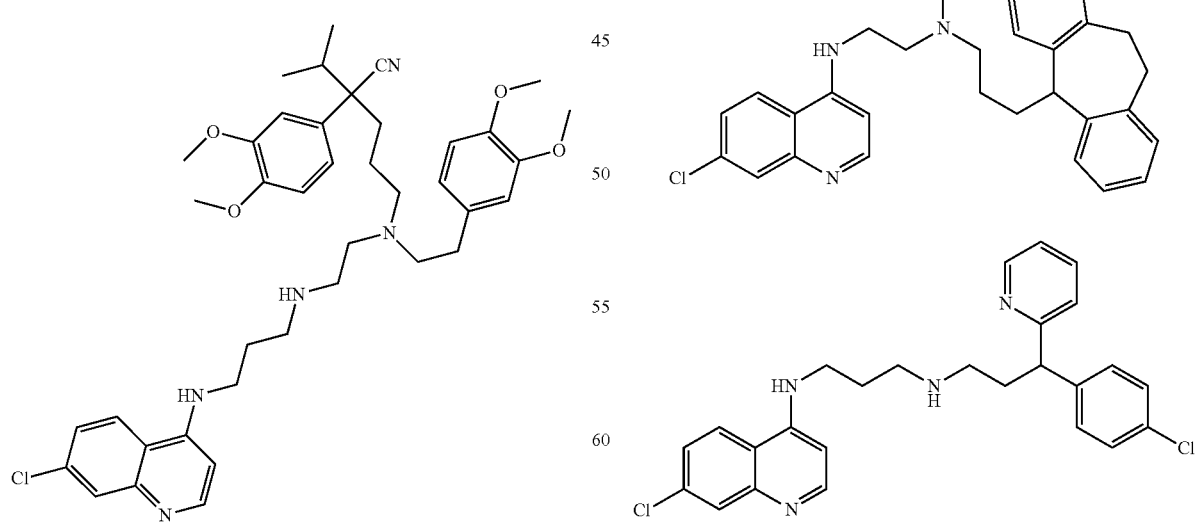
RCQ_150
(a verapamil derivative)
RCQ_101
(a chlorpheniramine derivative)

TABLE 3-continued
Exemplary RCQ Compounds
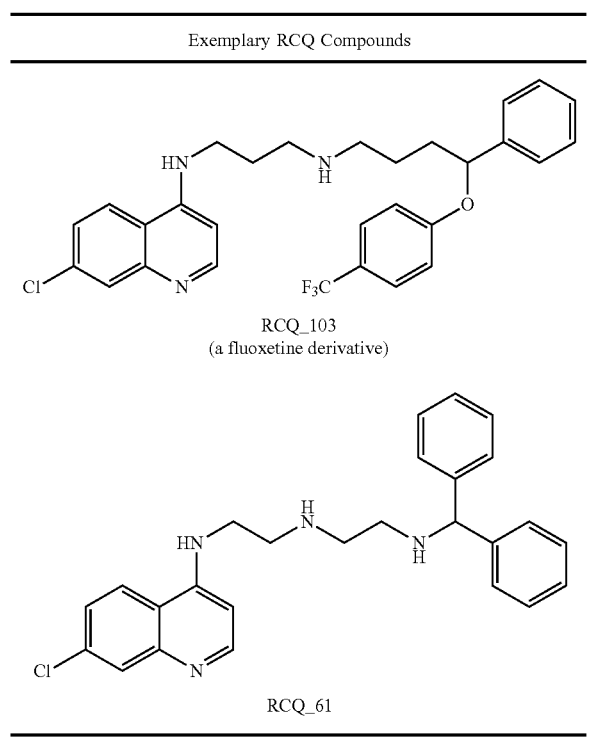
RCQ_103
(a fluoxetine derivative)
RCQ_61
RCQ_01
RCQ_02
TABLE 3-continued
Exemplary RCQ Compounds
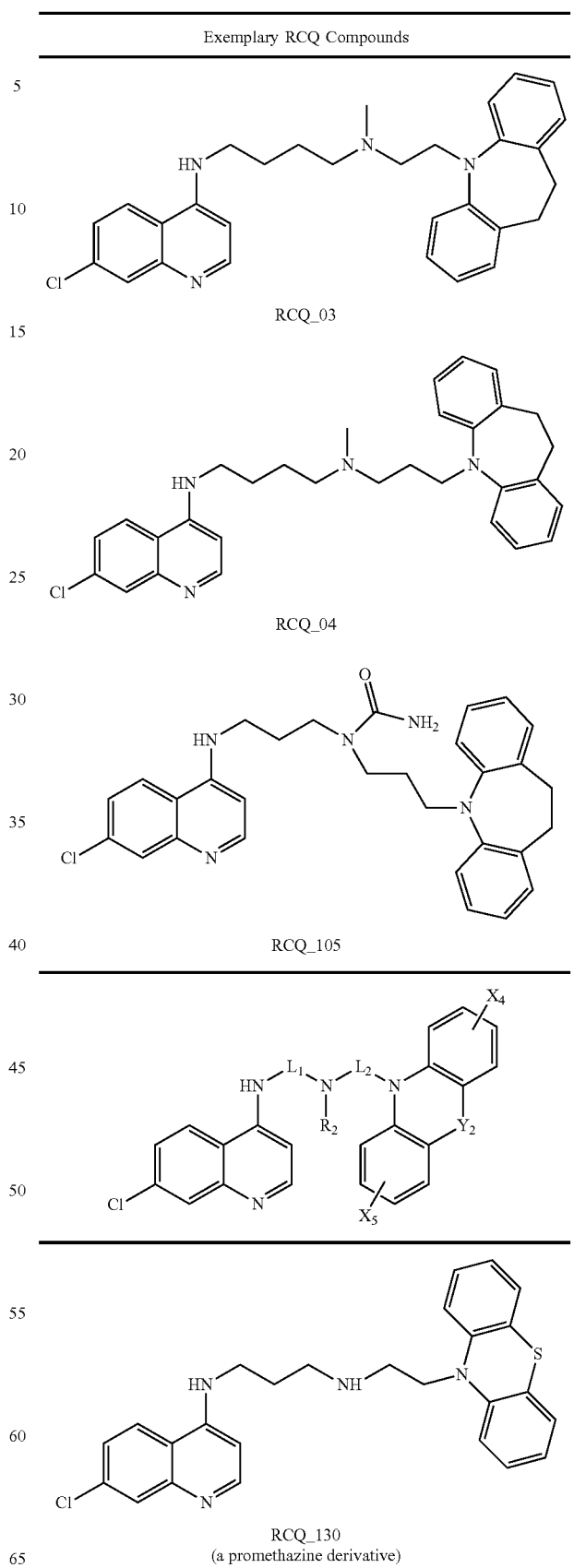
RCQ_03
RCQ_04
RCQ_105
RCQ_130
(a promethazine derivative)

TABLE 3-continued

Exemplary RCQ Compounds

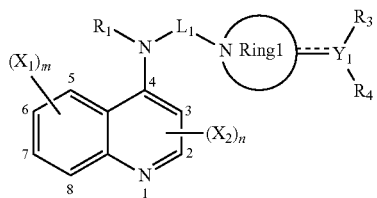

RCQ_131
(a promethazine derivative)

RCQ_132

RCQ_133

Also disclosed herein are compounds that conform to the chemical structure:

where $(X_1)_m$, $(X_2)_n$, $R_1$, and $L_1$ are as described above. Ring 1 is a five-, six- or seven-membered heterocyclic ring; $Y_1$ is carbon; $R_3$ and $R_4$ are independently aryl or heteroaryl, or together with $Y_1$ form a tricyclic ring system.

In some embodiments, Ring 1 has the following structure:

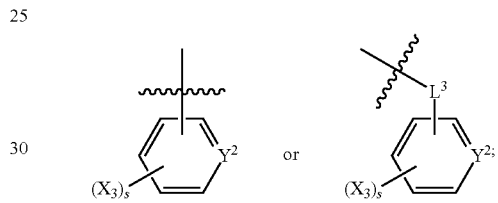

In some embodiments of this formula, and as described above, $R_3$ and $R_4$ are aryl groups. Examples of suitable aryl groups for $R_3$ and $R_4$ include, without limitation those of the formula:

wherein $(X_3)_s$, s, $Y_2$, and $L_3$ are as described above.

In other examples, $Y_1$, $R_3$ and $R_4$ form the center ring of a tricyclic ring system. Non-limiting exemplary structures for a tricyclic ring system formed by $Y_1$, $R_3$ and $R_4$ include:

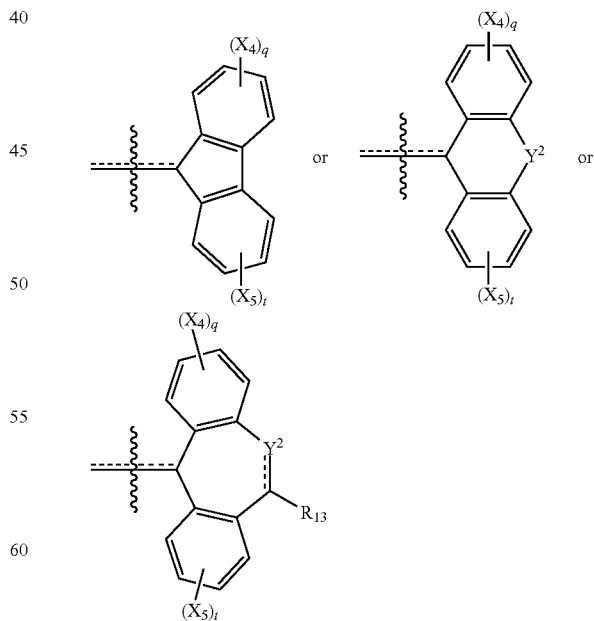

where $Y_2$ is $NR_{14}$, O, CH (when $Y_2$ double bonded to $CR_{13}$), $CH_2$ or S; $R_{13}$ is H, alkyl, heteroalkyl, =O, amino, amine, amide, sulfonamide, halo (such as F, Cl), cyano, hydroxy, mercapto, haloalkyl (such as trifluoromethyl), alkoxy (such as methoxy), alkylthio, thioalkoxy, arylalkyl, heteroaryl, alkylamino, dialkylamino, or alkylsulfano; $(X_4)_q$ and $(X_5)_t$ are independently alkyl, halo (such as F or Cl), haloalkyl (such as trifluoromethyl), alkoxy (such methoxy), amino, hydroxyl, alkylamino, cyano, or mercapto; $R_{14}$ is H, acyl or lower alkyl; q and t are independently 0 to 4 as valence requirements permit (hydrogen satisfies all ring valence requirements where q or t is 0); and each of the peripheral rings can independently include at least one heteroatom (such as N) at any position that valence requirements permit. In some examples, $(X_4)_q$ and $(X_5)_t$ are independently methyl, fluoro, chloro, trifluoromethyl, methoxy, or cyano. In other examples, $Y_2$ is N or S. In particular examples, $R_{13}$ is H or =O (and the ring carbon, which is double bonded to oxygen is otherwise single bonded to adjacent atoms).

Some specific embodiments of disclosed tetrasubstituted ethylene-based RCQ compounds are listed in Table 4.

TABLE 4

Exemplary Tetrasubstituted Ethylene-Based Embodiments

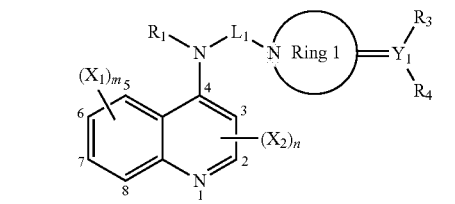

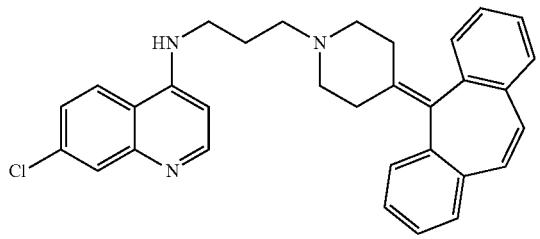

RCQ_42

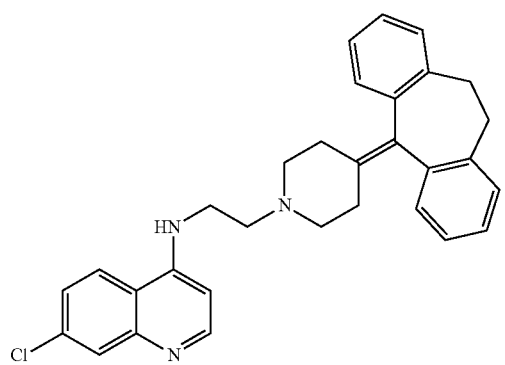

RCQ_41H2

TABLE 4-continued

Exemplary Tetrasubstituted Ethylene-Based Embodiments

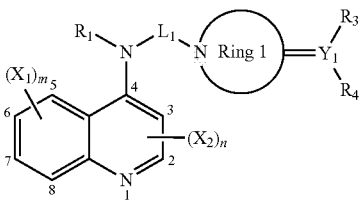

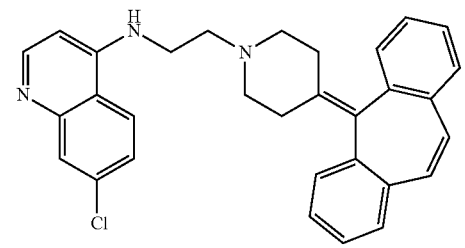

RCQ_110
(a cyproheptadine derivative)

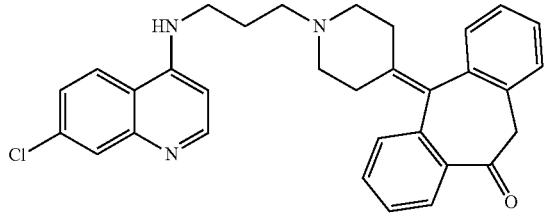

RCQ_111
(a ketotifen derivative)

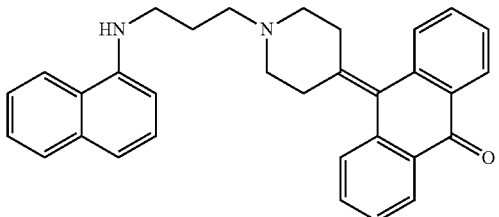

RCQ_112
(an azatadine derivative)

RCQ_113
10H-anthracen-9-one derivative

TABLE 4-continued

Exemplary Tetrasubstituted Ethylene-Based Embodiments

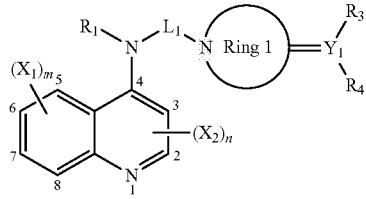

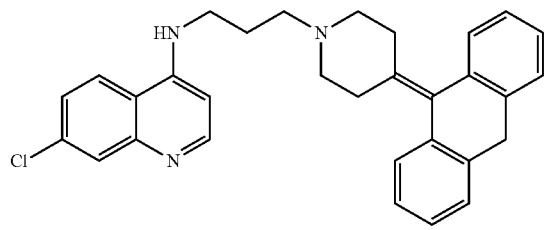

RCQ_114
10H-Anthracen-9-ylidene derivative

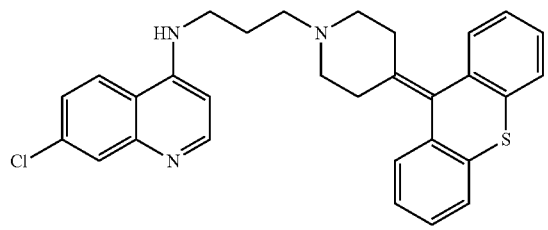

RCQ_115
4-thioxanthen-9-ylidene-piperidin-1-yl derivative

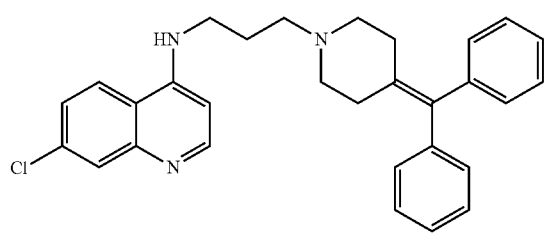

RCQ_116
4-Benzhydrylidene derivative

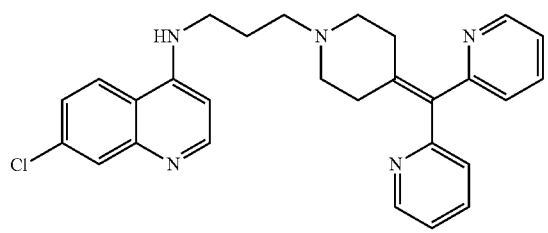

RCQ_117
Dipyridin-2-yl-methylene derivate

Also disclosed herein are compounds that conform to the chemical structure:

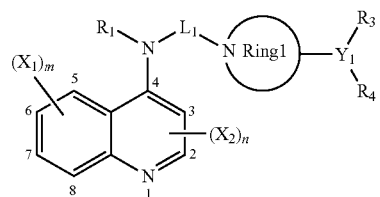

where $(X_1)_m$, $(X_2)_n$, $R_1$, and $L_1$ are as described above. In some embodiments, $L_1$ is also —$(CH_2)_{n1}$—$N(R')$—$(CH_2)_{n2}$—$N(R'')$—$(CH_2)_{n3}$— (where n1, n2, and n3 are independently 1, 2, 3, or 4, and R' and R'' are independently H or alkyl (such as methyl, ethyl or propyl). Ring 1 is a five-, six- or seven-membered heterocyclic ring; Y represents —N—; —CH—; —CH$_2$CH— or —C(O)CH—; $R_3$ and $R_4$ are independently cycloalkyl, aryl or heteroaryl. In certain examples $R_3$ and $R_4$ and $Y_1$ together form a ring system, such as a bicyclic or tricyclic ring system, which can include aliphatic rings, aromatic rings, or both.

In particular examples, a ring system formed by $Y_1$, $R_3$ and $R_4$ has the following structure:

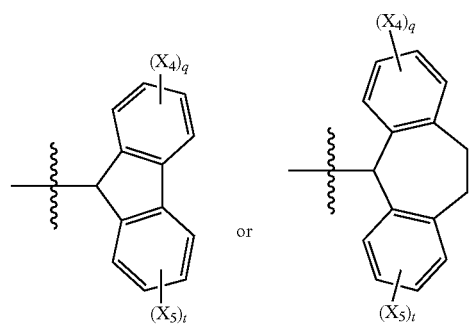

where $(X_4)_q$ and $(X_5)_t$ are independently lower alkyl (such as methyl), halo (such as fluoro or chloro), haloalkyl (such as trifluoromethyl), alkoxy (such as methoxy) or cyano. In some examples, q and t are each 0 and all ring valence requirements are satisfied by hydrogen.

TABLE 5

Exemplary Tricyclic RCQ Compounds

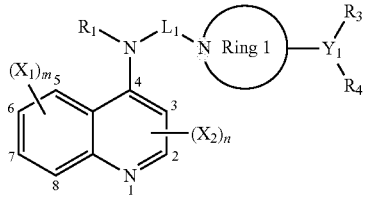

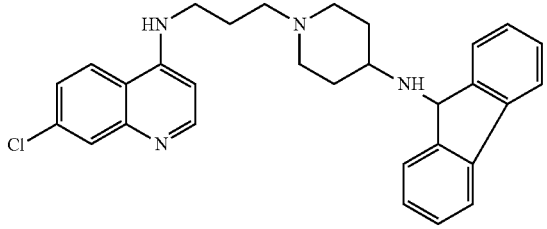 [SMILES: Clc1ccc2c(NCCCN3CCC(NC4c5ccccc5-c5ccccc54)CC3)ccnc2c1]

TABLE 5-continued
Exemplary Tricyclic RCQ Compounds
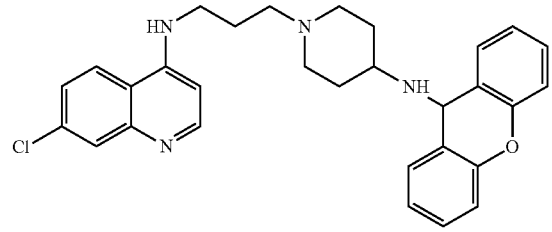 [SMILES: Clc1ccc2c(NCCCN3CCC(NC4c5ccccc5Oc5ccccc54)CC3)ccnc2c1]
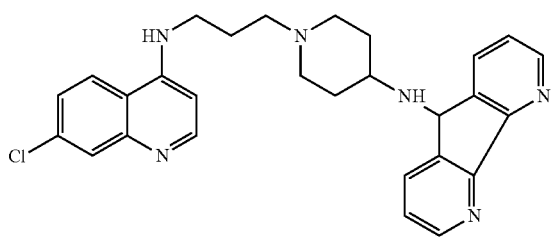 [SMILES: Clc1ccc2c(NCCCN3CCC(NC4c5cccnc5-c5ncccc54)CC3)ccnc2c1]
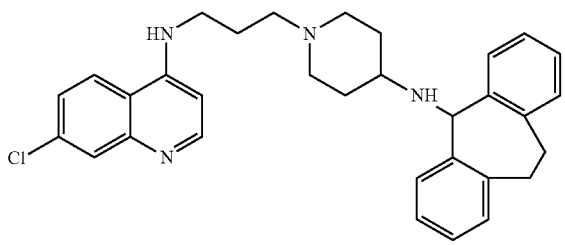 [SMILES: Clc1ccc2c(NCCCN3CCC(NC4c5ccccc5CCc5ccccc54)CC3)ccnc2c1]
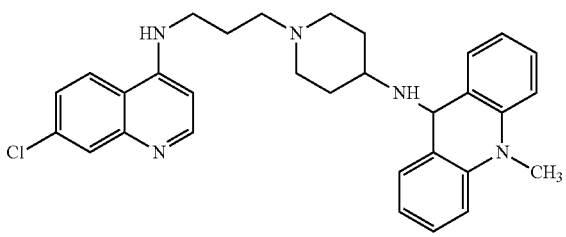 [SMILES: CN1c2ccccc2C(NC2CCN(CCCNc3ccnc4cc(Cl)ccc34)CC2)c2ccccc21]
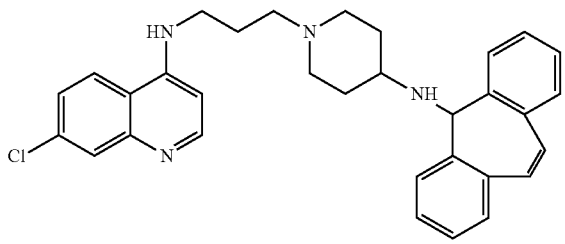 [SMILES: Clc1ccc2c(NCCCN3CCC(NC4c5ccccc5C=Cc5ccccc54)CC3)ccnc2c1]
TABLE 5-continued
Exemplary Tricyclic RCQ Compounds
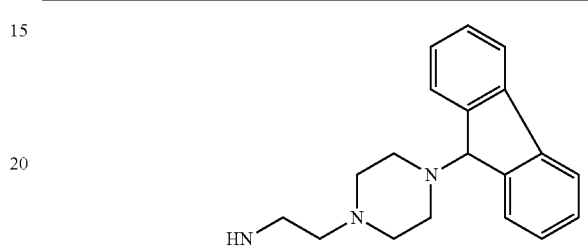
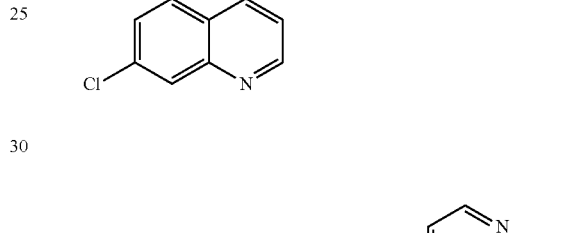
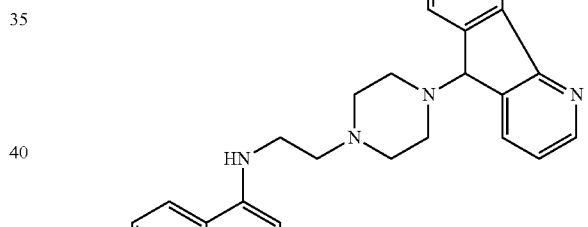
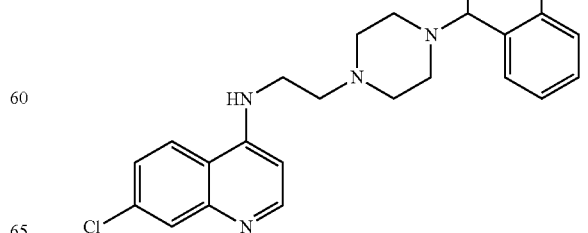

TABLE 5-continued
Exemplary Tricyclic RCQ Compounds
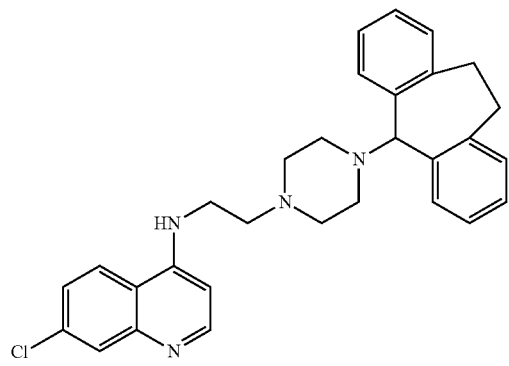 [SMILES: Clc1ccc2c(NCCN3CCN(C4c5ccccc5CCc5ccccc54)CC3)ccnc2c1]
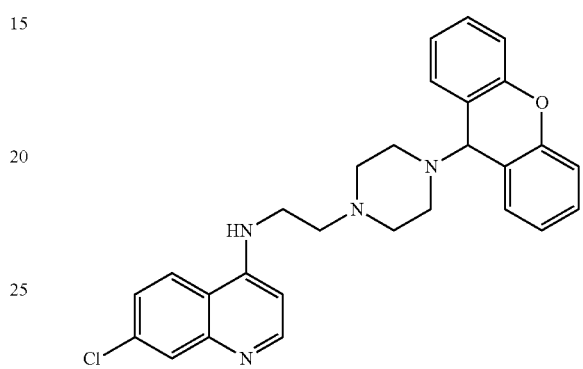
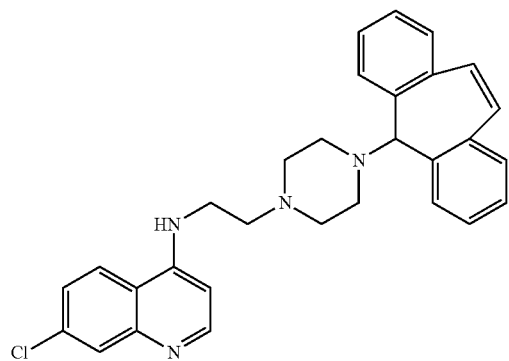 [SMILES: Clc1ccc2c(NCCN3CCN(C4c5ccccc5C=Cc5ccccc54)CC3)ccnc2c1]
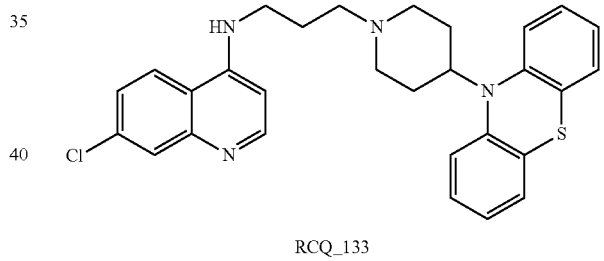
RCQ_133
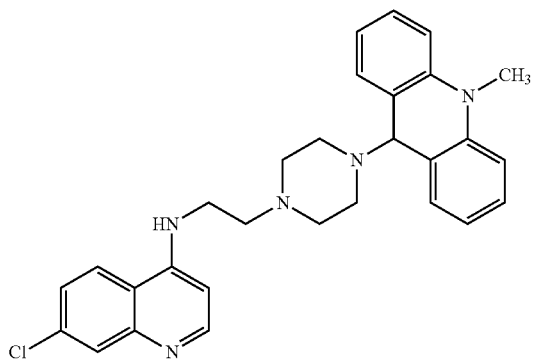 [SMILES: CN1c2ccccc2C(N2CCN(CCNc3ccnc4cc(Cl)ccc34)CC2)c2ccccc21]
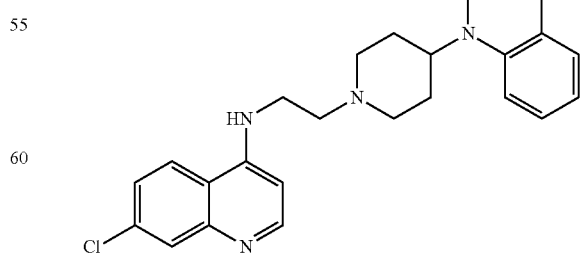
RCQ_134

TABLE 5-continued

Exemplary Tricyclic RCQ Compounds

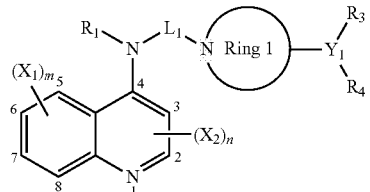

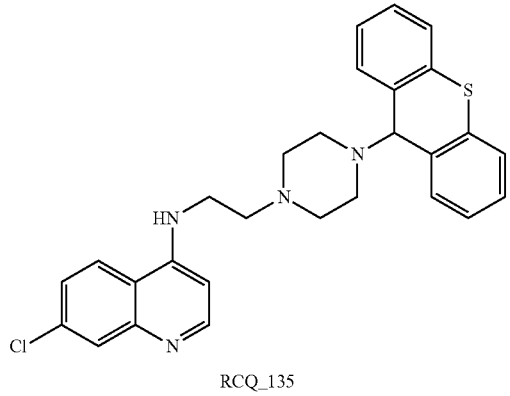 [SMILES: Clc1ccc2c(NCCN3CCC(N4c5ccccc5Sc5ccccc54)CC3)ccnc2c1]

RCQ_135

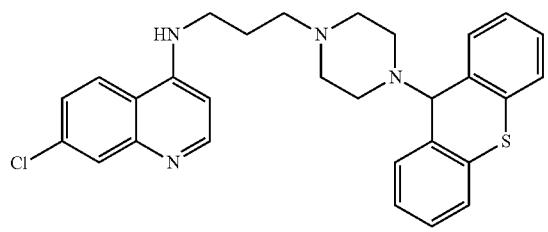

RCQ_136

In one embodiment, $Y_1$, $R_3$ and $R_4$ together form an aliphatic ring system, for example a sterically bulky ring system, such as

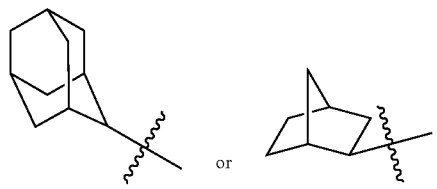 [SMILES: *C1C2CC3CC(C2)CC1C3 ; *C1CC2CCC1C2]

In one aspect, disclosed RCQ compounds are represented by the formula:

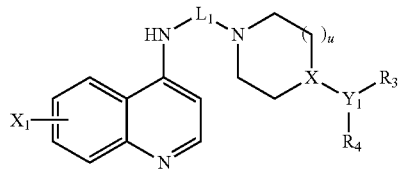

wherein $X_1$ is a halogen; X represents —N— or —CH—; $Y_1$ represents —N—; —CH—; —CH$_2$CH— or —C(O)CH— and u is from 0 to 2. Embodiments of such compounds can have the formula:

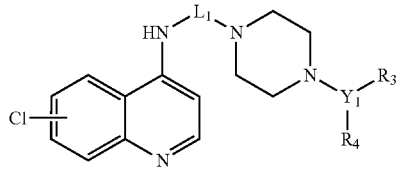

and specific examples of such compounds are recited in Table 6.

TABLE 6

Exemplary Piperazine-based RCQ Compounds

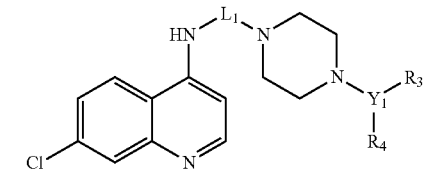

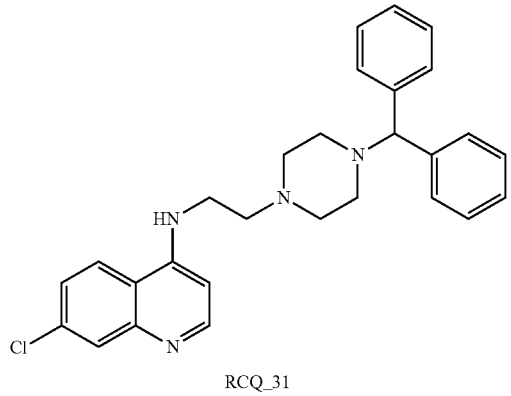 [SMILES: Clc1ccc2c(NCCN3CCN(C(c4ccccc4)c4ccccc4)CC3)ccnc2c1]

RCQ_31

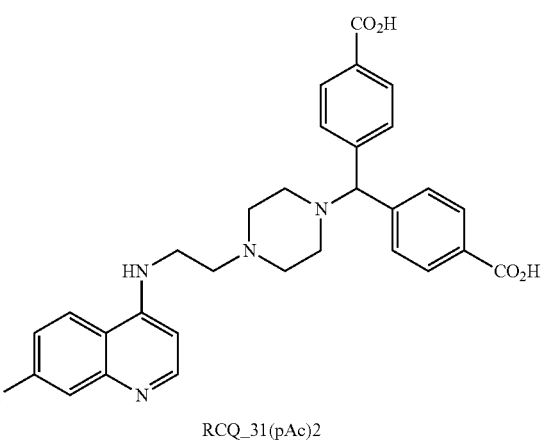

RCQ_31(pAc)2

TABLE 6-continued
Exemplary Piperazine-based RCQ Compounds
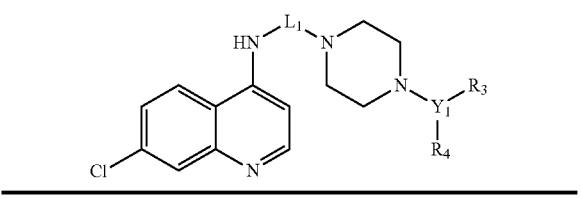
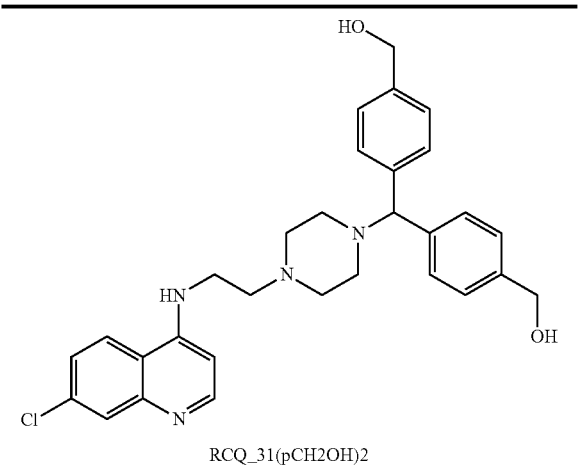
RCQ_31(pCH2OH)2
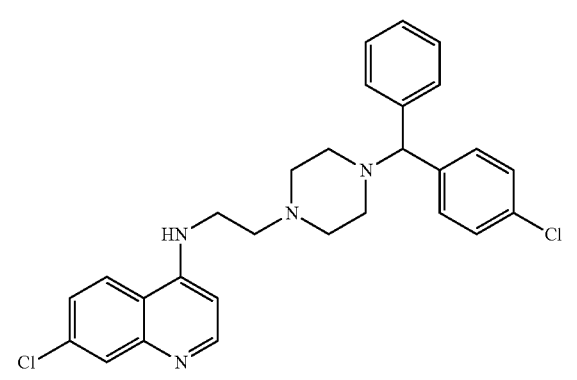
RCQ_32
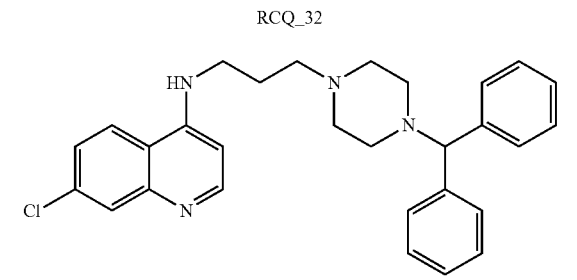
RCQ_34
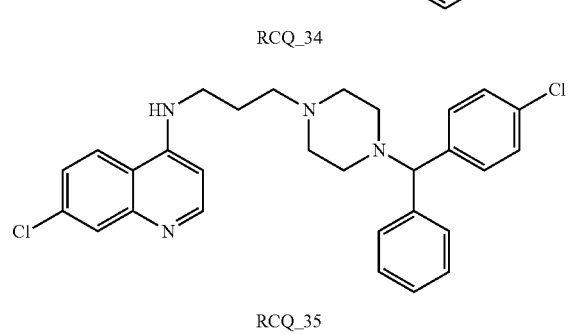
RCQ_35
TABLE 6-continued
Exemplary Piperazine-based RCQ Compounds
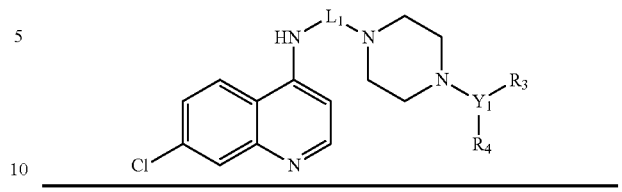
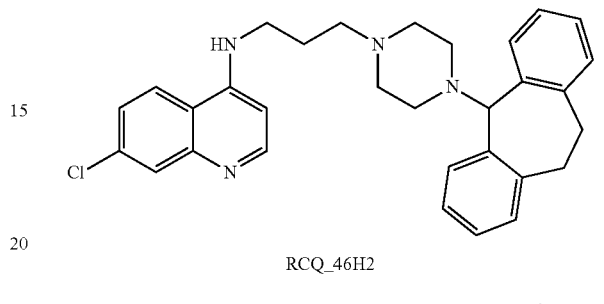
RCQ_46H2
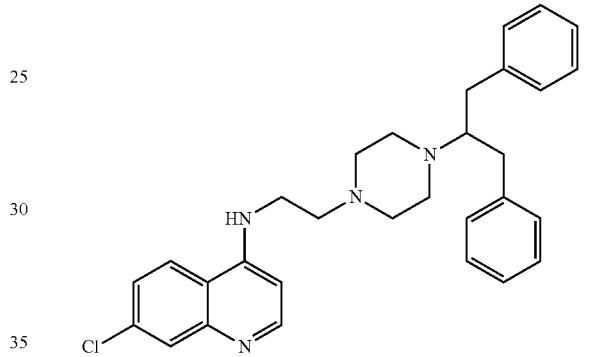
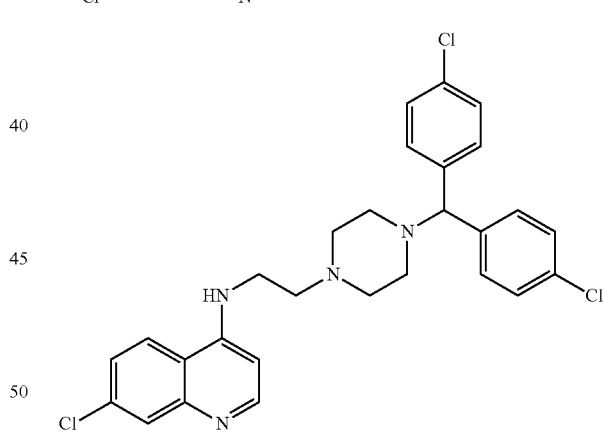
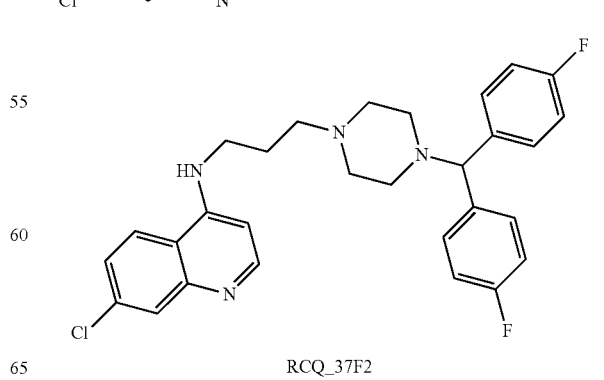
RCQ_37F2

TABLE 6-continued
Exemplary Piperazine-based RCQ Compounds
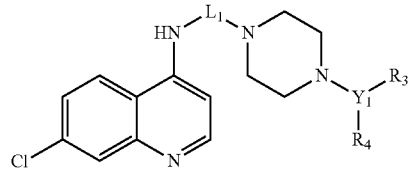
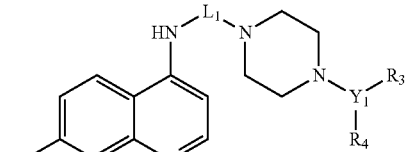
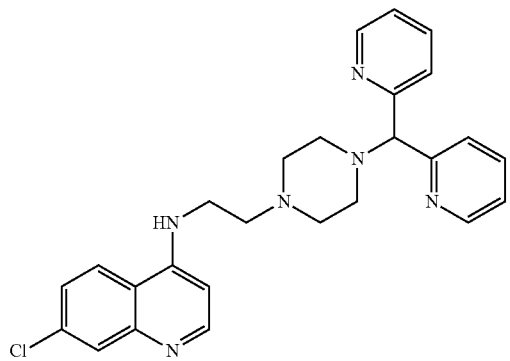
RCQ_31(oP)2
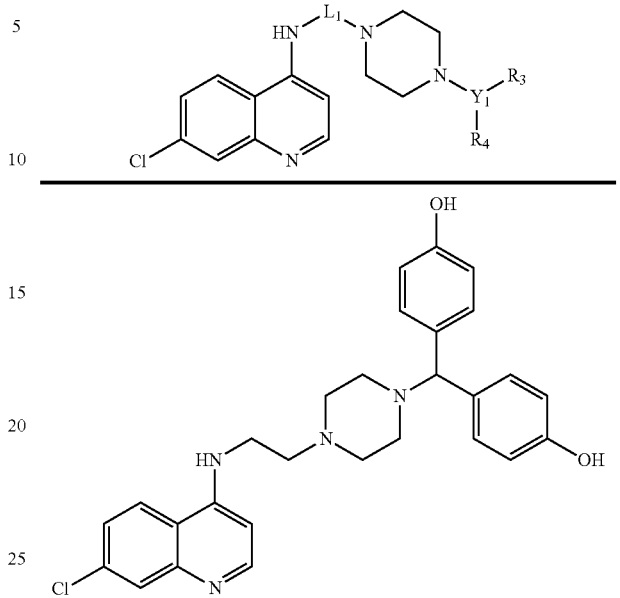
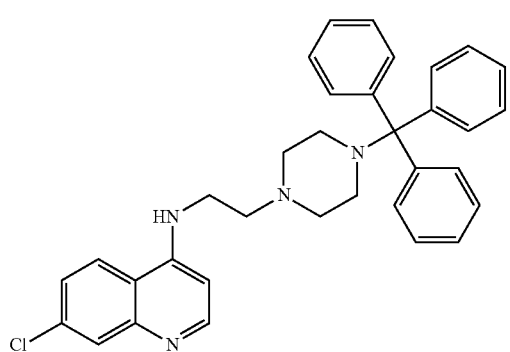 [SMILES: Clc1ccc2c(NCCN3CCN(C(c4ccccc4)(c4ccccc4)c4ccccc4)CC3)ccnc2c1]
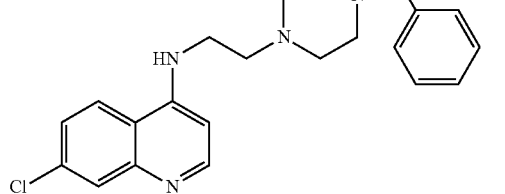
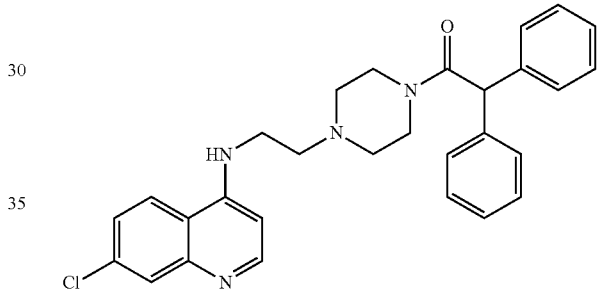
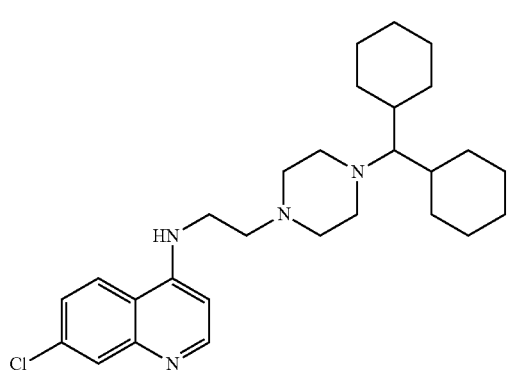 [SMILES: Clc1ccc2c(NCCN3CCN(C(C4CCCCC4)C4CCCCC4)CC3)ccnc2c1]
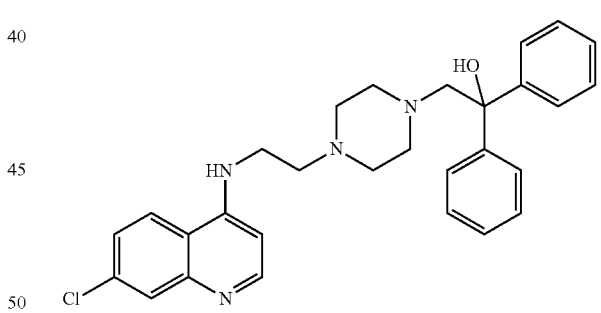
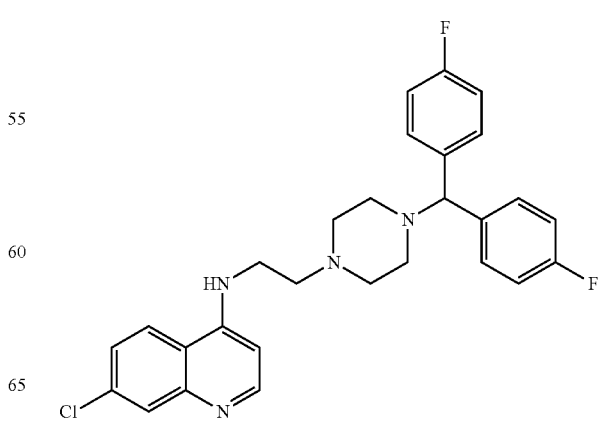

TABLE 6-continued
Exemplary Piperazine-based RCQ Compounds
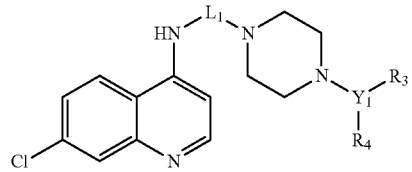
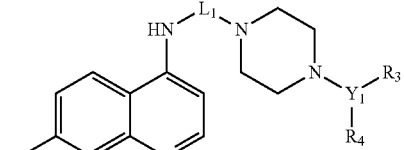
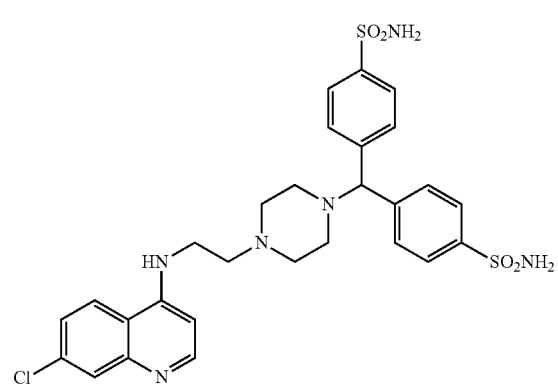 [SMILES: NS(=O)(=O)c1ccc(C(c2ccc(S(N)(=O)=O)cc2)N2CCN(CCNc3ccnc4cc(Cl)ccc34)CC2)cc1]
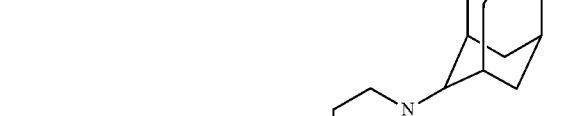
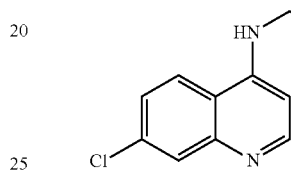
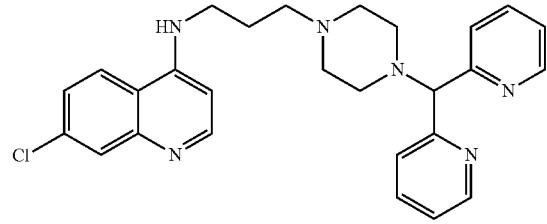 [SMILES: Clc1ccc2c(NCCCN3CCN(C(c4ccccn4)c4ccccn4)CC3)ccnc2c1]
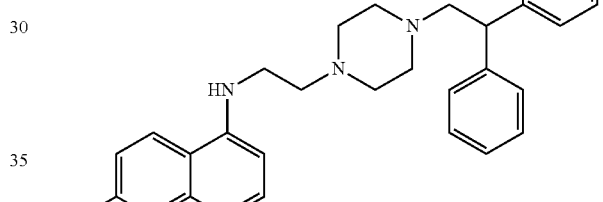
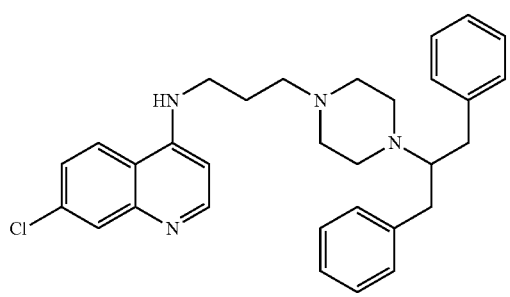 [SMILES: Clc1ccc2c(NCCCN3CCN(C(Cc4ccccc4)Cc4ccccc4)CC3)ccnc2c1]
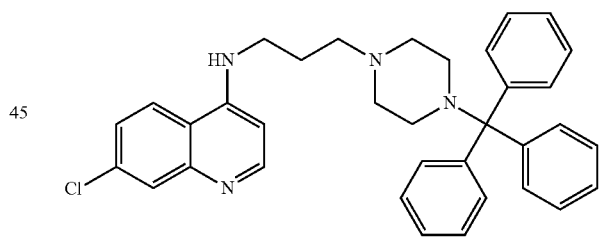
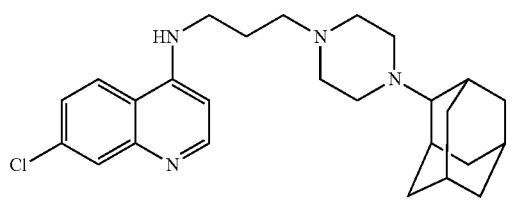 [SMILES: Clc1ccc2c(NCCCN3CCN(C4C5CC6CC(C5)CC4C6)CC3)ccnc2c1]
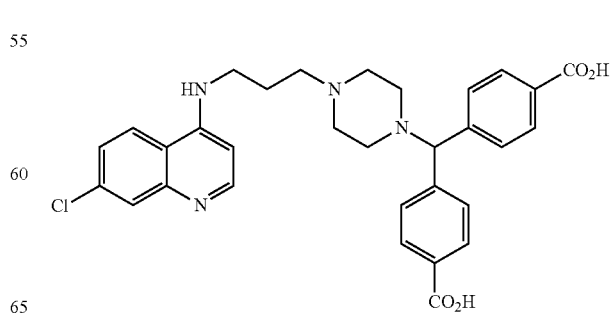

TABLE 6-continued
Exemplary Piperazine-based RCQ Compounds
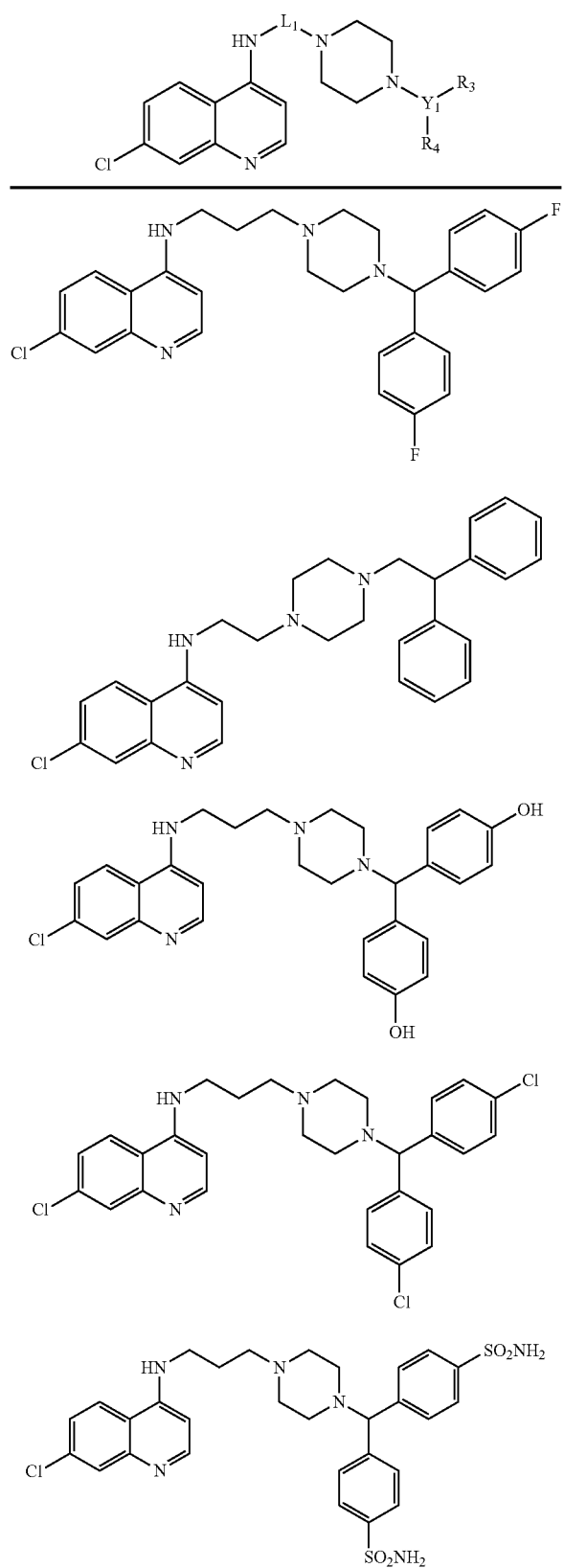
TABLE 6-continued
Exemplary Piperazine-based RCQ Compounds
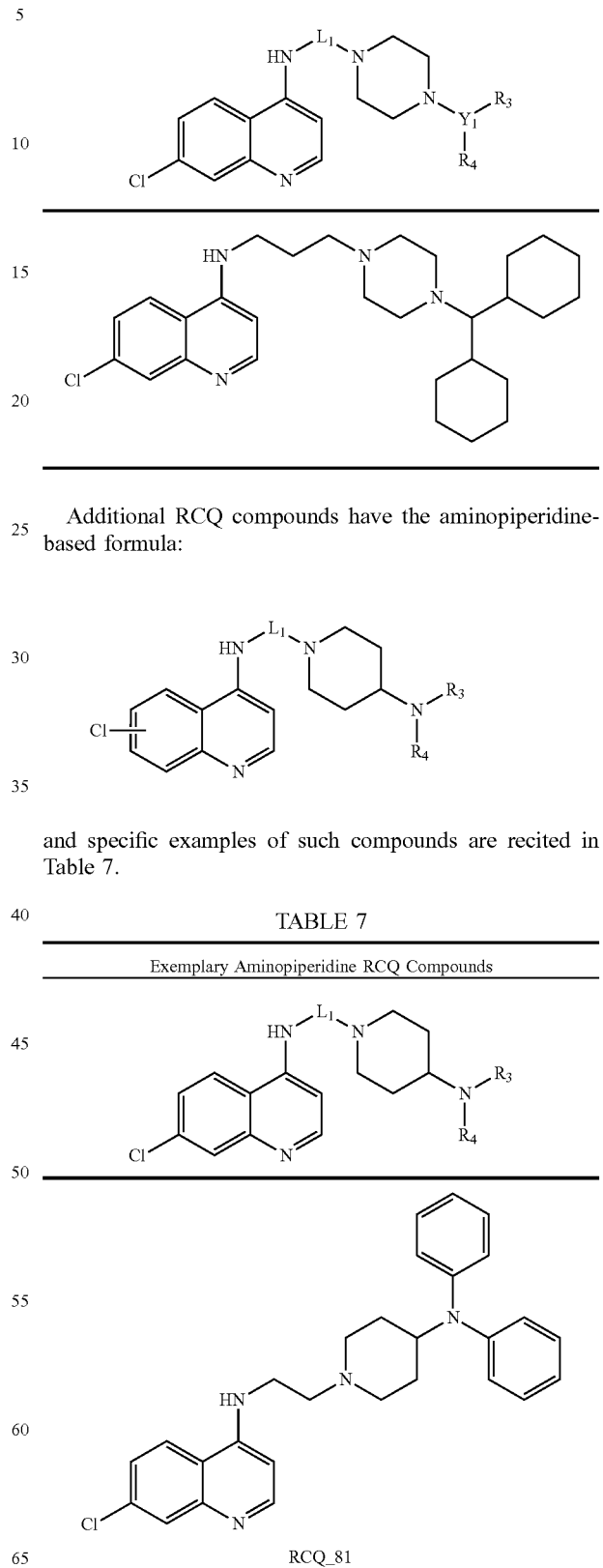
Additional RCQ compounds have the aminopiperidine-based formula:
and specific examples of such compounds are recited in Table 7.
TABLE 7
Exemplary Aminopiperidine RCQ Compounds
RCQ_81

TABLE 7-continued
Exemplary Aminopiperidine RCQ Compounds
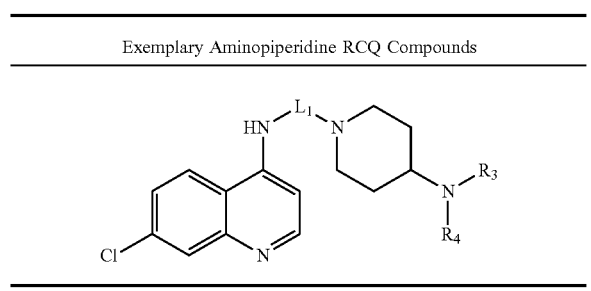
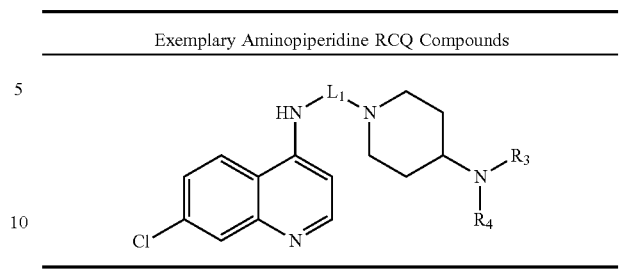
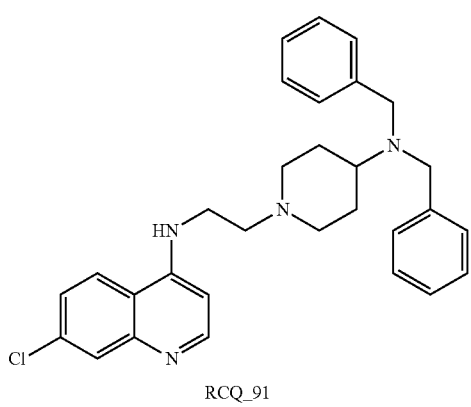 [SMILES: Clc1ccc2c(NCCN3CCC(N(Cc4ccccc4)Cc4ccccc4)CC3)ccnc2c1]
RCQ_91
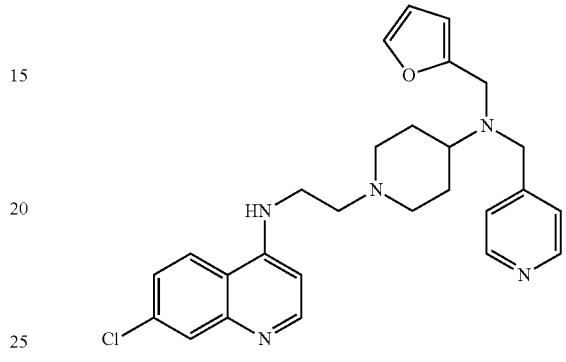
RCQ_91pPfrn
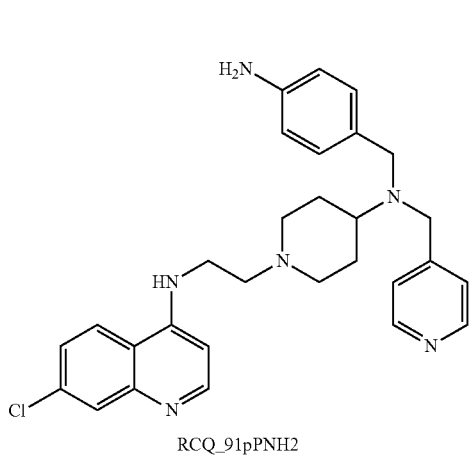 [SMILES: Nc1ccc(CN(Cc2ccncc2)C2CCN(CCNc3ccnc4cc(Cl)ccc34)CC2)cc1]
RCQ_91pPNH2
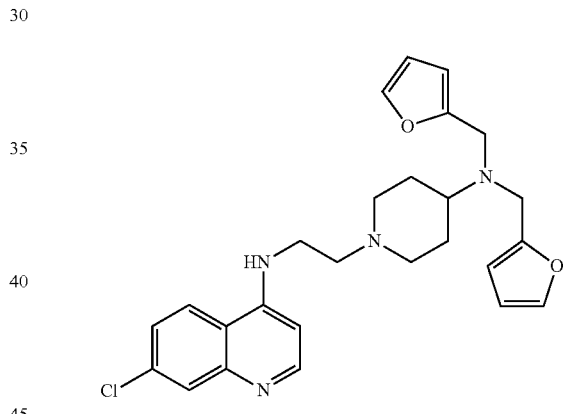
RCQ_91(frn)2
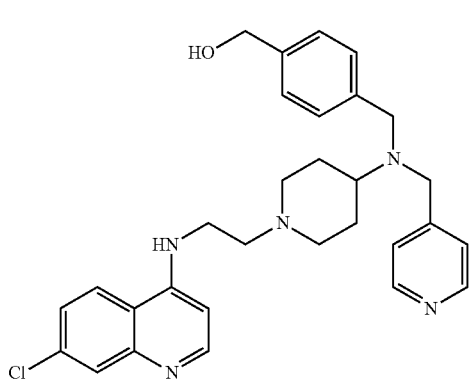
RCQ_91pPCH2OH
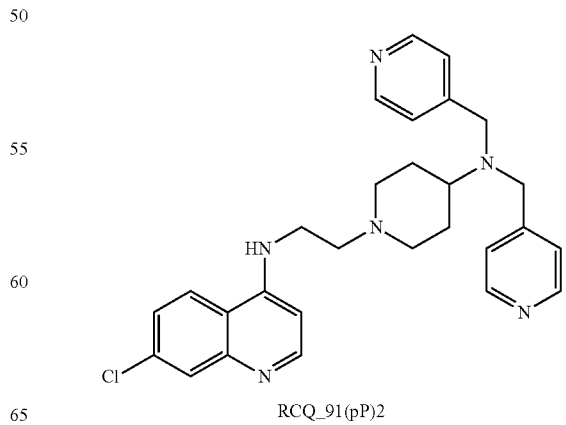
RCQ_91(pP)2

TABLE 7-continued
Exemplary Aminopiperidine RCQ Compounds
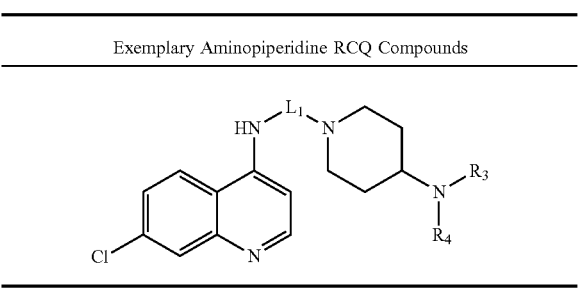
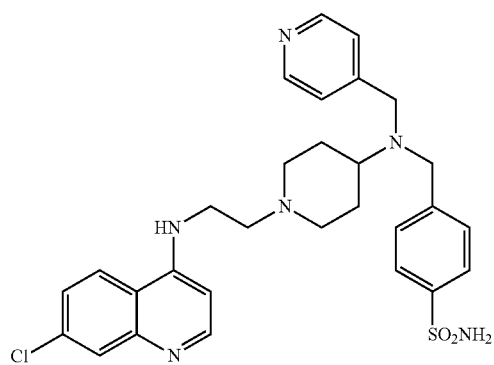
RCQ_91_pNpSA
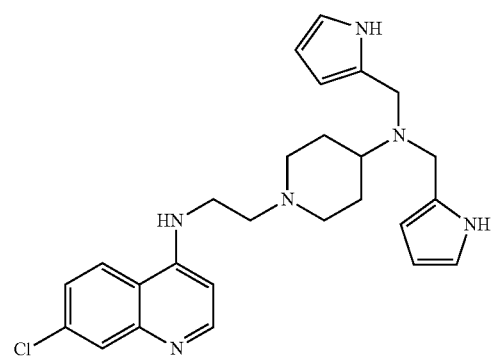 [SMILES: Clc1ccc2c(NCCN3CCC(N(Cc4ccc[nH]4)Cc4ccc[nH]4)CC3)ccnc2c1]
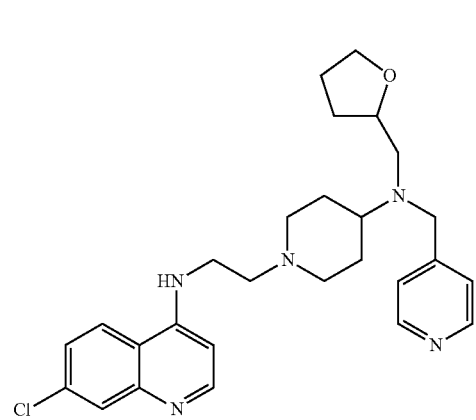 [SMILES: Clc1ccc2c(NCCN3CCC(N(Cc4ccncc4)CC4CCCO4)CC3)ccnc2c1]
TABLE 7-continued
Exemplary Aminopiperidine RCQ Compounds
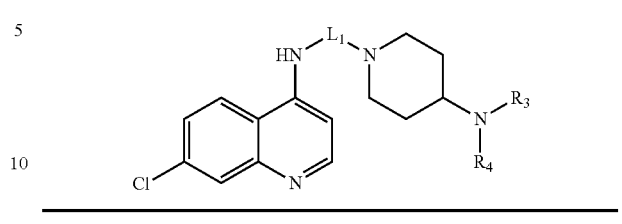
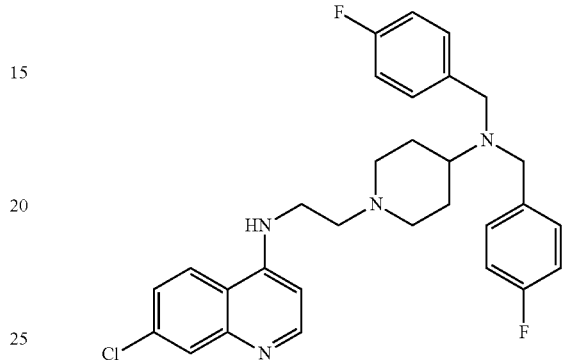
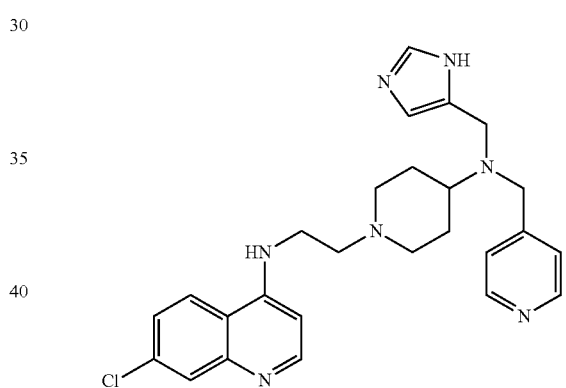
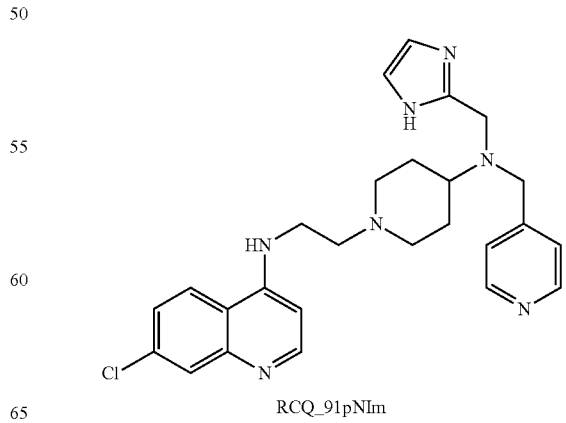
RCQ_91pNIm TABLE 7-continued
Exemplary Aminopiperidine RCQ Compounds
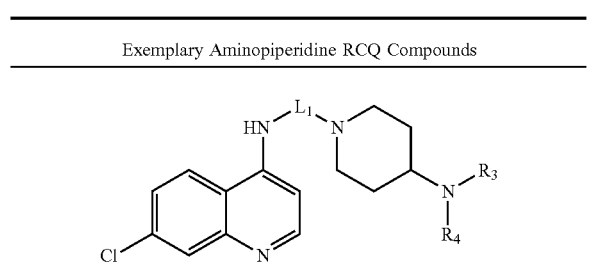
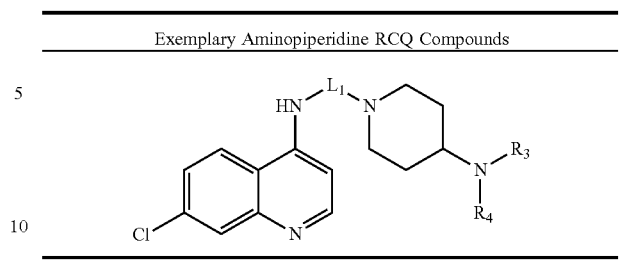
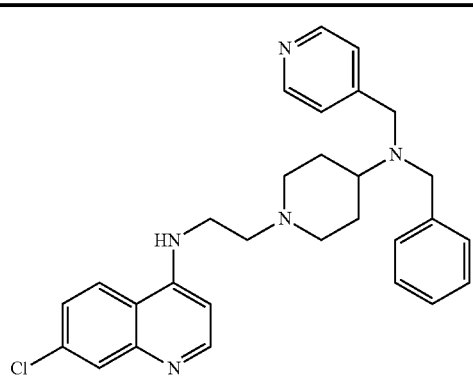
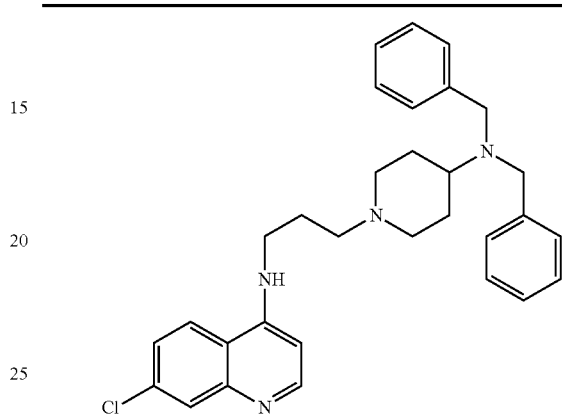
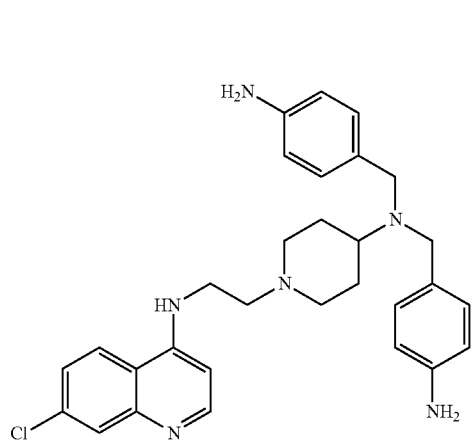
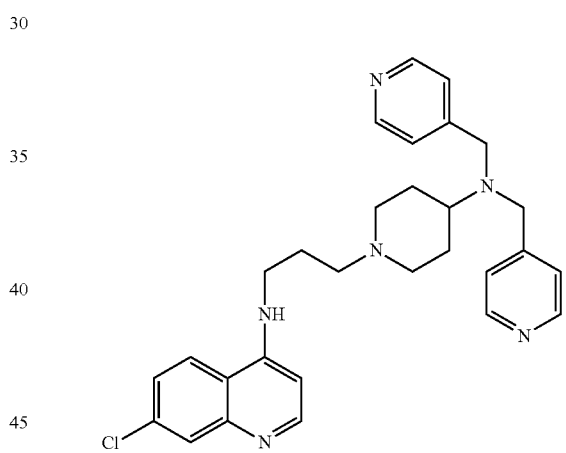
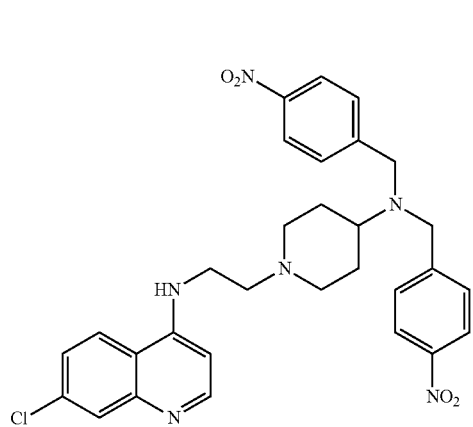 [SMILES: O=[N+]([O-])c1ccc(CN(Cc2ccc([N+](=O)[O-])cc2)C2CCN(CCNc3ccnc4cc(Cl)ccc34)CC2)cc1]
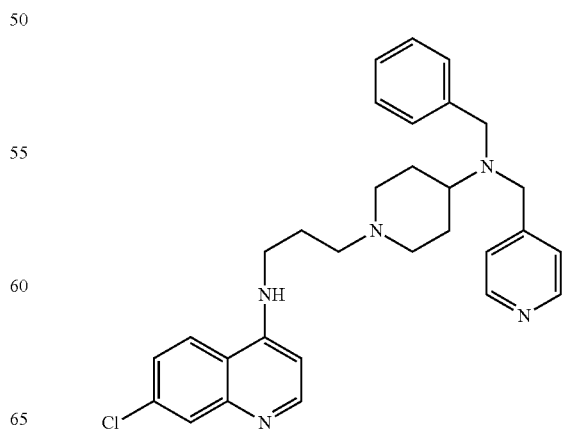

TABLE 7-continued
Exemplary Aminopiperidine RCQ Compounds
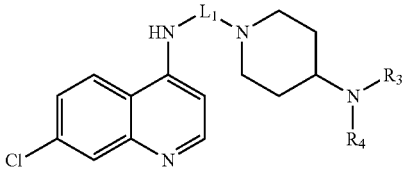
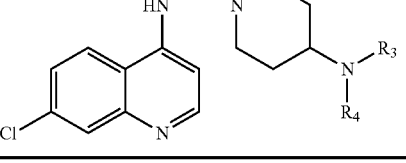
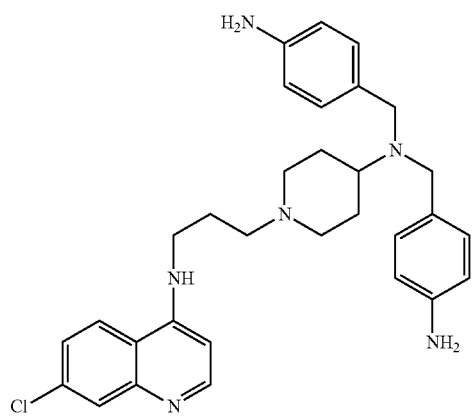
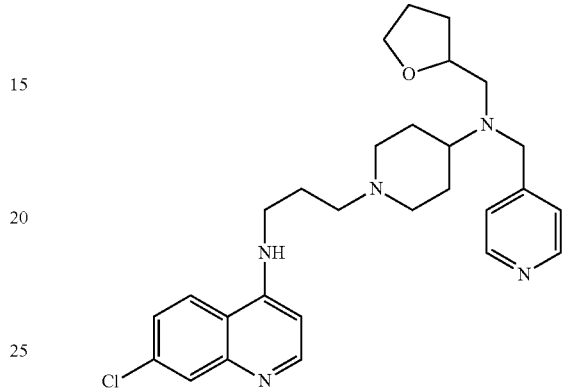
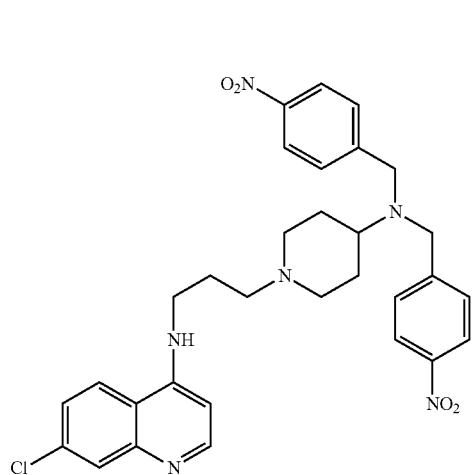 [SMILES: O=[N+]([O-])c1ccc(CN(Cc2ccc([N+](=O)[O-])cc2)C2CCN(CCCNc3ccnc4cc(Cl)ccc34)CC2)cc1]
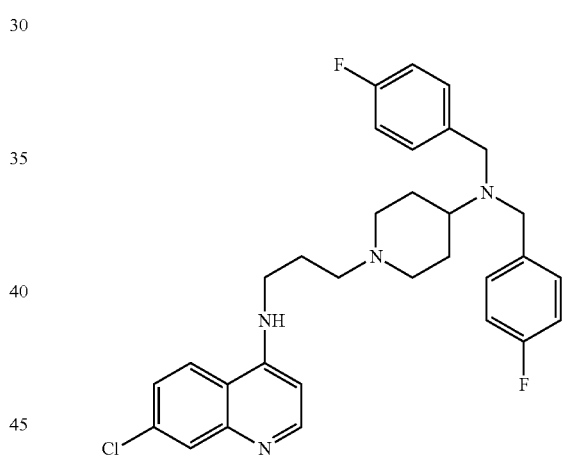
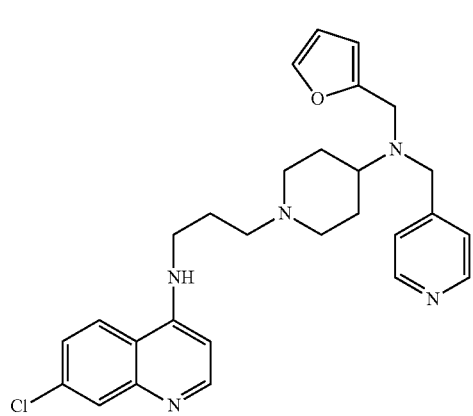 [SMILES: Clc1ccc2c(NCCCN3CCC(N(Cc4ccncc4)Cc4ccco4)CC3)ccnc2c1]
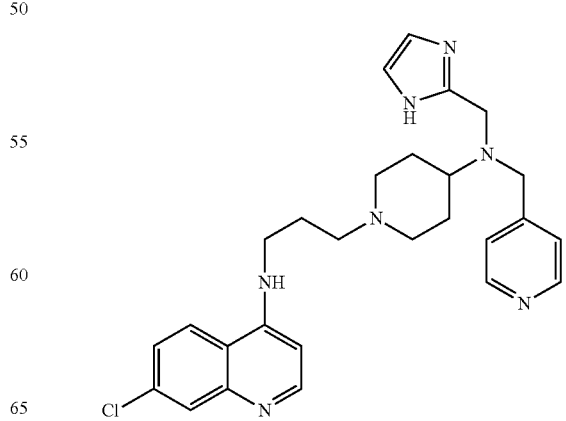

TABLE 7-continued
Exemplary Aminopiperidine RCQ Compounds
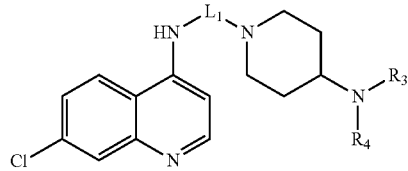
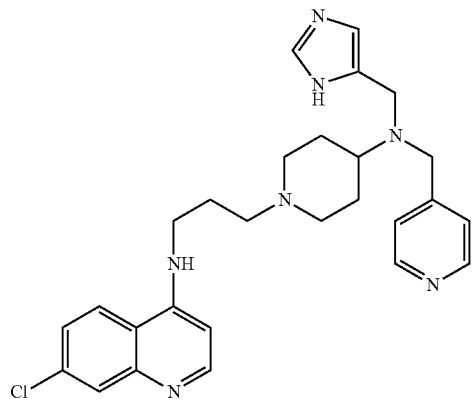 [SMILES: Clc1ccc2c(NCCCN3CCC(N(Cc4ccncc4)Cc4cnc[nH]4)CC3)ccnc2c1]
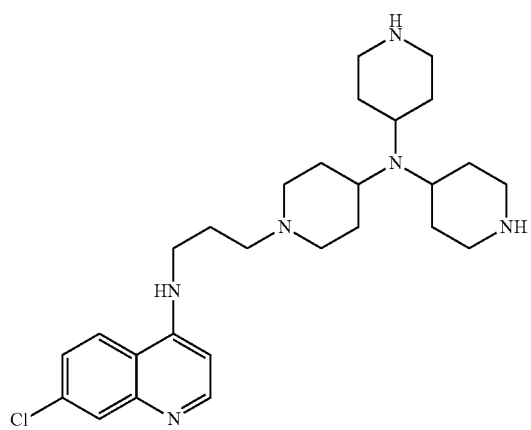 [SMILES: Clc1ccc2c(NCCCN3CCC(N(C4CCNCC4)C4CCNCC4)CC3)ccnc2c1]
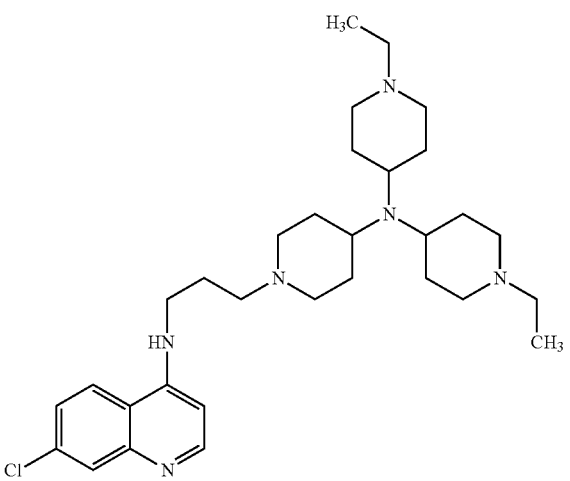 [SMILES: CCN1CCC(N(C2CCN(CC)CC2)C2CCN(CCCNc3ccnc4cc(Cl)ccc34)CC2)CC1]
Additional RCQ compounds have a diazapane-based formula:
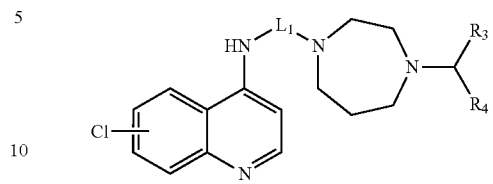
and specific examples of such compounds are recited in Table 8.
TABLE 8
Exemplary Diazapane RCQ Compounds
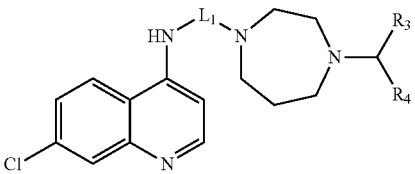
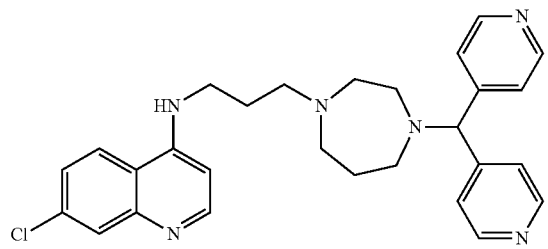
RCQ_35(pP)2
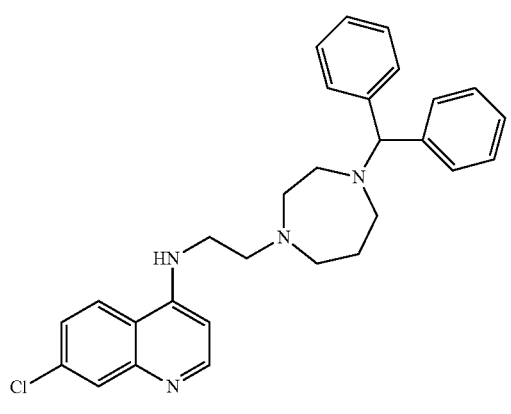
RCQ_36

TABLE 8-continued

Exemplary Diazapane RCQ Compounds

RCQ_72

RCQ_73

RCQ_74

RCQ_76

TABLE 9

Exemplary Pyrrolidine RCQ Compounds

RCQ_151
(a WR268954 derivative)

Also disclosed herein are compounds having a cyclic linker group linking the quinoline derivative and the reversal agent moiety. Such compounds can have the formula wherein $R_1$ and L, together form a cyclic group. Examples of such compounds can conform to the chemical structure:

wherein the variable groups are as set forth above. Particular examples of such compounds have the structures recited in Table 10.
TABLE 10
Exemplary RCQ Compounds Having a Cyclic Linker
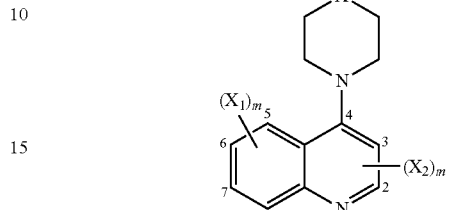
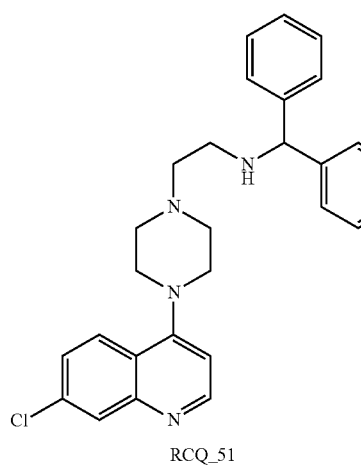
RCQ_51
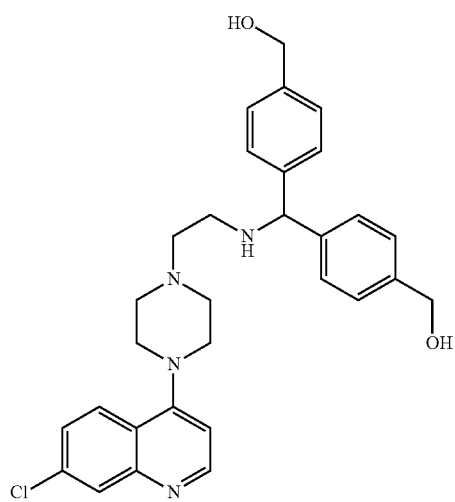
RCQ_51(pCH2OH)2
TABLE 10-continued
Exemplary RCQ Compounds Having a Cyclic Linker
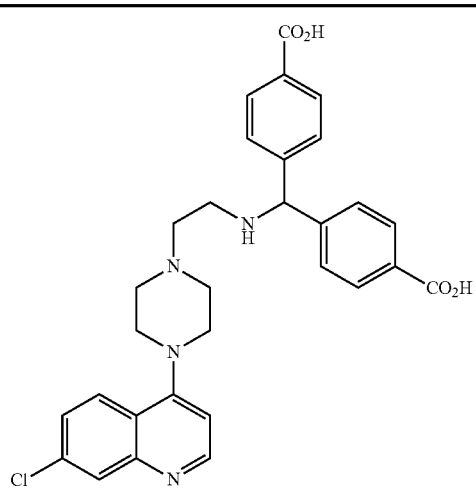
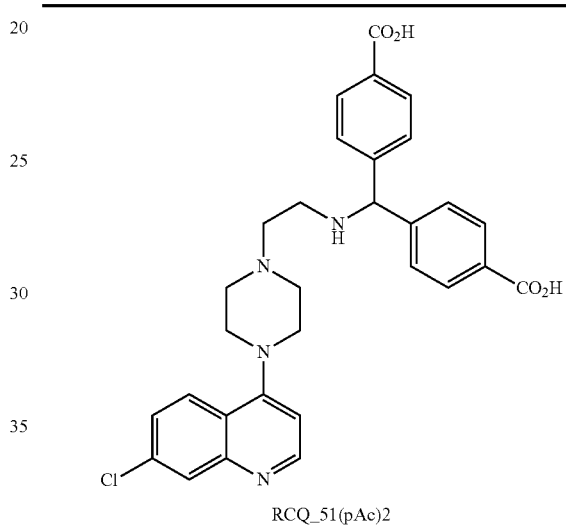
RCQ_51(pAc)2
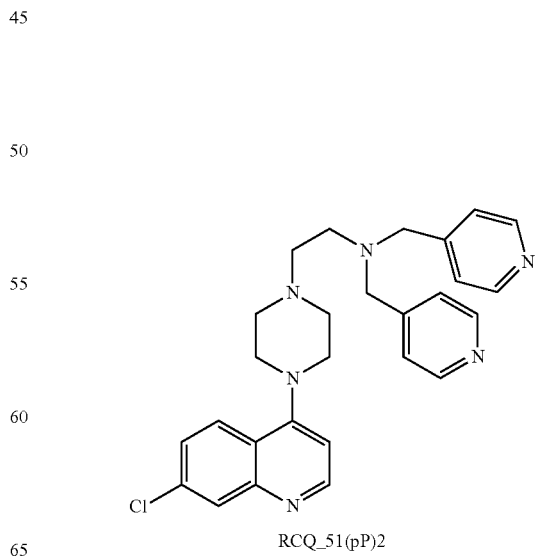
RCQ_51(pP)2

TABLE 10-continued
Exemplary RCQ Compounds Having a Cyclic Linker
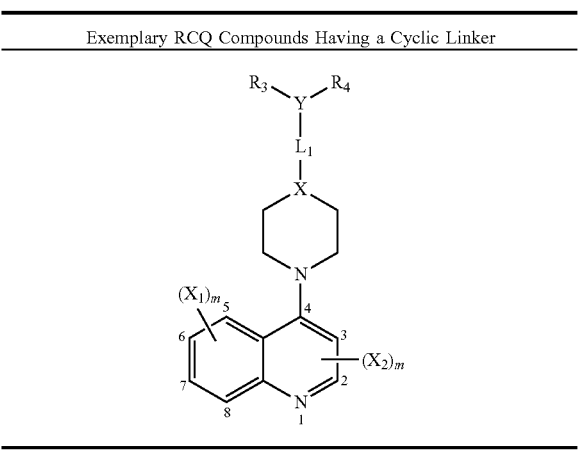
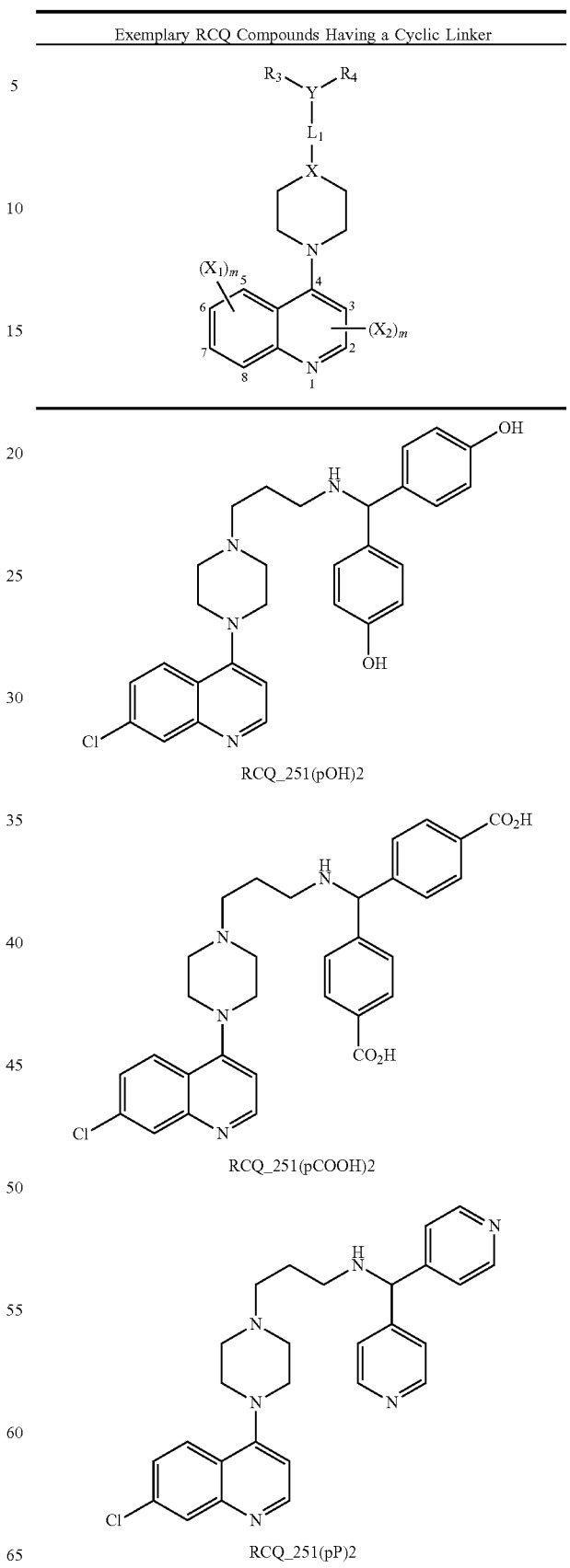

TABLE 10-continued
Exemplary RCQ Compounds Having a Cyclic Linker
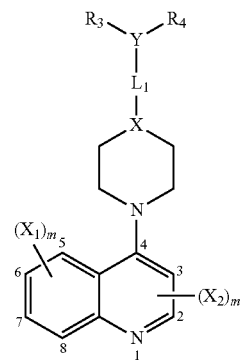
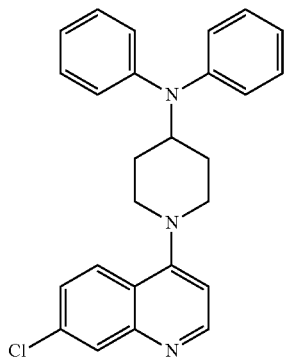
RCQ_261
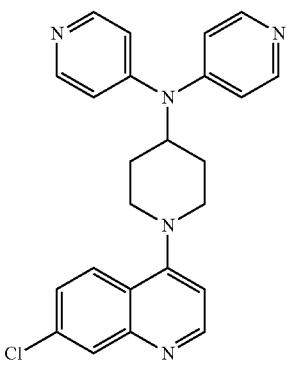
RCQ_261(pP)2
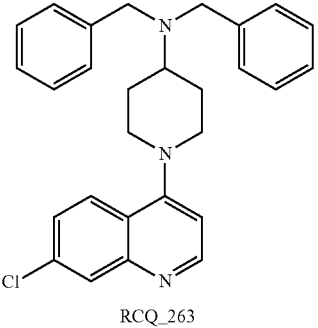 [SMILES: Clc1ccc2c(N3CCC(N(Cc4ccccc4)Cc4ccccc4)CC3)ccnc2c1]
RCQ_263
TABLE 10-continued
Exemplary RCQ Compounds Having a Cyclic Linker
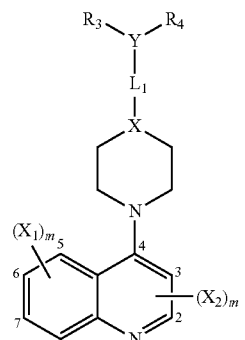
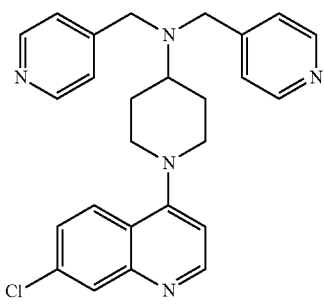
RCQ_263(pP)2
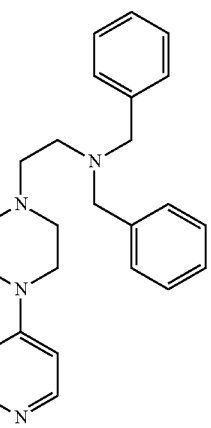
RCQ_351

TABLE 10-continued

Exemplary RCQ Compounds Having a Cyclic Linker

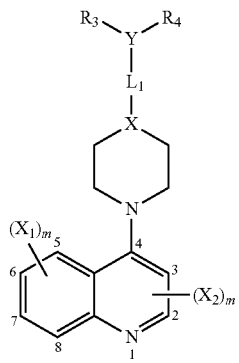

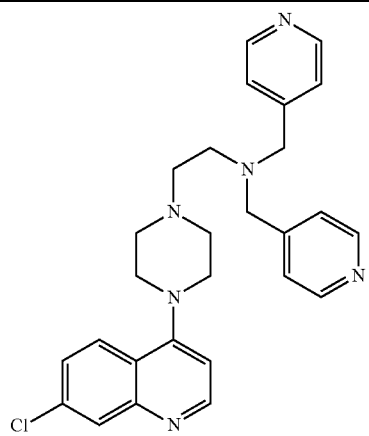

RCQ_351(pP)2

B. Additional RCQ Compounds

In some embodiments, an RCQ compound includes a quinoline analog (such as choloroquine) covalently linked to a $CQ^R$ reversal moiety. Typically, a quinoline analog in a disclosed RCQ compound has a $C_4$ substitution, where the $C_4$ substituent (or a modified form thereof) can be used to covalently link a $CQ^R$ reversal moiety to the quinoline-analog core. Exemplary $C_4$ substituents include, for example, alkylamino, alkylhalo (such as alkylchloro), alkoxy, or thioalkyl. Others have chemically modified the CQ molecular framework and found that the $C_4$ side chain can be modified without substantial loss of in vitro antimalarial efficacy (De et al., *J. Med. Chem.*, 41(25):4918-4926, 1998; Egan et al., *J. Med. Chem.*, 43(2):283-291, 2000); thus, it is believed that a wide range of linkers between a quinoline analog (such as CQ) and a $CQ^R$ reversal moiety can be used with minimal impact on the antimalarial efficacy of an RCQ. In addition, the chiral methyl of the CQ alkylamino side chain is known to be unnecessary for action against malaria (De et al., *J. Med. Chem.*, 41(25):4918-4926, 1998; De et al., *Am. J. Trop. Med. Hyg.*, 55(6):579-583, 1996); thus, in particular examples, RCQ molecules do not have any chiral centers. Advantageously, production of non-chiral RCQ molecules may be more cost effective than production of chiral molecules, which may further the goal of providing low-cost drugs for malaria treatment (especially in impoverished countries).

A quinoline analog as envisioned herein also can be substituted at other carbons of the quinoline ring system. In some examples, a quinoline analog is a quinoline ring substituted at $C_6$, $C_7$, or $C_8$, or combinations thereof, with, for example, halo, alkylhalo (such as trifluoromethyl), amino, alkylamino, or hydroxyl substitutents. In particular examples, quinoline analogs include, for instance, chloroquine, 7-chloroquinoline, 8-aminoquinoline, amodiaquine, primaquine, 7-(trifluoromethyl)quinoline, or 6-(trifluoromethyl)chloroquine, 6,7-dichloroquinoline, and as illustrated in the foregoing chemical formulas.

$CQ^R$ reversal agents suitable for incorporation as, for example "G" in the general structures presented above, are known in the art (e.g., Bhattacharjee et al., *J. Chem. Inf. Comput. Sci.*, 42:1212-1220, 2002; Guan et al., *J. Med. Chem.*, 45(13):2741-2748, 2002). $CQ^R$ reversal agents cause $CQ^R$ *Plasmodium* sp. strains (such as *P. falciparum* $CQ^R$ strains) to revert to CQ sensitivity. An exemplary pharmacophore for a $CQ^R$ reversal agent has recently been identified (e.g., Bhattacharjee et al., *J. Chem. Inf. Comput. Sci.*, 42:1212-1220, 2002). This representative pharmacophore is characterized by two hydrophobic groups (such as aromatic rings or fused ring systems) located somewhat near each other and an aliphatic chain terminated by a base (Bhattacharjee et al., *Antimicrob. Agents Chemother.*, 45(9):2655-2657, 2001; Bhattacharjee et al., *J. Chem. Inf. Comput. Sci.*, 42(5):1212-1220, 2002). Without being limited to one theory, $CQ^R$ reversal agents are believed to exert their biological effect, at least in part, by decreasing the efflux of CQ (or CQ-like drugs) from the plasmodial DV, which efflux is thought to be mediated by a membrane pump (e.g., PfCRT; see, Zhang et al., *Biochem.*, 43(26):8290-8296, 2004; Bennett et al., *Mol. Biochem. Parasitol.*, 133(1):99-114, 2004; Martin and Kirk, *Mol. Biol. Evol.*, 21(10):1938-1949, 2004). $CQ^R$ reversal agents are not thought to have a CQ-independent toxic effect on plasmodial parasites. Exemplary reversal agents include, without limitation, amitriptyline, amlodipine, azatadine, chlorpheniramine, citalopram, cyclosporine, cyproheptadine, cyproheptadine, desipramine, dibenzosuberanylpiperazine derivatives (Osa et al., *J. Med. Chem.*, 46(10):1948-1956, 2003), diethyl-{3-[3-(4-methoxy-benzylidene)-pyrrolidin-1-yl]-propyl}-amine, erythromycin, fantofarone (Adovelande et al., *J. Biochem. Pharmacol.*, 55(4):433-440, 1998), fluoxetine, haloperidol, icajine, imipramine, isorentuline, ivermectin, ketotefin, ketotifen, nomifensine, nonylphenolethoxylates (including, e.g., NP30: $C_9H_{19}$-Phenyl-(O—$CH_2CH_2)_{30}$OH; Crandall et al., *Antimicrob. Agents Chemother.*, 44(9):2431-2434, 2000), oxaprotiline, probenecid, progesterone, promethazine, strychnobrasiline, BG958 (a 9,10-dihydroethanoanthracene derivative; Millet et al., *Antimicrob. Agents Chemother.*, 48(12):4869-4872, 2004), trifluoperazine, verapamil, and WR 268954 (De et al., *Am. J. Trop. Med. Hyg.*, 49(1):113-120, 1993).

A $CQ^R$ reversal moiety as described throughout the specification includes any known $CQ^R$ reversal agent or derivative thereof that retains $CQ^R$ reversal function, or any chemical structure that satisfies a $CQ^R$ reversal agent pharmacophore (such as the Bhattacharjee et al. pharmacophore described above) and confers $CQ^R$ reversal function. As discussed above, $CQ^R$ reversal function is the ability of a compound (or moiety) to sensitize at least one $CQ^R$ *Plasmodium* sp. strain to CQ. A $CQ^R$ *Plasmodium* sp. strain is sensitized to CQ if a combination of CQ and a $CQ^R$ reversal agent/moiety (or in the presence of a RCQ) inhibits parasite growth as compared to parasite growth in the presence of CQ alone. For example, parasite growth in the presence of a combination of CQ and a $CQ^R$ reversal agent/moiety (or in the presence of a RCQ) may be at least about 10%, at least about 25%, at least about 40%, at least about 50%, at least about 75%, at least about 80%, at least about 90%, or at least about 95% less than parasite growth in the presence of CQ only.

A quinoline analog (such as chloroquine) can be covalently linked to a $CQ^R$ reversal agent moiety via commonly known chemical syntheses. Several chemical syntheses useful for such purposes are described throughout this specification. In one example, the $C_4$ side chain of a quinoline analog (such as CQ) may contain (or be modified to contain) a leaving group (such as a leaving group located at the terminus of the $C_4$ side chain). A leaving group, as is well known in the art, is an atom or group capable of being displaced by a nucleophile. Suitable leaving groups include halogen, alkanesulfonyloxy, arenesulfonyloxy, ester, or amino; more particular non-limiting examples of leaving groups are chloro, bromo, iodo, mesyloxy, tosyloxy, trifluorosulfonyloxy, methoxy, N,O-dimethylhydroxylamino, and the like. When reacted with a $CQ^R$ reversal agent having an aliphatic chain terminated by a base (which acts as a nucleophile under the reaction conditions), the basic residue (e.g., a nitrogen) of the reversal agent is substituted for the leaving group by a commonly known nucleophilic substitution ($S_N2$) reaction to form a quinoline analog covalently linked to the $CQ^R$ reversal agent (see, e.g., Loudon, *Organic Chemistry*, Fourth Edition, New York:Oxford University Press, 2002, pp. 360-361, 1084-1085). Conversely, the terminal base of the $CQ^R$ reversal agent can be modified to a leaving group, and the $C_4$ side chain of a quinoline analog (such as CQ) may contain (or be modified to contain) an nucleophile (such as an amine, alkoxide, or enolate). In this latter example, the nucleophile present on the $C_4$ side chain of the quinoline analog can be substituted (via $S_N2$ reaction) for the leaving group on the $CQ^R$ reversal agent (see, e.g., Loudon, *Organic Chemistry*, Fourth Edition, New York: Oxford University Press, 2002, pp. 360-361, 1084-1085); thereby, forming the combined RCQ molecule.

Non-limiting representative RCQs having a quinoline analog (such as chloroquine) covalently linked to a $CQ^R$ reversal agent moiety include N-(7-chloro-quinolin-4-yl)-N'-(2-phenothiazin-10-yl-ethyl-propane-1,3-diamine (a promethazine derivative; see RCQ_100); N-[3-(4-chloro-phenyl)-3-pyridin-2-yl-propyl]-N'-(7-chloro-quinolin-4-yl)-N-methyl-propane-1,3-diamine (a chlorpheniramine derivative; see RCQ_101); N-(7-chloro-quinolin-4-yl)-N'-[4-phenyl-4-(4-trifluoromethyl-phenoxy-butyl]-propane-1, 3-diamine (a fluoxetine derivative; see RCQ_103); (7-chloro-quinolin-4-yl)-[3-(4-dibenzo[a,d]cyclohepten-5-ylidene-piperidin-1-yl)-propyl]-amine (a cyproheptadine derivative; see RCQ_110); 5-{1-[3-(7-chloro-quinolin-4-ylamino)-propyl]-piperidin-4-ylidene}-5,11-dihydro-dibenzo[a,d]cyclohepten-10-one (a ketotifen derivative; see RCQ_111); and (7-chloro-quinolin-4-yl)-{3-[4-(5,6-dihydro-benzo[5,6]cyclohepta[1,2-b]pyridin-11-ylidene)-piperidin-1-yl]-propyl}-amine (a azatadine derivative; see RCQ_112); 5-{{2-[3-(7-Chloro-quinolin-4-ylamino)-propylamino]-ethyl}-[2-(3,4-dimethoxy-phenyl)-ethyl]-amino}-2-(3,4-dimethoxy-phenyl)-2-isopropyl-pentanenitrile (a verapamil derivative; see RCQ_150); N-(7-Chloro-quinolin-4-yl)-N'-[2-(ethyl-{3-[3-(4-methoxy-benzyl)-pyrrolidin-1-yl]-propyl}-amino)-ethyl]-propane-1,3-diamine (a WR268954 derivative; see RCQ_151).

C. Methods of RCQ Synthesis

The disclosed RCQ compounds can be synthesized by any method known in the art. Many general references providing commonly known chemical synthetic schemes and conditions useful for synthesizing the disclosed compounds are available (see, e.g., Smith and March, March's *Advanced Organic Chemistry: Reactions, Mechanisms, and Structure*, Fifth Edition, Wiley-Interscience, 2001; or Vogel, *A Textbook of Practical Organic Chemistry, Including Qualitative Organic Analysis*, Fourth Edition, New York:Longman, 1978).

Compounds as described herein may be purified by any of the means known in the art, including chromatographic means, such as HPLC, preparative thin layer chromatography, flash column chromatography and ion exchange chromatography. Any suitable stationary phase can be used, including normal and reversed phases as well as ionic resins. Most typically the disclosed compounds are purified via silica gel and/or alumina chromatography. See, e.g., *Introduction to Modern Liquid Chromatography*, 2nd Edition, ed. L. R. Snyder and J. J. Kirkland, John Wiley and Sons, 1979; and *Thin Layer Chromatography*, ed E. Stahl, Springer-Verlag, New York, 1969.

Suitable exemplary syntheses of RCQ compounds are provided below:

1. One Method for Synthesis of RCQ_02 and Structurally Related RCQs

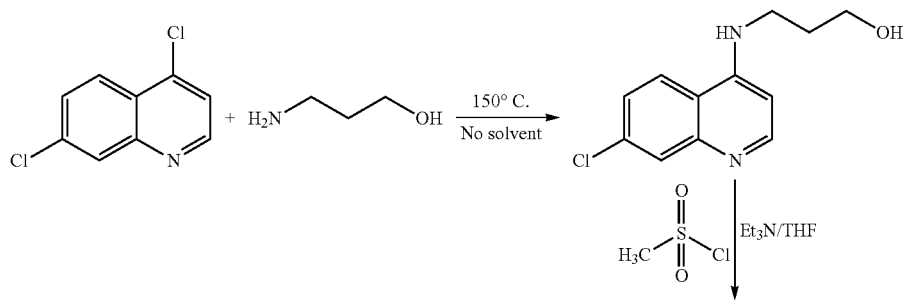

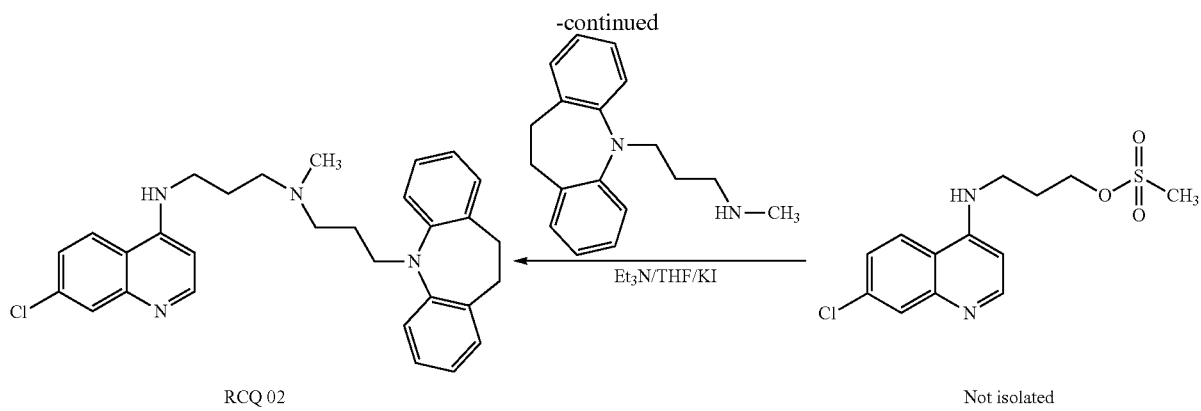

RCQ 02   Not isolated

2. Representative Nucleophilic Substitution ($S_N2$) Reaction

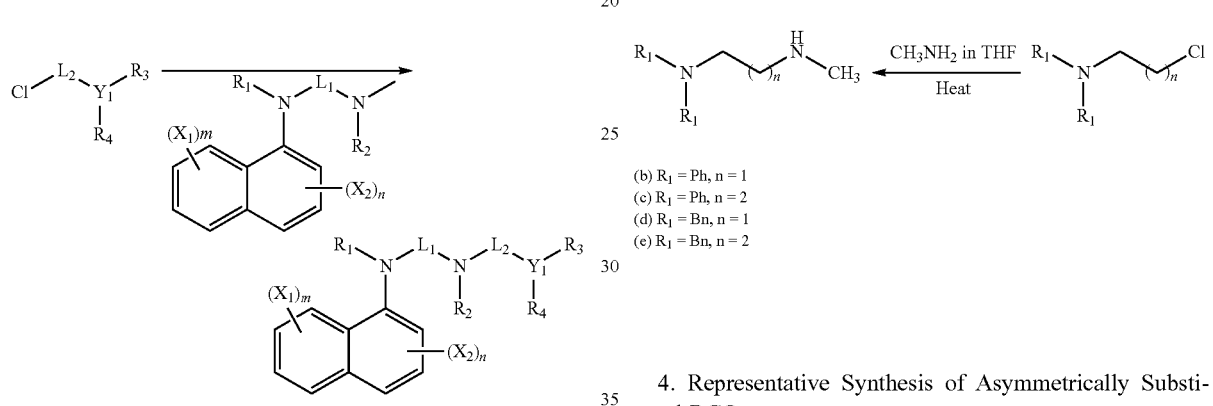

(b) $R_1$ = Ph, n = 1
(c) $R_1$ = Ph, n = 2
(d) $R_1$ = Bn, n = 1
(e) $R_1$ = Bn, n = 2

3. Exemplary Synthesis of Intermediates Useful for RCQ Synthesis

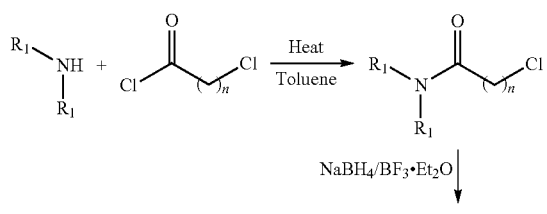

4. Representative Synthesis of Asymmetrically Substituted RCQs

Schemes 4 and 5 demonstrate how even unsymmetrical aralkyl amines can be prepared. This method is exceedingly flexible ($Ar^1$ and $Ar^2$ may be derived from a variety of aryl groups as described above, including, without limitation phenyl groups, pyridines, furans, imidazoles, etc.). These syntheses are amenable to execution via parallel synthesis in a carousel reactor. As will be apparent to those of skill in the art upon consideration of Schemes 4 and 5, certain functional groups may require protection during the synthesis (e.g., carboxyl groups as esters, which can be hydrolyzed to acids, or reduced to alcohols).

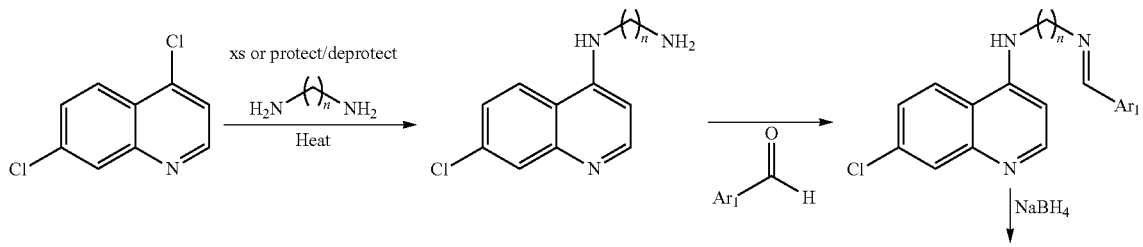

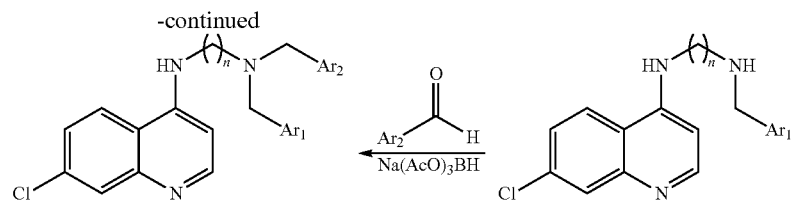
Ar1, Ar2 = Any aromatic ring
n = 2-6
5. Second Representative Synthesis of Asymmetrically Substituted RCQs
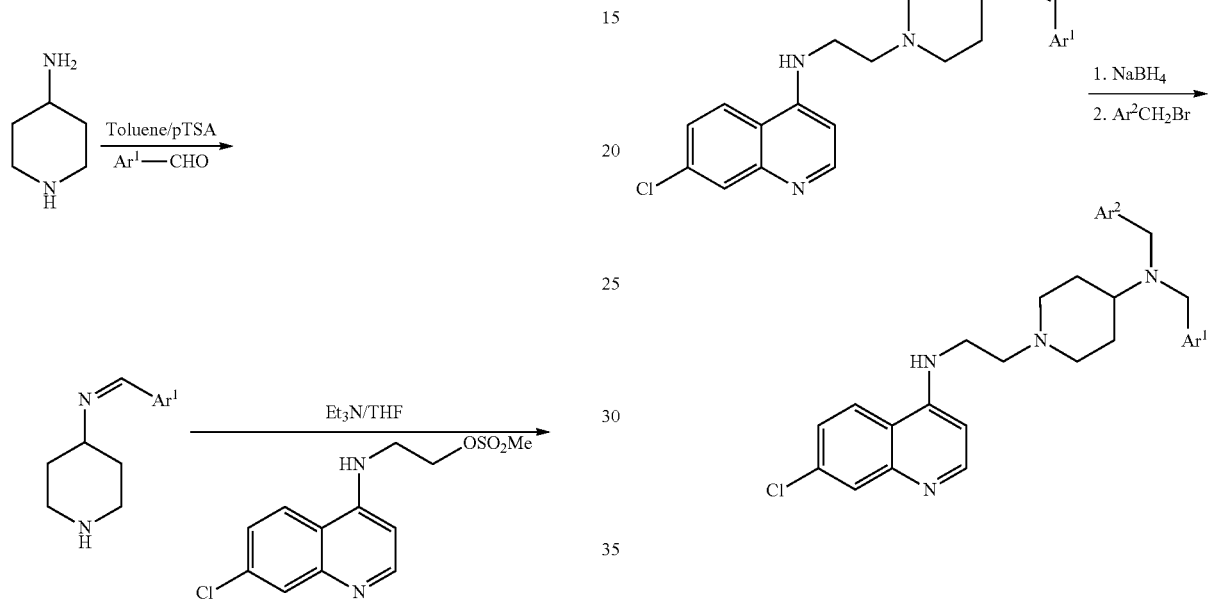
6. Synthesis of Hydrophilic RCQs
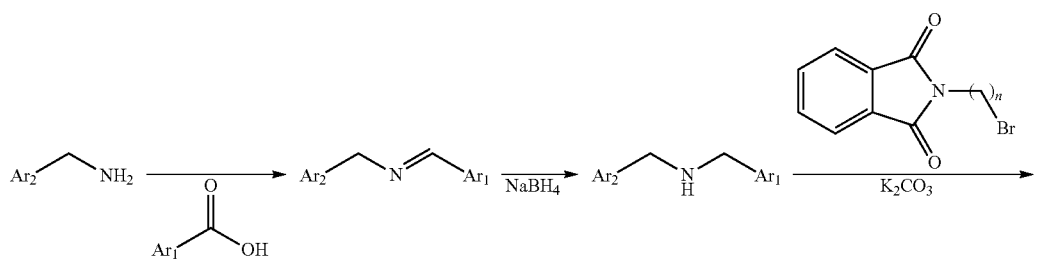
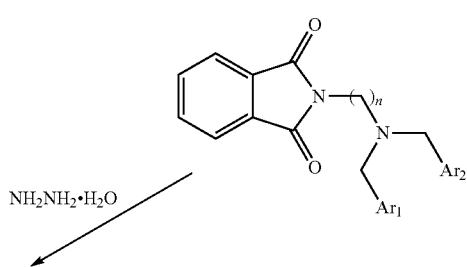

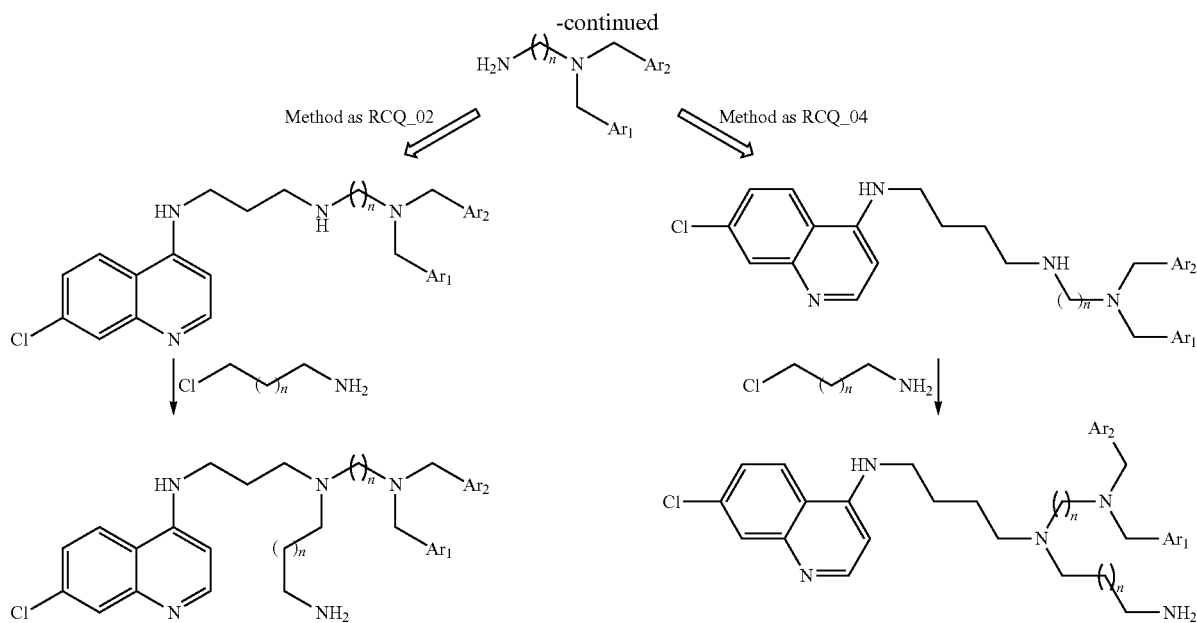

7. General Synthesis of Tetrasubstituted Ethylene-Based RCQ Compounds

Tetrasubstituted ethylene-based compounds, including those illustrated in Table 4, can be prepared according to the following general method. As is known to those of skill in the art the desired tetrasubstituted ethylene compound can be prepared by selecting the appropriate ketone starting material. Examples of suitable ketones include, without limitation, those illustrated below.

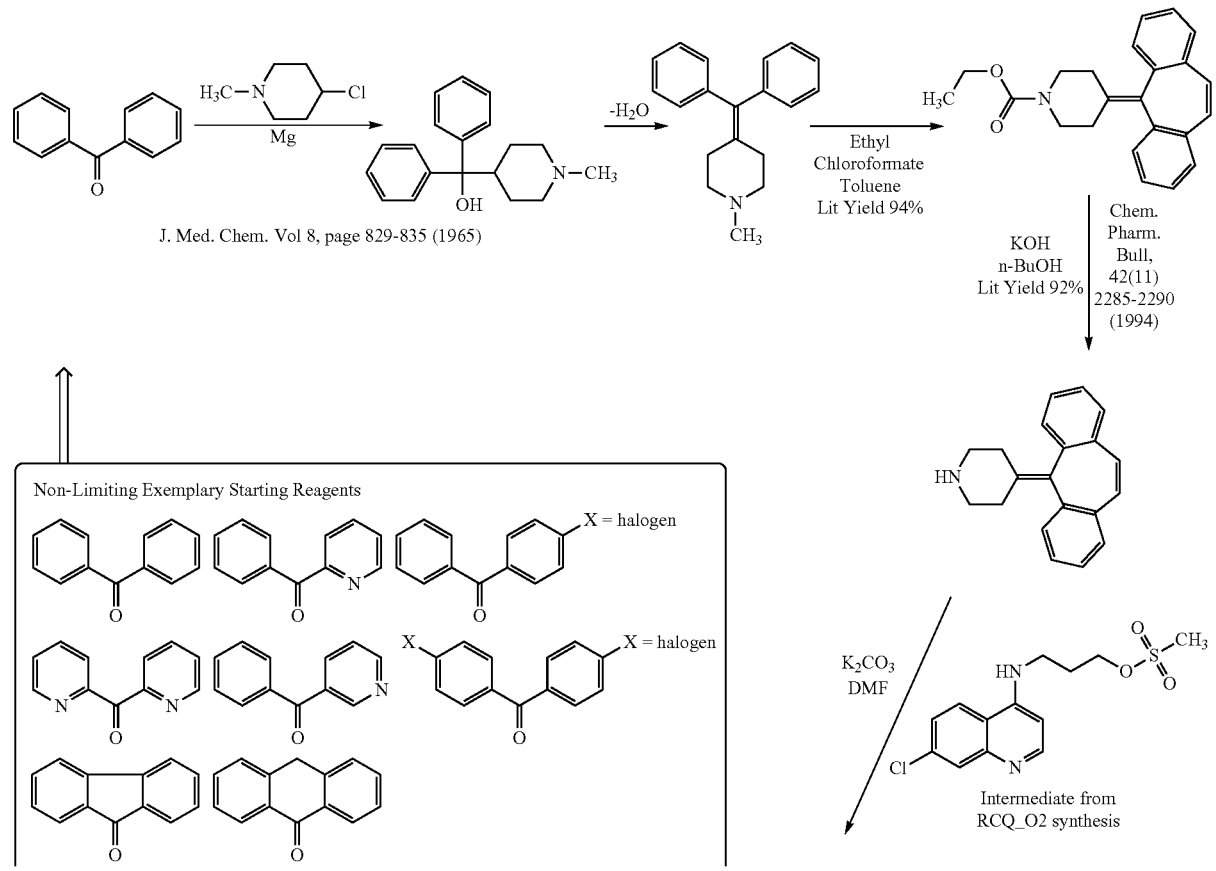

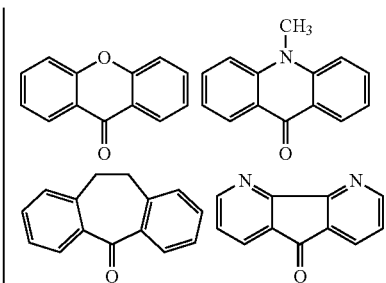
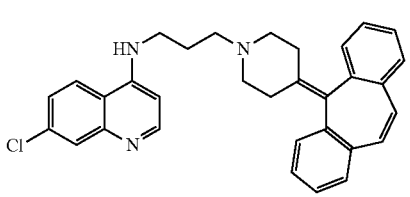
8. General Synthesis of RCQ Compounds
The following synthesis can be used to prepare many of the disclosed RCQ compounds, including, without limitation, compounds recited in Tables 3, 5 and 6.
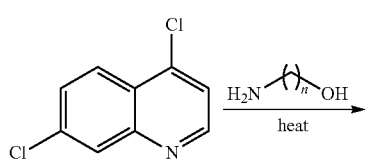
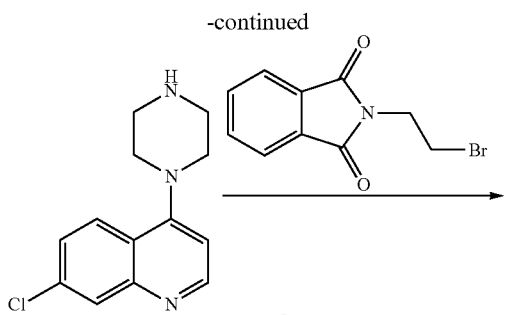
-continued
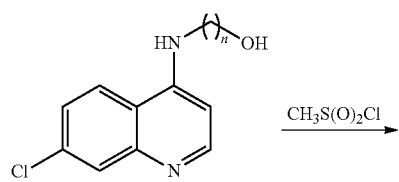
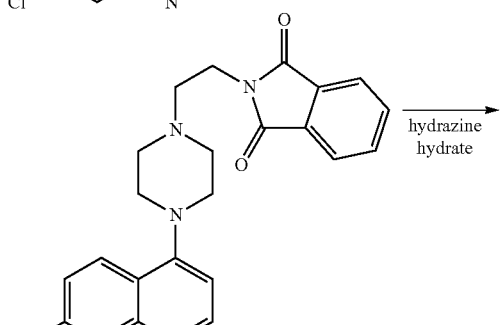
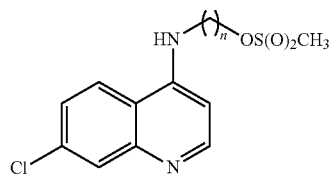
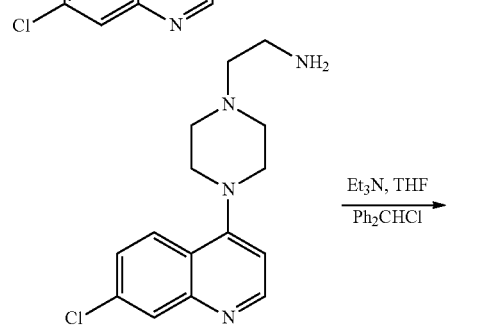
Exemplary Amine Structures:
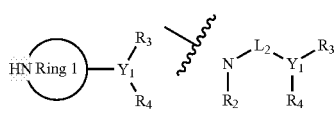
9. Route to RCQ_51
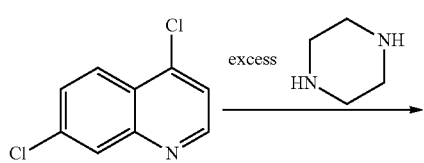
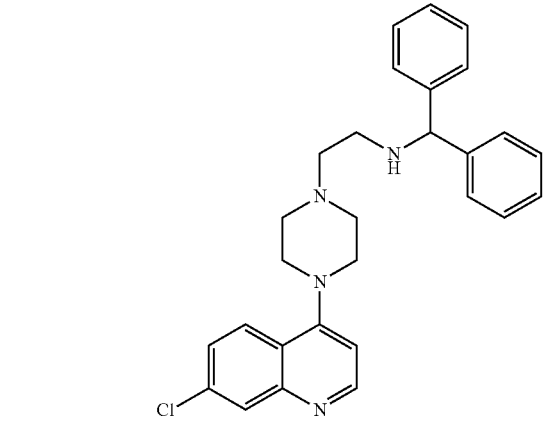

10. Route to RCQ_81

This example illustrates a specific route using the general method of general Method 8 above.

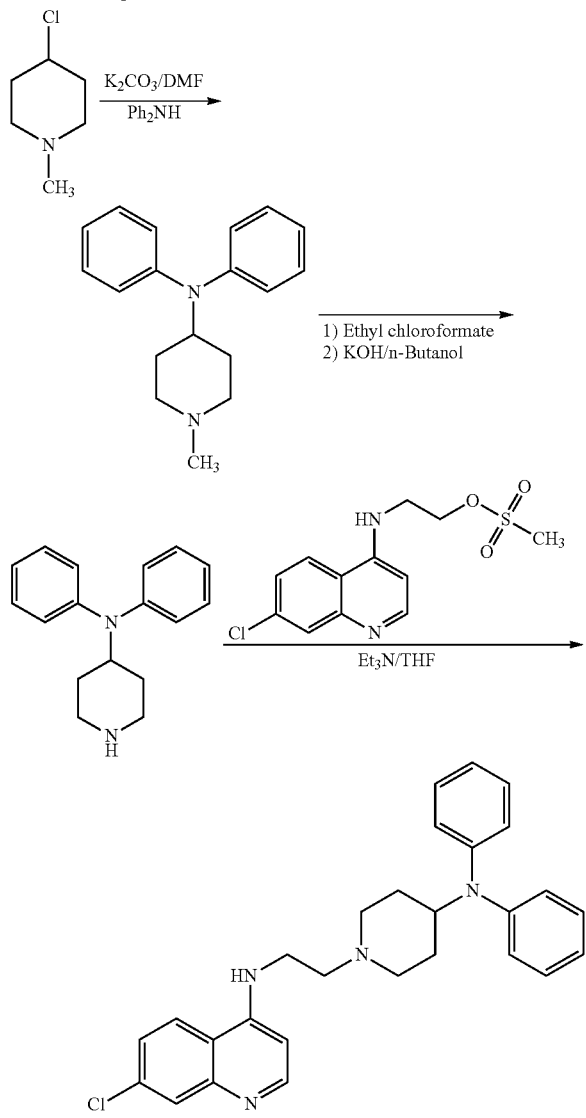

11. Route to Various Linker-Modified RCQs.

The synthesis of various linker-modified RCQs, such as the RCQ_101 compounds recited in Table 3 can be accomplished according to the following general scheme.

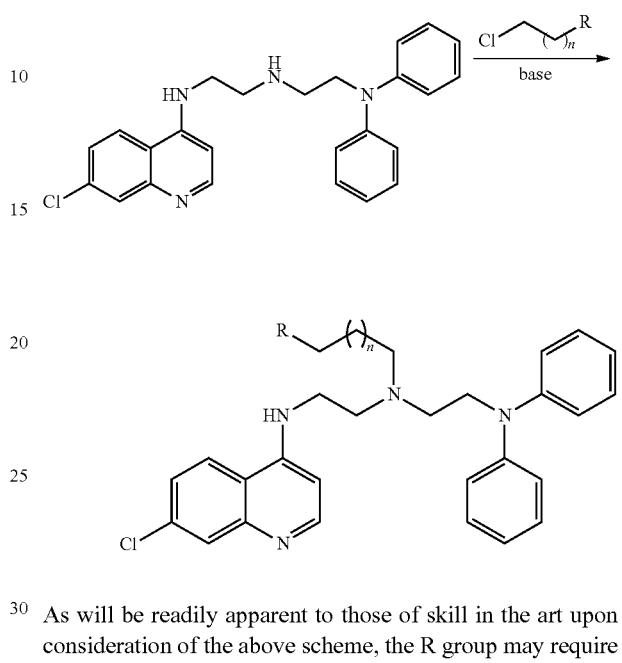

As will be readily apparent to those of skill in the art upon consideration of the above scheme, the R group may require protection to ensure the synthesis proceeds smoothly.

12. Examples of Alternative Syntheses for RCQ Molecules

An alternative to the nucleophilic displacement method 8 described above, this method uses the chloroquine-linker moiety as the nucleophilic component and the reversal agent derivative as the electrophilic component. As will be apparent to those of skill in the art, this scheme can be used to prepare a variety of disclosed RCQ compounds.

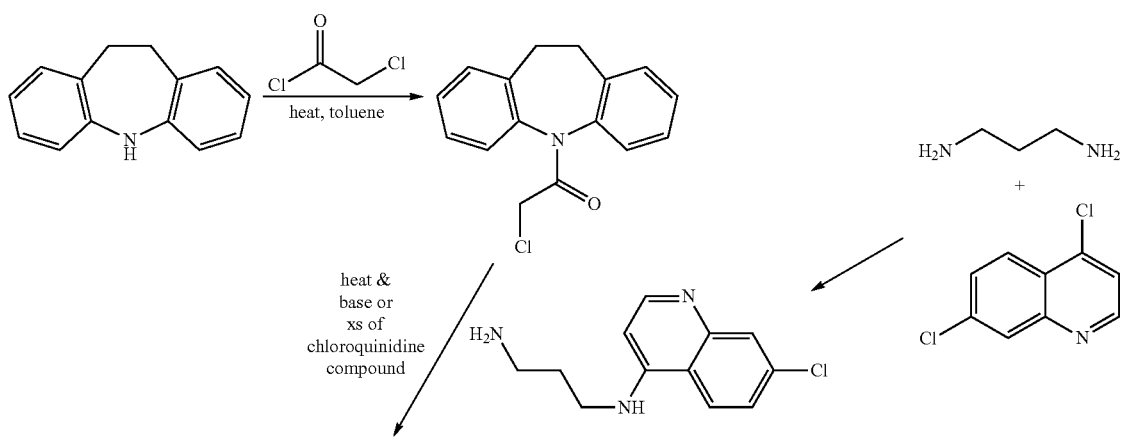

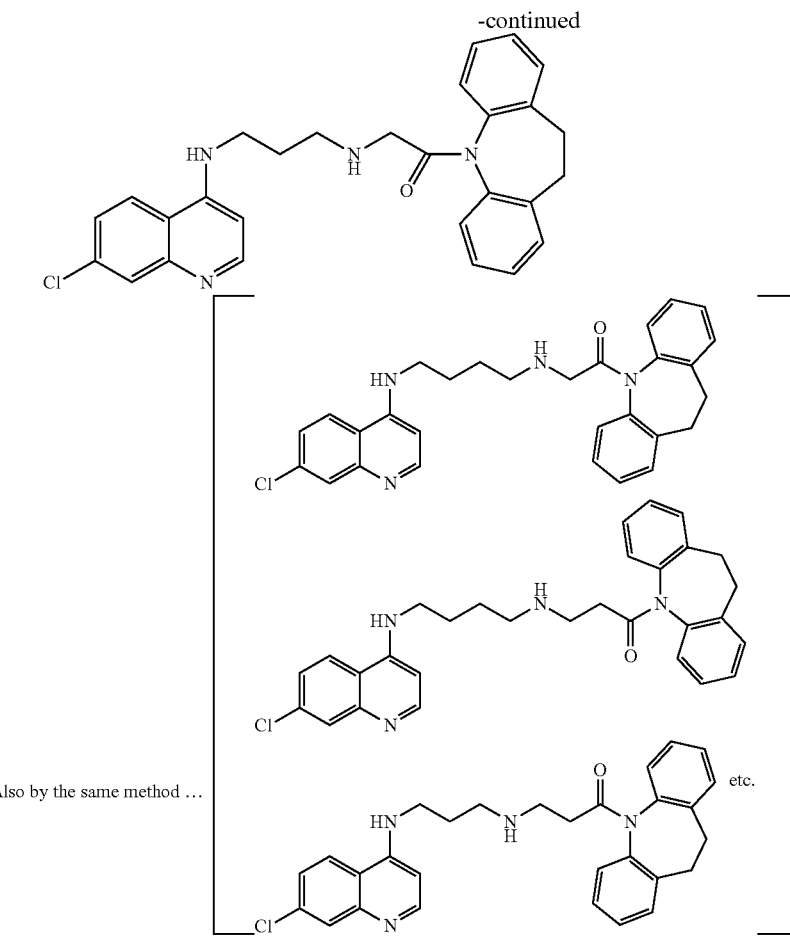

D. Optional Considerations for RCQ Molecules

In some embodiments RCQ compounds are included in pharmaceutical compositions and/or administered to subjects for the treatment of malaria and/or *Plasmodium* sp. infection. Accordingly, it is advantageous for some RCQ embodiments to have characteristics suitable for in vivo administration (particular formulations are discussed in more detail below). One rule of thumb for drug design is Lipinski's "Rule of 5" (Lipinski et al., *Adv. Drug Deliv. Rev.*, 23 (1-3):3-25, 1997), which suggests that absorption and permeation of a drug candidate (which is not a biological transporter substrate) is likely to be increased if at least three of the following parameters is satisfied: (i) there are no more than about 5H-bond donors (expressed as the sum of hydroxyl and amine groups); (ii) the molecular weight is not substantially greater than 500 g/mole (but can be anything less); (iii) the log P (logarithm of the octanol-water partition coefficient of the drug candidate) is no more than about 5; and (iv) there are no more than about 10H-bond acceptors (the sum of nitrogens and oxygens).

As described above, some RCQ compound embodiments can be 'decorated' by adding polar and/or charged groups. See, for example, RCQ_13, which is drawn above with appropriate amines protonated (as they would be expected to exist in the DV). Similar protonated representations can be made for each of the disclosed RCQ structures.

RCQ_13 illustrates methods to increase water solubility of RCQs without dramatically increasing molecular size or perturbing the CQ end of the molecule. Coincidentally, although not bound by theory, RCQ molecules having at least one (such as two, three or four) protonated amines should target to the parasite acidic DV even more efficiently than CQ because the pH of the DV is lower than the surrounding, favoring the protonated state of each nitrogen, thereby thermodynamically driving the equilibrium toward the interior of the DV.

If desirable, water solubility of an RCQ can be increased by modifying (among other positions) the central nitrogen of the aliphatic portion of a disclosed RCQ (as described above; and see, e.g., RCQ_14). For example, adding methylamine or diethylmethylamine at this exemplary position introduces a positive charge. According to Lipinski's "Rule of 5," such positive charge may increase the likelihood for good absorption and permeation of the molecule. RCQ solubility may be measured under a variety of conditions, e.g., at various pHs and in various solvents. Aqueous solvents (such as, water, normal saline solution or other buffered salt solutions) are useful for solubility determinations. For oral administration of a drug (such as, an RCQ), one optional consideration is the solubility of such drug in the digestive system, which has an acid pH. For example, the stomach has a pH from about 1.5 to about 4 and the small intestine has a pH from about 2.5 to about 5.5. In some embodiments, an RCQ preferably will be soluble in aqueous solution (e.g., water) at a pH of less than about 5.5 (such as, from about pH 1.5 to about pH 4, from about pH 2.5 to about pH 5.5, or from pH 1.5 to about pH 5.0).

E. Optional Characterization of RCQ Functional Properties

The disclosed RCQ compounds are useful, at least, in the treatment of malaria and *Plasmodium* sp. infection. CQ is believed to exert its inhibitory effect on *Plasmodium* parasites by binding heme in the DV of the parasite. Accordingly, if it is desirable to do so, non-limiting methods useful to functionally characterize RCQ compounds are heme binding assays and in vitro and in vivo *Plasmodium* sp. bioassays.

1. Heme Binding

Optionally, heme binding of RCQ compounds can be determined by any method known in the art, including, for example, spectrophotometric methods, like UV-VIS spectroscopy or NMR spectroscopy. Methods of measuring heme binding to a variety of molecules using the UV-VIS spectrum have been described (see, e.g., Xu et al., *J. Inorg. Biochem.*, 86 (2-3):617-625, 2001; Xu et al., *Antimicrob. Agents Chemother.*, 46(1):144-150, 2002). Generally, a heme-binding compound (such as a disclosed RCQ) is mixed in increasing concentration with heme (or a heme model compound, such as porphyrin or metalloporphyrin) and the absorbance spectrum is measured from the ultraviolet region well into the visible region (from about 300 nm to about 750 nm). This spectral range includes the so-called Soret and Q-band regions that arise from porphyrin or metalloporphyrin absorbance. Upon interaction between a heme-binding compound and heme (or a heme model compound, such as porphyrin or metalloporphyrin), decreased absorbance in the Soret region is observed. It is believed that such decrease arises from π-π stacking interactions (White, Aggregation of porphyrins and metalloporphyrins, In: *The Porphyrins*. ed. by Dolphin, NewYork:Academic Press, 1978, pp. 303-339).

In particular examples, the formation of heme-RCQ complexes can be determined by UV-VIS spectrophotometric titration, using a variety of commercially available spectrophotometers (such as a Varian-Cary 3E spectrophotometer). The approximate pH of the plasmodial DV, where CQ (or RCQ) is believed to bind to heme in vivo, is pH 4.7; thus, it is useful (though not obligatory) to conduct heme-binding reactions at a pH (e.g., 4.7 or 7) and temperature (e.g., 25° C.) similar to DV conditions in vivo. Titrations of heme (or a heme model) with a RCQ compound can be performed, for example, by successive addition of aliquots of a 1 mM RCQ solution to a 10 μM heme solution. Optionally, pH can be monitored throughout the procedure to ensure that it remains unchanged. In some circumstances, UV-VIS spectral data can be analyzed digitally, and absorbance readings and concentrations corrected for dilution effects. The amount of heme-RCQ complex versus amount of RCQ added to the reaction can be plotted. Such titration curves can be analyzed with Hill plot and non-linear curve fitting methods as described previously (Xu et al., *Antimicrob. Agents Chemother.*, 46(1):144-150, 2002) to obtain association constants for the heme-RCQ binding reaction.

NMR is another optional method that can be used, for example, to provide information about stoichiometry, interaction affinities, and structural details of complexes between RCQ molecules and heme (or heme models, such porphyrins or metalloporphyrins) (White, Aggregation of porphyrins and metalloporphyrins, In: *The Porphyrins*. ed. by Dolphin, NewYork:Academic Press, 1978, pp. 303-339). NMR parameters useful to measure include changes in chemical shift, line-width, and relaxation times. For example, NMR relaxation times give information about proximity to paramagnetic centers (e.g., the Fe in heme), or chemical exchange between species (e.g., bound and free RCQ). A fourth useful parameter to measure is peak area ratio, which is convenient if exchange between complexes is unexpectedly slow. NMR studies can be performed by adding aliquots of heme to RCQ solutions, then monitoring chemical shifts, linewidths, and relaxation times of the RCQ NMR signals. Such techniques are well known in the art (see, for instance, Xu et al., *J. Inorg. Biochem.*, 86 (2-3):617-625, 2001).

If desirable, fluorescence confocal microscopy can also be used to determine whether an RCQ is localized to the DV (see, for instance, Xu et al., *Mol. Biochem. Parasitol.*, 123(1):47-54, 2002).

2. In Vitro and In Vivo Bioassays

One exemplary method for measuring inhibitory effects of RCQ compound in vitro has been reported by Smilkstein et al. (*Antimicrob. Agents Chemother.*, 48(5):1803-1806, 2004). This method employs fluorescent detection of the level of parasitemia in cultured red blood cells and can be automated for high-throughput screening of antimalarial RCQs. This exemplary method allows the inhibitory agent (such as a RCQ) to be in contact with the parasite for an entire developmental cycle without purine starvation, which is in contrast to the traditional $^3$H-hypoxanthine method (Desjardins et al., *Antimicrob. Agents Chemother.*, 16(6): 710-718, 1979). Briefly, to perform the Smilkstein et al. method, an initial parasitemia of approximately 0.2% is attained by adding uninfected red blood cells (RBCs) to a stock culture of *Plasmodium* sp.-infected RBCs. Infected cells (2% v/v) are combined with RCQs (for example, dissolved in DMSO), e.g., at a final concentration of $10^{-11}$ to $10^{-4}$ M. Chloroquine may be added (instead of a RCQ) to some infected RBCs as a control. After a period of incubation (such as about 72 hours), a sufficient amount (e.g., 100 μL) of a fluorescent DNA binding dye-detergent mixture (e.g., Sybr Green I dye-detergent mixture) to lyse cells and bind to DNA is added to the reactions. Because uninfected RBCs have no DNA, only parasite DNA (in infected RBCs) is available for binding to the fluorescent dye (e.g., Sybr Green I). Samples are then incubated in the dark for a period of time (e.g., one hour), followed by measurement of levels of fluorescence. For Sybr Green I, excitation and emission wavelength are 485 and 530 nm, respectively. Fluorescence readings, which represent the amount of parasite DNA in the sample, can be plotted against the Log [drug] and fit to a curve by nonlinear regression to obtain the $IC_{50}$ value for the tested compound.

Various *Plasmodium* sp. parasites are available for testing in vitro efficacy of antimalarial compounds (such as a disclosed RCQ). It is expected that the disclosed RCQ will be effective against both $CQ^R$ and $CQ^S$ *Plasmodium* sp. strains (such as $CQ^R$ and $CQ^S$ *P. falciparum* strains). Exemplary $CQ^S$ and $CQ^R$ *P. falciparum* strains are shown in the following table:

TABLE 11

Drug Susceptibility of *P. falciparum* strains

| Drug | *P. falciparum* strain | | | | | |
|---|---|---|---|---|---|---|
| | D6 | FCR3 | W2 | Dd2 | 3D7 | TM91C235 |
| CQ | S | R | R | R | S | R |
| Quinine | S | S | R | R | NC | R |
| Mefloquine | S/R | S | S | R | NC | R |
| Pyrimethamine | S | S | R | R | NC | R |

TABLE 11-continued

Drug Susceptibility of *P. falciparum* strains

| | P. falciparum strain | | | | | |
|---|---|---|---|---|---|---|
| Drug | D6 | FCR3 | W2 | Dd2 | 3D7 | TM91C235 |
| Cycloguanil | S | S | R | S | NC | NC |
| Sulfadoxine | S | S | R | S | NC | R |

S = sensitive; R = resistant; S/R = intermediate level of resistance; NC = not characterized Antimalarial compounds can also be tested for efficacy in vivo. One non-limiting exemplary method for performing such testing is the 4-day suppressive test (Peters, *Ann. Trop. Med. Parasitol.,* 69(2):155-171, 1975). Briefly, such test involves collecting *P. chabaudi* (Mackinnon and Read, *Philos. Trans. R. Soc. Lond. B Biol. Sci.,* 359:965-986, 2004; Mackinnon et al., *Exp. Parasitol.,* 101 (2-3):121-128, 2002) from a donor animal harboring ~20% parasitemia. Male CF-1 mice at 4-5 weeks of age (~20 g) are infected with ~$10^7$ infected red blood cells via 100 µL tail vein injection and randomly sorted into groups of 4 mice each on day 0. One hour after infection, the mice receive the test agent via oral gavage, or by the intraperitoneal route (at approximately 1-10 times the in vitro $IC_{50}$ values). Drugs are administered once daily for at least 4 days beginning at day 0. Animals are tested weekly for levels of parasitemia, for example, by microscopic analysis of Giemsa-stained blood smears. Efficacy of a tested compound in this bioassay is measured by inhibition of parasite growth as defined previously. In some examples, subjects are expected to be freed of measurable parasites after a period of treatment (such as 30 days).

IV. Pharmaceutical Compositions

The disclosed RCQ compounds are useful, at least, for the treatment of malaria and/or inhibiting the growth of malarial parasites, such as *P. falciparum*. Accordingly, pharmaceutical compositions comprising at least one disclosed RCQ compound are also described herein.

Formulations for pharmaceutical compositions are well known in the art. For example, *Remington's Pharmaceutical Sciences*, by E. W. Martin, Mack Publishing Co., Easton, Pa., 15th Edition, 1975, describes exemplary formulations (and components thereof) suitable for pharmaceutical delivery of disclosed RCQ compounds. Pharmaceutical compositions comprising at least one of the disclosed RCQ compounds can be formulated for use in human or veterinary medicine. Particular formulations of a disclosed pharmaceutical composition may depend, for example, on the mode of administration (e.g., oral or parenteral) and/or on the location of the infection to be treated (e.g., liver-stage and/or blood-stage malaria parasites). In some embodiments, formulations include a pharmaceutically acceptable carrier in addition to at least one active ingredient, such as a RCQ compound. In other embodiments, other medicinal or pharmaceutical agents, for example, with similar, related or complementary effects on the affliction being treated (such as malaria or *Plasmodium* sp. infection), can also be included as active ingredients in a pharmaceutical composition.

Pharmaceutically acceptable carriers useful for the disclosed methods and compositions are conventional in the art. The nature of a pharmaceutical carrier will depend on the particular mode of administration being employed. For example, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can optionally contain minor amounts of non-toxic auxiliary substances (e.g., excipients), such as wetting or emulsifying agents, preservatives, and pH buffering agents and the like; for example, sodium acetate or sorbitan monolaurate. Other non-limiting excipients include, nonionic solubilizers, such as cremophor, or proteins, such as human serum albumin or plasma preparations.

The disclosed pharmaceutical compositions may be formulated as a pharmaceutically acceptable salt of a disclosed RCQ compound. Pharmaceutically acceptable salts are non-toxic salts of a free base form of a compound that possesses the desired pharmacological activity of the free base. These salts may be derived from inorganic or organic acids. Non-limiting examples of suitable inorganic acids are hydrochloric acid, nitric acid, hydrobromic acid, sulfuric acid, hydriodic acid, and phosphoric acid. Non-limiting examples of suitable organic acids are acetic acid, propionic acid, glycolic acid, lactic acid, pyruvic acid, malonic acid, succinic acid, malic acid, maleic acid, fumaric acid, tartaric acid, citric acid, benzoic acid, cinnamic acid, mandelic acid, methanesulfonic acid, ethanesulfonic acid, p-toluenesulfonic acid, methyl sulfonic acid, salicylic acid, formic acid, trichloroacetic acid, trifluoroacetic acid, gluconic acid, asparagic acid, aspartic acid, benzenesulfonic acid, p-toluenesulfonic acid, naphthalenesulfonic acid, and the like. Lists of other suitable pharmaceutically acceptable salts are found in *Remington's Pharmaceutical Sciences,* 17th Edition, Mack Publishing Company, Easton, Pa., 1985. A pharmaceutically acceptable salt may also serve to adjust the osmotic pressure of the composition.

The dosage form of a disclosed pharmaceutical composition will be determined by the mode of administration chosen. For example, in addition to injectable fluids, topical or oral dosage forms may be employed. Topical preparations may include eye drops, ointments, sprays and the like. Oral formulations may be liquid (e.g., syrups, solutions or suspensions), or solid (e.g., powders, pills, tablets, or capsules). Methods of preparing such dosage forms are known, or will be apparent, to those skilled in the art.

Certain embodiments of the pharmaceutical compositions comprising a disclosed RCQ compound may be formulated in unit dosage form suitable for individual administration of precise dosages. The amount of active ingredient (e.g., RCQ compound) administered will depend on the subject being treated, the severity of the affliction, and the manner of administration, and is known to those skilled in the art. Within these bounds, the formulation to be administered will contain a quantity of the extracts or compounds disclosed herein in an amount effective to achieve the desired effect in the subject being treated.

V. Methods of Use

The present disclosure includes methods of treating malaria and/or inhibiting *Plasmodium* sp. parasite growth (including $CQ^R$ and $CQ^S$ parasites). In some examples, the pathogen is *P. falciparum, P. vivax, P. ovale, P. malariae,* or a combination thereof. In other examples, the disease or *Plasmodium* sp. to be treated is resistant to CQ or other traditional malaria treatment.

Disclosed methods includes administering a disclosed RCQ compounds (and, optionally, one or more other pharmaceutical agents) to a subject in a pharmaceutically acceptable carrier and in an amount effective to treat malaria or *Plasmodium* sp. infection. The treatment can be used prophylactically in any subject in a demographic group at substantial risk for such diseases; for example, subjects who are traveling to areas where malaria (such as $CQ^R$ malaria) is endemic (including, e.g., Southeast Asia, Africa, Papua New Guinea, Indonesia, Thailand, and India). Notably, pregnant women are twice as likely to attract malaria-carrying mosquitoes as non-pregnant women (perhaps due to a greater volume of exhaled air and a warmer skin surface), and, therefore, are especially vulnerable to malaria. Alternatively, subjects can be selected using more specific criteria, such as a probable or definitive diagnosis of malaria or *Plasmodium* sp. infection based on, for example, clinical signs and symptoms and/or laboratory evidence of parasite infection. An example of such a subject would be a person who presents clinically with symptoms resembling the flu (including periods of chills and fever lasting several hours and occurring every few days). In more severe cases, an infected subject may present with enlarged spleen and/or liver, anemia, and jaundice. Other subjects may be identified based on positive tests for parasite-specific proteins, including plasmodial histidine rich protein-2 (HRP-2) or parasite-specific lactate dehydrogenase (pLDH) or parasite DNA. A number of antibodies specific for *Plasmodium* parasites are available and are useful for diagnostic immunoassays or immunofluorescence techniques. PCR can also be used to diagnosis malaria in a subject (*Am. J. Trop. Med. Hyg.*, 65(4):355-363, 2001).

Routes of administration useful in the disclosed methods include but are not limited to oral and parenteral routes, such as intravenous (iv), intraperitoneal (ip), rectal, topical, ophthalmic, nasal, and transdermal. Formulations for these dosage forms are described above.

An effective amount of a RCQ will depend, at least, on the particular method of use, the subject being treated, the severity of the affliction, and the manner of administration of the therapeutic composition. A "therapeutically effective amount" of a composition is a quantity of a specified compound sufficient to achieve a desired effect in a subject (host) being treated. For example, this may be the amount of a RCQ necessary to prevent, inhibit, reduce or relieve *Plasmodium* sp. infection and/or one or more symptoms of malaria in a subject. Specific anti-*Plasmodium* sp. effects that may result from RCQ administration are described herein. Ideally, a therapeutically effective amount of a RCQ is an amount sufficient to prevent, inhibit, reduce or relieve *Plasmodium* sp. infection and/or one or more symptoms of malaria without causing a substantial cytotoxic effect on host cells. It is anticipated that disclosed RCQs will be well tolerated in humans because, at least some, quinoline analogs (such as CQ) and reversal agents (such as Imipramine) have been demonstrated safe for administration to humans in combination therapies (albeit at much higher dosages of reversal agent).

Therapeutically effective doses (or growth inhibitory amounts) of a disclosed RCQ compound or pharmaceutical composition can be determined by one of skill in the art, with a goal of achieving local (e.g., tissue) concentrations that are at least as high as the $IC_{50}$ of the applicable compound disclosed in the examples herein. An example of a dosage range is from about 0.1 to about 200 mg/kg body weight orally in single or divided doses. In particular examples, a dosage range is from about 1.0 to about 100 mg/kg body weight orally in single or divided doses, including from about 1.0 to about 50 mg/kg body weight, from about 1.0 to about 25 mg/kg body weight, from about 1.0 to about 10 mg/kg body weight (assuming an average body weight of approximately 70 kg; values adjusted accordingly for persons weighing more or less than average). For oral administration, the compositions are, for example, provided in the form of a tablet containing from about 50 to about 1000 mg of the active ingredient, particularly about 75 mg, about 100 mg, about 200 mg, about 400 mg, about 500 mg, about 600 mg, about 750 mg, or about 1000 mg of the active ingredient for the symptomatic adjustment of the dosage to the subject being treated. In one exemplary oral dosage regimen, a tablet containing from about 500 mg to about 1000 mg active ingredient is administered once (e.g., a loading dose) followed by administration of ½ dosage tablets (e.g., from about 250 to about 500 mg) each 6 to 24 hours for at least 3 days.

The specific dose level and frequency of dosage for any particular subject may be varied and will depend upon a variety of factors, including the activity of the specific RCQ compound, the metabolic stability and length of action of that compound, the age, body weight, general health, sex and diet of the subject, mode and time of administration, rate of excretion, drug combination, and severity of the condition of the host undergoing therapy.

The present disclosure also contemplates combinations of one or more disclosed RCQs with one or more other agents or therapies useful in the treatment of malaria and/or *Plasmodium* sp. parasitemia. For example, one or more disclosed RCQs may be administered in combination with effective doses of other medicinal and pharmaceutical agents, or in combination other non-medicinal therapies, such as hormone or radiation therapy. The term "administration in combination with" refers to both concurrent and sequential administration of the active agents. In some examples, the one or more other antimalarial agents or therapies include artesunate and mefloquine (either individually or in an artesunate-mefloquine combination), or sulfadoxine and pyrimethamine (either individually or in a sulfadoxine-pyrimethamine combination (commercially available as Fanisdar™)). In particular examples, the one or more other antimalarial agents or therapies have at least one different mode of action than is proposed (although not binding) for a disclosed RCQ; thus, for instance, a combination agent or therapy may target mitochondria and/or dihydrofolate reductase.

Other method embodiments involve inhibiting the growth of at least one *Plasmodium* sp. (such as *P. falciparum, P. vivax, P. ovale*, or *P. malariae*, or a combination thereof) by contacting the parasite(s) with a growth inhibitory amount of a disclosed RCQ. Inhibition of *Plasmodium* sp. growth was defined above. Contact between a RCQ and a parasite may occur in vitro (such as in culture conditions) or in vivo (such as in a subject infected with at least one *Plasmodium* sp.). In certain method embodiments, growth inhibitory amounts include amounts described in the Examples (for example, $LC_{50}$ concentrations). In other examples, a growth inhibitory amount is from about 1 nM to about 1 μM of a disclosed RCQ (such as from about 5 nM to about 50 nM, or from about 5 nM to about 25 nM).

EXAMPLES

The following examples are provided to illustrate certain particular features and/or embodiments. These examples should not be construed to limit the invention to the particular features or embodiments described.

Example 1

[RCQ_02] is Highly Effective Against $CQ^R$ and $CQ^S$ P. falciparium

This Example illustrates the synthesis of an exemplary RCQ, referred to as RCQ_02 (formally, N'-(7-Chloro-quinolin-4-yl)-N-[3-(10,11-dihydro-dibenzo[b,f]azepin-5-yl)-propyl]-N-methyl-propane-1,3-diamine). RCQ_02 has a 7-chloroquinoline CQ core with the reversal agent, imipramine, substituted for the diethylamino end of the chloroquine side chain. Imipramine was selected as the reversal agent moiety in RCQ_02 because imipramine is synthetically (in fact, commercially) available, symmetric, simple, and conforms to a published reversal agent pharmacophore (Bhattacharjee et al., *J. Chem. Inf. Comput. Sci.*, 42(5):1212-1220, 2002), having the two hydrophobic rings and an aliphatic chain terminating in a positively charged nitrogen. CQ analogs with 3 and 4 carbons in the aliphatic chain are known (e.g., De et al., *J. Med. Chem.*, 41(25):4918-4926, 1998; De et al., *Am. J. Trop. Med. Hyg.*, 55(6):579-583, 1996; Ramanathan-Girish et al., *Int. J. Toxicol.*, 23(3):179-189, 2004), and the 3-carbon methylene analog, as well as significantly longer methylene chain molecules have activity against $CQ^R$ P. falciparum.

RCQ_02 was synthesized as follows:

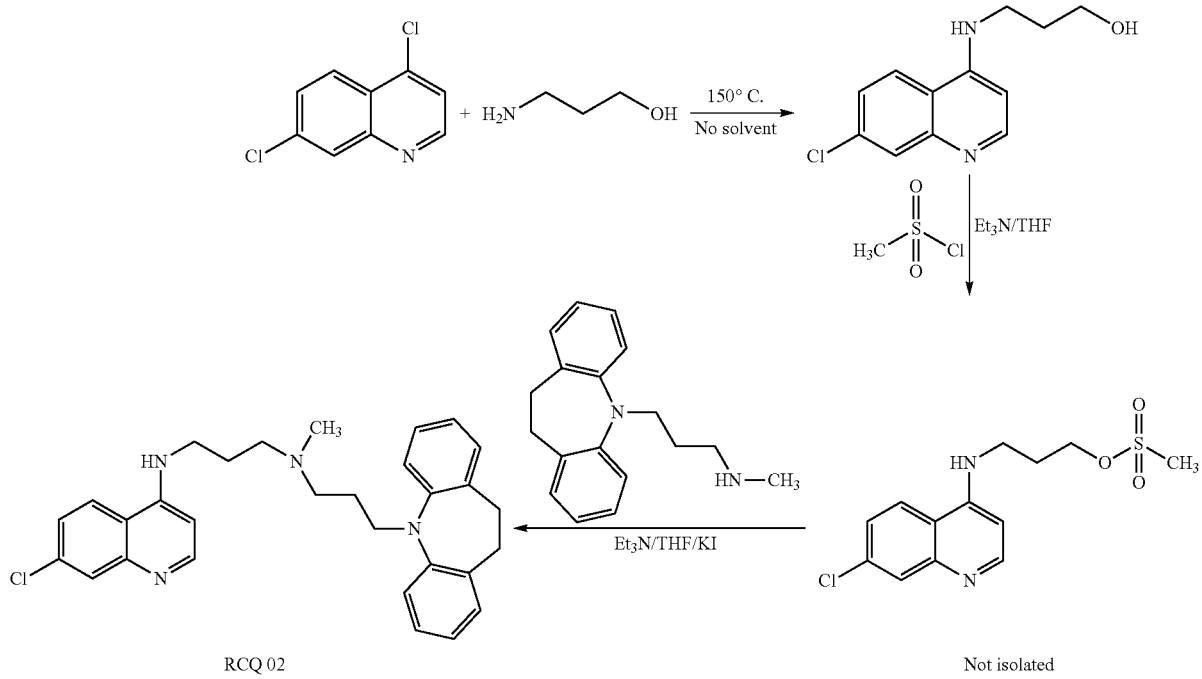

Reactions were monitored by thin layer chromatography and/or $^1$H nuclear magnetic resonance spectroscopy (NMR) as appropriate. All products were fully characterized by $^1$H NMR, and were deemed to be >95% pure after column chromatography using an alumina matrix and ethyl acetate/hexane (30:70 by volume) as the eluting solvent. Reaction yield was approximately 10%; however, higher yields would be expected with minor modifications of the reaction conditions, including isolation of intermediates or varying reaction temperature, reactant concentrations and/or reaction solvent(s). Such minor modifications are easily performed by those of ordinary skill in the art.

Example 2

RCQ_02 and CQ have Substantially Similar Electrostatic Potentials and Electron Densities, and RCQ_02 and RCQ_31 Effectively Bind Heme This Example illustrates that the covalent coupling of a reversal agent (e.g., imipramine) to CQ does not substantially affect the electrostatic potential or electron density of the CQ moiety, nor affect the ability of the hybrid molecule to interact with heme.

The GAUSSIAN-03 program (which is publicly available at the website having the address www.gaussian.com) was used to ascertain the charge distribution around CQ and the CQ moiety of RCQ_02. Calculations were performed at the B3LYP/6-311+g(d) level of theory, and results were visualized with the program gOpenMol (which is publicly available at the website having the address www.csc.fi/gopenmol).

FIG. 1 shows that the electrostatic potentials and electron densities are nearly identical for the CQ portion of each of these molecules. The same result was obtained for deprotonated quinoline ring nitrogens. Because the electrical properties of chloroquine are believed to underlie its binding to heme, the results shown in FIG. 1 strongly suggested that RCQ_02 would also bind with heme or with hemozoin.

Heme binding by RCQ_02, in fact, was demonstrated by measuring the optical spectrum of heme in the absence and presence of increasing amounts of RCQ_02 under conditions (e.g., pH 4.7) similar to *Plasmodium* sp. DV, as previously described (Xu et al., *J. Inorg. Biochem.*, 86 (2-3):617-625, 2001; Xu et al., *Antimicrob. Agents Chemother.*, 46(1):144-150, 2002). Briefly, 2-10 μl aliquots of a 1 mM RCQ_02 solution (pH 4.8) were successively added to a 10 µM heme solution (pH 4.8) in a 1 cm (1-3 ml) quartz cuvette. The initial volume of heme solution in the cuvette was 2000 µl. pH was monitored to ensure that it remained unchanged throughout the procedure. The UV-Vis spectrum (from 200 nm to 800 nm) was measured at each concentration of RCQ-02 using a Varian-Cary 3E spectrophotometer with a temperature-controlled cell holder. All UV-VIS spectral data were analyzed digitally, and absorbance readings and concentrations were corrected for dilution effects.

Figure 2:
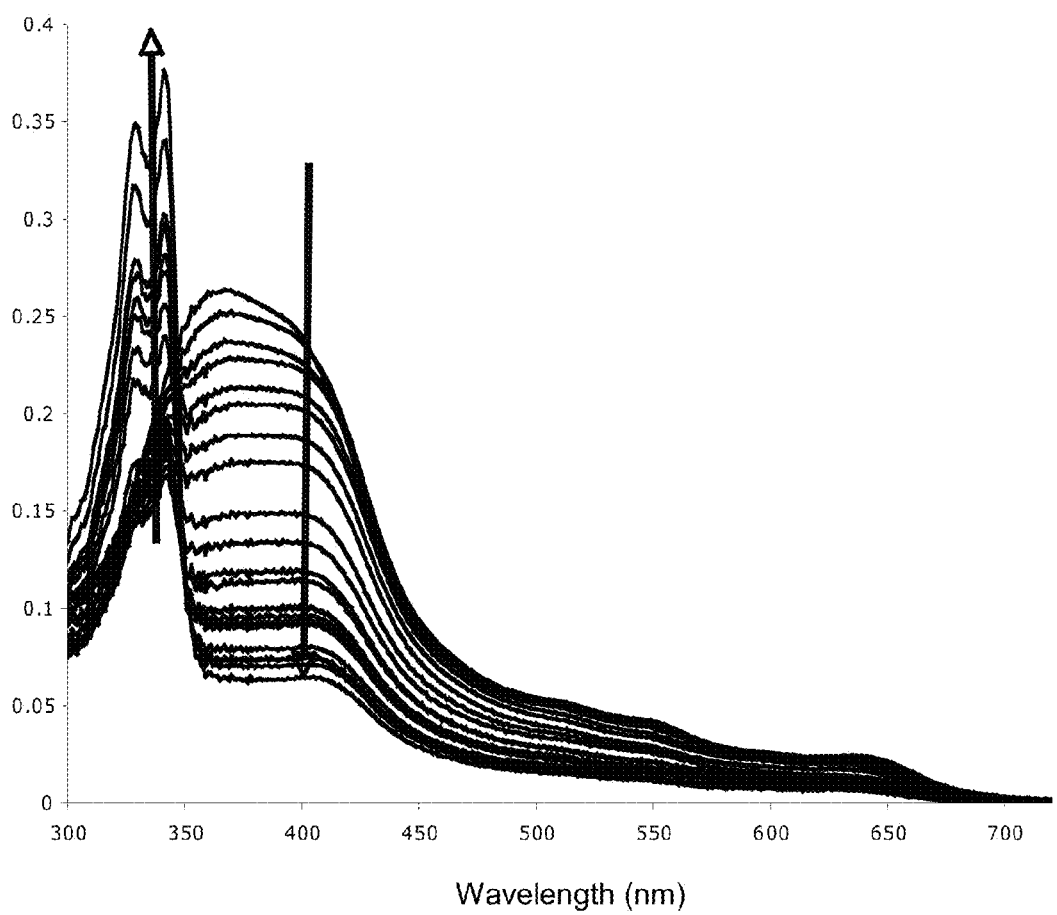
FIG. 2 shows a series of UV-VIS spectra of heme in the presence of increasing amounts of RCQ_02 at pH 4.7. RCQ_02 absorbance is shown by the open up-arrow. A decreased value of heme absorbance in the Soret region (open down-arrow) indicated RCQ_02 heme binding. These spectra were corrected for the slight change in sample volume (2.5% at the last addition) during the course of the titration.

FIG. 2 shows the expected lowering of the Soret band, which is known to accompany binding or complexation of heme by an aromatic molecule (such as CQ or a RCQ). This interaction is thought to involve π-π stacking of the molecules (e.g., Shelnutt, *Inorg. Chem.*, 22:2535-2544, 1983).

RCQ_02 titration curves were with Hill plot and non-linear curve fitting methods as described previously (Xu et al., *Antimicrob. Agents Chemother.*, 46(1):144-150, 2002). With the assumption that the heme is dimeric (µ-oxo), the following equilibrium expression was applied to the RCQ/heme reaction:

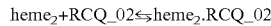

Accordingly, a $heme_2.RCQ\_02$ association constant of approximately $7.5\times10^5$ $M^{-1}$ at pH 5.7 as calculated, which is comparable to (albeit slightly lower than) the association constant reported for $CQ.heme_2$ (K~$4\times10^5$ $M^{-1}$ at pH 5.7; Dorn et al., *Biochem. Pharmacol.*, 55(6):727-736, 1998; Xu et al., *J. Inorg. Biochem.*, 86 (2-3):617-625, 2001).

Similar methodologies as described for RCQ_02 were used to measure a heme association constant for RCQ_31 of $5\times10^5 M^{-1}$.

Example 3

RCQ_02 is Highly Effective Against $CQ^R$ and $CQ^S$ *P. falciparum* Strains

This Example demonstrates that RCQ_02 is a highly effective inhibitor of the growth of $CQ^R$ and $CQ^S$ *P. falciparum* strains in vitro.

An in vitro fluorescence assay for determining $IC_{50}$ of antimalarial drugs was performed as previously described by Smilkstein et al. (*Antimicrob. Agents Chemother.*, 48(5): 1803-1806, 2004). This relatively low-cost procedure can be automated for high-throughput screening of the antimalarial activities of RCQs described herein. Advantageous, this method also allows the tested agent (e.g, a RCQ) to be in contact with the parasite for an entire developmental cycle without purine starvation (which occurs with the commonly used $^3H$-hypoxanthine method; see, e.g., Desjardins et al., *Antimicrob. Agents Chemother.*, 16, (6):710-7188, 1979).

Briefly, an initial parasitemia of approximately 0.2% was attained by addition of uninfected red blood cells to a stock culture of cells infected with Dd2 ($CQ^R$) or D6 ($CQ^S$) *P. falciparum* strains. A 10 mM RCQ_02 solution (in DMSO) was prepared. RCQ_02 (at a final concentration from $10^{-11}$ to $10^{-4}$ M) and infected red blood cells (at a final concentration of 2% (v/v)) were mixed in 100 µL samples in individual wells of a 96-well plate. Each sample was prepared in triplicate. A triplicate set of reactions containing CQ (instead of RCQ_02) was included as a control. After a 72 hour incubation period, Sybr Green I dye-detergent mixture (100 µL) was added to each reaction. The samples were further incubated for an hour in the dark, and then placed in a 96-well fluorescence plate reader (Gemini-EM, Molecular Diagnostics) and analyzed with excitation and emission wavelength bands at 485 and 530 nm, respectively. Fluorescence readings were plotted against the Log [drug], and curve fitting performed by nonlinear regression to find the $IC_{50}$ value.

FIG. 3A shows the effect of CQ concentrations on the growth of D6 and Dd2 *P. falciparum* strains. FIG. 3B shows the effect of RCQ_02 concentrations on the growth of D6 and Dd2 *P. falciparum* strains. $IC_{50}$ values were calculated from these data, as described above, and are summarized in FIG. 3C and in the following Table 12:

TABLE 12

IC50 Values for RCQ_02 and CQ Against $CQ^R$ and $CQ^S$ *P. falciparum*

| Molecule | *P. falciparum* cell line | Characteristic | $IC_{50}$ (nM) |
| --- | --- | --- | --- |
| RCQ_02 | D6 | $CQ^S$ | 2.9 |
| CQ | D6 | $CQ^S$ | 6.5 |
| RCQ_02 | Dd2 | $CQ^R$ | 5.3 |
| CQ | Dd2 | $CQ^R$ | 102 |

Figure 3:
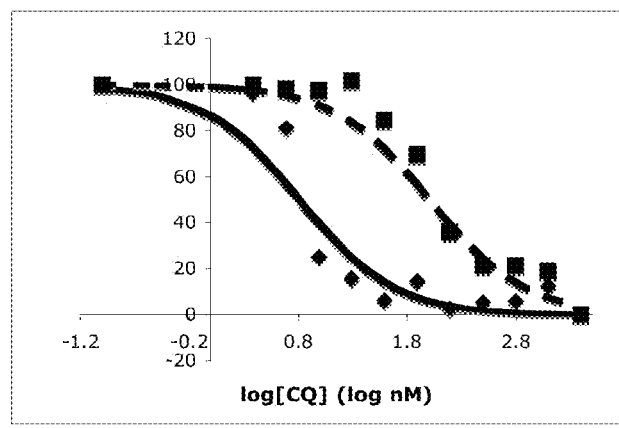
FIG. 3 shows a series of graphs relating to $IC_{50}$ determinations for chloroquine (CQ) and RCQ_02 in $CQ^R$ (Dd2) and $CR^S$ (D6) *P. falciparum* strains.
Figure 3:
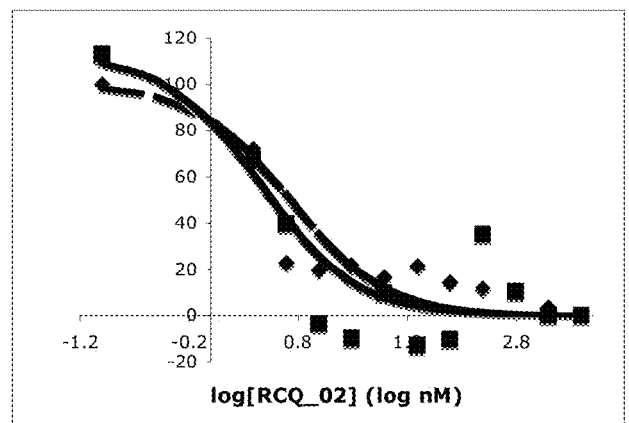
Figure 3:
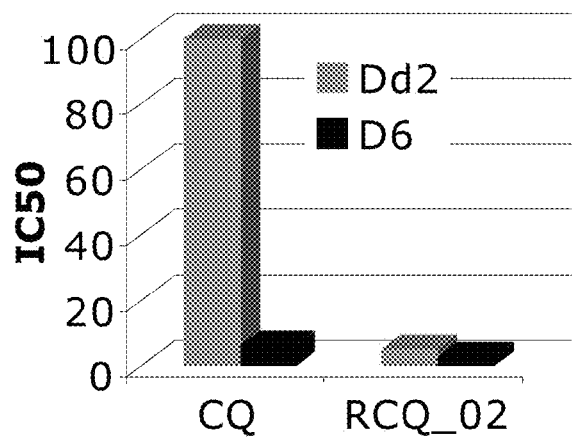
Figure 4:
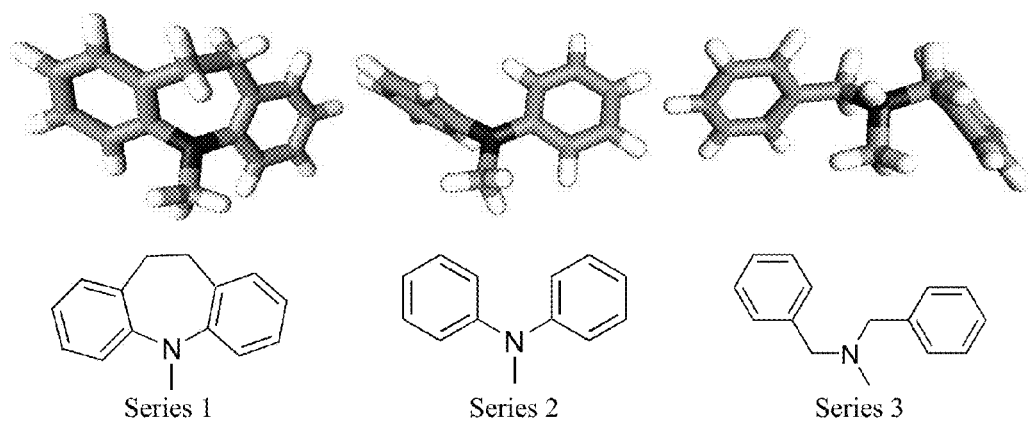
FIG. 4 shows a comparison between selected reversal agent aromatic ring ends (Series 1, 2, and 3). These are energy-minimized representative conformers at the HF(6-31G) level in Gaussian03.

FIG. 3 and Table 12 demonstrate that RCQ_02 has an in vitro activity that is better than CQ against either $CQ^R$ or $CQ^S$ *P. falciparum*. In fact, RCQ_02 is as, or nearly as, active against $CQ^R$ and $CQ^S$ *P. falciparum* as some of the most effective drugs reported to date. including bisquinoline derivatives (Vennerstrom et al., *J. Med. Chem.*, 41(22):4360-4364, 1998; Vennerstrom et al., *J. Med. Chem.*, 35(11):2129-2134, 1992; Basco et al., *Am. J. Trop. Med. Hyg.*, 50(2): 200-205, 1994).

As compared to CQ, RCQ_02 had a lower heme binding constant and a lower $IC_{50}$ against $CQ^R$ and $CQ^S$ *P. falciparum*. Taken together, these findings suggest at least one non-binding theory of RCQ_02 action, which follows: RCQ_02 may obtain higher intra-DV concentrations (than does CQ) by the reversal agent moiety reducing the efflux of the RCQ_02 molecule from the DV. Higher intra-DV concentrations of RCQ_02 may permit more heme to be retained in the DV (as mediated by the CQ moiety of the RCQ), which further thwarts *Plasmodium* sp. heme-detoxification mechanism and thereby inhibits parasite growth. Since low-level CQ efflux occurs even in $CQ^S$ malaria (Krogstad et al., *Science*, 238(4831):1283-1285, 1987; Sanchez et al., *Biochem.*, 43(51):16365-16373, 2004; Sanchez et al., *Biochem.*, 42(31):9383-9394, 2003), RCQ_02 (and RCQs, in general) may be more effective than CQ even against $CQ^S$ strains by inhibiting low-level drug efflux in the $CQ^S$ strains.

Example 4

Other RCQs Also are Highly Effective Against $CQ^R$ and $CQ^S$ *P. falciparum* Strains This Example demonstrates that numerous of the disclosed RCQs strongly inhibit the growth of $CQ^R$ and $CQ^S$ *P. falciparum* strains. Using the same methods as described in Example 3, the $IC_{50}$ values for *P. falciparum* growth inhibition for a variety of RCQs were determined and are summarized below:

TABLE 13

Growth Inhibition of Various Strains by Exemplary RCQs

| Molecule | IC$_{50}$ (nM) | | |
|---|---|---|---|
| | D6 (CQ$^S$) | Dd2 (CQ$^R$) | W2 (CQ$^R$) |
| CQ | 6.9 | 102 | 250 |
| RCQ_02 | 2.9 | 5.3 | |
| RCQ_05(desMe) | 36 | 27 | |
| RCQ_22 | 45 | 79 | |
| RCQ_26 | 7.6 | 10.6 | |
| RCQ_31 | 1.0 | 3.6 | 4.3 |
| RCQ_32 | 2.6 | 3.4 | 3.4 |
| RCQ_33 | 8.1 | 9.3 | 9.3 |
| RCQ_34 | 2.4 | 3.7 | 2.5 |
| RCQ_35 | 4.0 | 6.0 | 4.0 |
| RCQ_36 | 11.7 | 98 | |
| RCQ_37F2 | 15 | 19 | |
| RCQ_42 | 2.1 | 1.8 | |
| RCQ_72 | 9.2 | 9.6 | |
| RCQ_73 | 4.8 | 4.1 | |
| RCQ_74 | 15 | 9.8 | |
| RCQ_76 | 21.1 | 15.3 | |
| RCQ_351 | 141 | 164 | |
| Q_38a | 280 | 400 | |

The compound named Q_38a has the following structure:

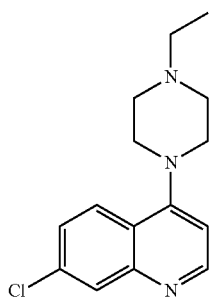

Q_38a

This Example validates the effectiveness of using hybrid molecules (RCQs) such as those described herein to impair the growth of CQ$^R$ and CQ$^S$ Plasmodium sp. parasites. All of the RCQs tested inhibited the growth of CQ$^S$ strains near to (or significantly less than) the effective concentration of CQ. In contrast to CQ, however, each of the foregoing RCQs advantageously also inhibited the growth of at least one (and in some cases, two) CQ$^R$ strains.

The results in this Example and Examples 2 and 3, indicate (among other things) that (i) K$_{assoc}$ for heme binding is not simply correlated with IC$_{50}$; (ii) RCQs work nearly as well against CQ$^R$ P. falciparum strains (e.g., W2 or Dd2) as they do against CQ$^S$ strains (e.g., D6); (iii) many RCQs are significantly better than CQ even against CQ$^S$ P. falciparum (e.g., D6) by as much as a factor of nearly 7; (iv) substitution of Cl at the p-position of an aromatic ring at the reversal agent end of an RCQ molecule has no negative effect on the activity of the molecule (compare RCQ_34 to RCQ_35); thus, comparable substitutions in a variety of RCQs should be well tolerated; and (v) a piperazine ring system in the linker between the reversal agent and quinoline ring is one exemplary structural feature that appears to decrease the IC$_{50}$ of the resultant compound.

Example 5

RCQs are Non-Toxic to Mouse Spleen Lymphocytes

This Example illustrates that a variety of RCQs have no significant cytotoxicity when introduced into mouse spleen lymphocytes cultures in vitro.

RCQ cytotoxicity was determined against mitogen-induced murine spleen lymphocytes in vitro using the Alamar Blue assay (as described by Ahmed et al., J. Immunol. Meth., 170(2):211-224, 1994). Mouse spleen lymphocytes were isolated from C57B1/6J mice by teasing tissues on a metallic sieve screen. Cells thus obtained were washed in RPMI 1640 media, then resuspended in complete RPMI media containing 10% FBS, 50 µg/ml penicillin/streptomycin, 50 µM β-mercaptoethanol, and 1 µM/mL concanavalin A for 1 minute. Two hundred (200) µl isolated cells were then seeded in separate wells of a 96-well flat-bottom tissue culture plate at a density of 2×10$^5$ cells per well. Test drug was added to the individual wells at concentrations of 0 to 62 µM. After 72 hours incubation in a humidified atmosphere at 37° C. and 5% CO$_2$, a solution of resazurin PBS was added to a final concentration 10 µM, and the plates were returned to the incubator for another 24 hours. Resazurin is a substrate which changes color in response to metabolic activity (such as, living cells). The fluorescence of the cell-containing samples was measured with a Gemini EM plate reader with excitation at 560 nM and emission at 590 nM. LC$_{50}$ values were determined from plots of florescence versus drug concentration using non-linear regression by Prism software.

As shown in the following table, the tested RCQs had cytotoxicity values in the range of 700 nM (e.g., RCQ_02, RCQ_22, and RCQ_73) to 5300 nM (e.g., RCQ_36).

TABLE 14

Cytotoxicity of Exemplary RCQs

| Molecule | Cytotoxicity (nM) | Therapeutic Index | |
|---|---|---|---|
| | | D6 | Dd2 |
| CQ | 12400 | 1797 | 122 |
| RCQ_02 | 700 | 240 | 132 |
| RCQ_22 | 700 | 16 | 9 |
| RCQ_31 | 1900 | 1900 | 528 |
| RCQ_32 | 1400 | 538 | 412 |
| RCQ_33 | 1400 | 173 | 151 |
| RCQ_34 | 1100 | 458 | 297 |
| RCQ_35 | 800 | 200 | 133 |
| RCQ_36 | 5300 | 453 | 54 |
| RCQ_37F2 | 4100 | 273 | 215 |
| RCQ_42 | 1100 | 523 | 611 |
| RCQ_72 | 2500 | 272 | 260 |
| RCQ_73 | 700 | 145 | 171 |
| RCQ_74 | 900 | 60 | 92 |
| RCQ_76 | 2500 | 118 | 163 |
| Q_38a | 43000 | 153 | 108 |

Although chloroquine (CQ) had a higher cytotoxic concentration than all of the tested RCQs, the in vitro therapeutic index (ratio of cytotoxicity/IC$_{50}$ for P. falciparum) for each of the RCQs was still quite large. Thus, the toxic dose for nearly all of the tested RCQs is hundreds of times higher or even thousands of times higher (for RCQ_31) than the therapeutic dose. These results indicate that there is a good margin of safety for each RCQ in the treatment of Plasmodium parasites.

Example 6

RCQs are not Readily Uptaken by CNS Neurotransmitter Transporters

Some known reversal agents, such as imipramine, have been reported to have neurological side effects. Although some side effects are acceptable (in quantity and/or quality) for a drug that otherwise effectively treats a disease of concern, such as malaria, this Example demonstrates that tested RCQs do not effectively compete with the natural ligands of the human serotonin (hSERT), dopamine (HEK-hDAT), and norepinephrine (hNET) transporters. Thus, such compounds are expected to have minimum impact on the in vivo function of such transporters and, correspondingly, few related side effects.

Selected RCQs were tested for inhibition of [$^3$H]neurotransmitter uptake by the recombinant human serotonin (hSERT), dopamine (HEK-hDAT), and norepinephrine (hNET) transporters by a modification of the method of Eshleman et al. (J. Pharmacol. Exp. Ther., 289(2):877-885, 1999). HEK-hDAT, hSERT, and -hNET expressing cells were grown on tissue culture dishes. After removing the medium and washing the plates with $Ca^{2+}$-, $Mg^{2+}$-free phosphate buffered saline (PBS), fresh medium was added and the plates were placed in a 25° C. water bath for 5 minutes. Cells were gently lifted from the plates and cell clusters separated by trituration. 50 μL aliquots of the suspended cells were added to assay tubes containing drugs and Krebs-HEPES assay buffer in a final volume of 0.5 mL.

Competition experiments were conducted in triplicate. After a 10 minute preincubation period at 25° C., [$^3$H] neurotransmitter (20 nM final concentration; [$^3$H]DA, [$^3$H] 5-HT, or [$^3$H]NE) were added, and the mixtures incubated for 10 minutes. Reactions were terminated by filtration through Wallac filtermat A filters (presoaked in 0.05% polyethylenimine), using a Tomtec cell harvester. Scintillation fluid was added to each filtered spot, and radioactivity remaining on the filters determined using a Wallac 1205 Betaplate scintillation counter.

Specific uptake was defined as the difference in uptake observed in the absence and presence of 5 μM mazindol (hDAT and hNET) or 5 μM imipramine (hSERT). Inhibition of uptake was determined by non-linear regression using Prism software.

TABLE 15

Inhibition of Neurotransmitter Uptake by Exemplary RCQs

| Molecule | Neurotransmitter Transporter Uptake (nM) | | |
|---|---|---|---|
|  | hSERT | HEK-hDAT | hNET |
| RCQ_02 | 230 | 2200 | 350 |
| RCQ_73 | 1160 | 1400 | 660 |
| RCQ_76 | 965 | 1080 | 550 |

$IC_{50}$ values for representative RCQs neurotransmitter transporter uptake are shown in the above table. These values are orders of magnitude higher than the $IC_{50}$ for these same compounds against even $CQ^R$ P. falciparum parasites (see Example 4). This indicates that significant neurological side effects may not be an issue for the disclosed RCQs, even those that have imipramine-like moieties.

Example 7

RCQs Clear Parasitemia In Vivo

This Example demonstrates the in vivo effectiveness of a representative RCQs in the treatment of Plasmodium sp. parasitemia.

A variation of the 4-day suppressive test described by Peters (Ann. Trop. Med. Parasitol., 69(2):155-171, 1975) was used to test the in vivo effectiveness of RCQ_02 as a treatment for Plasmodium sp. infection. Briefly, P. chabaudi parasites (Mackinnon and Read, Philos. Trans. R. Soc. Lond. B Biol. Sci., 359:965-986, 2004) were collected from a donor animal harboring approximately 20% parasitemia. Sixteen (16) male CF-1 mice at 4-5 weeks of age (approximately 20 g) were infected with approximately $10^7$ infected red blood cells via 100 μL tail vein injection. The infected mice were randomly sorted into groups of 4 mice each on day 0. One hour after infection, each group of four mice received 64, 32, 16, or 0 mg/kg RCQ_02 via oral gavage once per day for four days. After the treatment course, the animals were weighed and blood collected for the determination of parasite burden via direct microscopic analysis of Giemsa-stained blood smears.

Mice treated with 64 mg/kg RCQ_02 were all cleared of parasites to >99% by day 4. In addition, none of the treated mice showed any adverse side effects from RCQ_02 (e.g., weight loss, reduced eating, reduced activity, or ruffled ungroomed fur). This result was obtained even though RCQ_02 has relatively low water solubility; nonetheless, RCQ_02 was sufficiently orally available to produce a malaria cure in vivo without apparent adverse side effects.

While this disclosure has been described with an emphasis upon particular embodiments, it will be obvious to those of ordinary skill in the art that variations of the particular embodiments may be used and it is intended that the disclosure may be practiced otherwise than as specifically described herein. Accordingly, this disclosure includes all modifications encompassed within the spirit and scope of the disclosure as defined by the following claims.

We claim:

1. An antimalarial compound having the formula

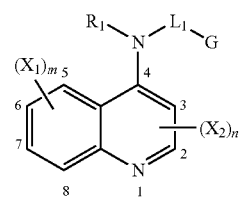

wherein $X_1$ and $X_2$ are independently halo, haloalkyl, amino, hydroxyl, alkoxy, alkylamino, or arylamino;

m is from 0 to 4;

n is from 0 to 2;

$R_1$ is H, alkyl, heteroalkyl, alkylamino, sulfonyl, haloalkyl, carbonyl, or alkylsulfonamide;

$L_1$ is from 1 to 12 atoms in length, and each position is independently methylene, difluoromethylene, dichloromethylene, —NH—, or —O—; and G is a $CQ^R$ reversal moiety having the structure

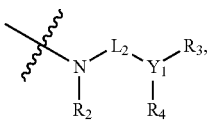

wherein $R_2$ is H, alkyl, heteroalkyl, alkylamino, haloalkyl, alkylsulfonamide, amide, alkylamide, cyano, cyanoalkyl, furyl, alkylfuran, or —$CONH_2$;
$L_2$ is from 1 to 12 atoms in length, and each position is independently methylene, difluoromethylene, dichloromethylene, —NH—, or —O—;
$Y_1$ is N, $NH^+$, CH, $CH_2CH$, or C(O)CH; and
$R_3$ and $R_4$ are independently cycloalkyl, heterocyclyl, aryl, heteroaryl, or

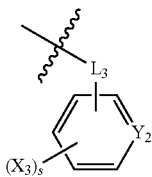

where each $X_3$ is independently H, halo, haloalkyl, amino, hydroxyl, alkylamino, cyano, alkoxy, sulfonamide, mercapto, or keto, s is 0 to 4, $Y_2$ is C$\underline{H}$, S or N, and $L_3$ is alkyl, methoxy, ethoxy, methylamino, ethylamino, —N—, —O—, or —S—, or $R_3$ and $R_4$ together with $Y_1$ form a tricyclic ring system having a formula selected from:

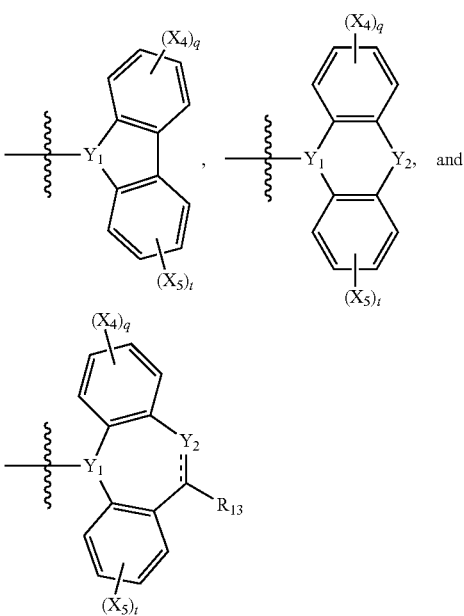

wherein $Y_2$ is N, O, CH, $CH_2$ or S;
$R_{13}$ is H, alkyl, heteroalkyl, =O, amino, amine, amide, sulfonamide, halo, cyano, hydroxy, mercapto, haloalkyl, alkoxy, alkylthio, thioalkoxy, arylalkyl, heteroaryl, alkylamino, dialkylamino, or alkylsulfano;
q and t are independently 0 to 4 as valence requirements permit;

each $X_4$ and $X_5$ independently is H, alkyl, halo, haloalkyl, alkoxy, amino, hydroxyl, alkylamino, cyano, or mercapto; and
each peripheral ring can independently include at least one heteroatom at any position that valence requirements permit.

2. The compound of claim 1, wherein $Y_1$ is N.
3. The compound of claim 1, wherein $L_2$ is from 2 to 6 atoms in length.
4. The compound of claim 1, wherein m is 1 or 2, n is 0 or 1, and each $X_1$ and $X_2$ independently is H, chloro, fluoro, or trifluoromethyl.
5. The compound of claim 1, wherein each $X_1$ independently is H, chloro, or trifluoromethyl, and n is 0.
6. The compound of claim 5, wherein m is 1 and $(X_1)_m$ is chloro at position $C_7$.
7. The compound of claim 1, wherein $R_1$ and $R_2$ are independently H, alkyl having from 1 to 4 carbon atoms, or heteroalkyl having from 1 to 4 carbon atoms.
8. The compound of claim 7, wherein $R_1$ and $R_2$ are independently H, methyl, trifluoromethyl, —$CH_2CH_2CF_3$, —$CH_2CF_3$, —$CH_2CH_2NH_2$, —$CH_2NH_2$, —$CH_2CH_2C(O)NH_2$, or —$CH_2C(O)NH_2$.
9. The compound of claim 1, wherein:
m is 1 and $(X_1)_m$ is chloro at position $C_7$;
n is 0; and
$R_1$ and $R_2$ are independently H, methyl, trifluoromethyl, —$CH_2CH_2CF_3$, —$CH_2CF_3$, —$CH_2CH_2NH_2$, —$CH_2NH_2$, —$CH_2CH_2C(O)NH_2$, or —$CH_2C(O)NH_2$.
10. The compound of claim 1, wherein:
$R_1$ and $R_2$ are independently H, alkyl, or heteroalkyl;
$Y_1$ is CH or N; and
$R_3$ and $R_4$ are independently aryl, or heteroaryl, or together with $Y_1$ form a tricyclic ring system.
11. The compound of claim 1, wherein:
$R_1$ and $R_2$ are independently H, alkyl, or heteroalkyl;
$Y_1$ is CH or N; and
$R_3$ and $R_4$ independently have the formula:

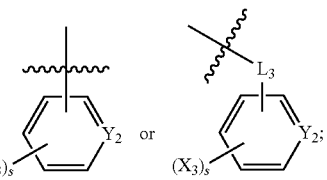

where each $X_3$ independently is H, halo, haloalkyl, amino, hydroxyl, alkylamino, cyano, alkoxy, sulfonamide, mercapto, or keto, s is 0 to 4, and $Y_2$ is CH or N.
12. The compound of claim 11, wherein:
$R_1$ is H;
s is 1;
$X_3$ is H, fluoro, chloro, trifluoromethyl, or hydroxyl; and
$L_3$ is methyl or ethyl.
13. The compound of claim 11, wherein $Y_2$ is nitrogen.
14. The compound of claim 11, wherein $L_3$ is methyl, ethyl, methoxy, ethoxy, methylamino, ethylamino, —N—, or —O—.
15. The compound of claim 11, wherein:
s is 1 or 2;
each $X_3$ independently is H, fluoro, chloro, trifluoromethyl, methoxy, mercapto, or keto;
$Y_2$ is nitrogen; and
$L_3$ is methyl, ethyl, methoxy, ethoxy, methylamino, ethylamino, —N—, or —O—.

16. The compound of claim 11, wherein $R_3$ and $R_4$ are the same.

17. The compound of claim 11, wherein $R_3$ and $R_4$ are different.

18. The compound of claim 1, having the formula

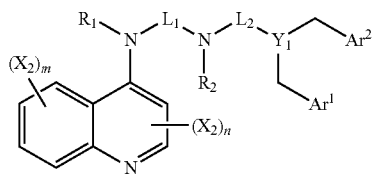

wherein $Ar^1$ and $Ar^2$ are independently selected aryl groups.

19. The compound of claim 18, having the formula

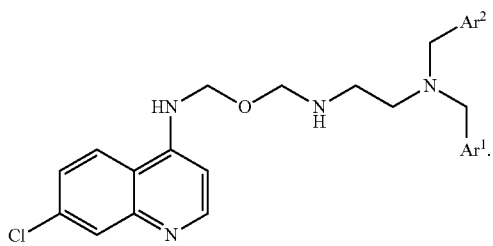

20. The compound of claim 18, having the formula

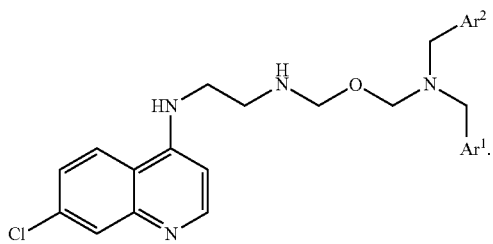

21. The compound of claim 1, wherein $R_3$ and $R_4$ together with $Y_1$ form a tricyclic ring system wherein:

q and t are independently 0 to 2;

each $X_4$ and $X_5$ independently is H, methyl, fluoro, chloro, trifluoromethyl, methoxy, or cyano;

$Y_2$ is N or S; and $R_{13}$ is H or =O.

22. The compound of claim 1, wherein $R_3$ and $R_4$ together with $Y_1$ form a tricyclic ring system wherein:

$Y_1$ is nitrogen;

$Y_2$ is CH, CH$_2$ or S;

$R_{13}$ is H or =O;

q and t are independently 0 to 2; and each $X_4$ and $X_5$ independently is H, fluoro, chloro, trifluoromethyl, cyano, or alkoxy.

23. A compound, having a formula selected from

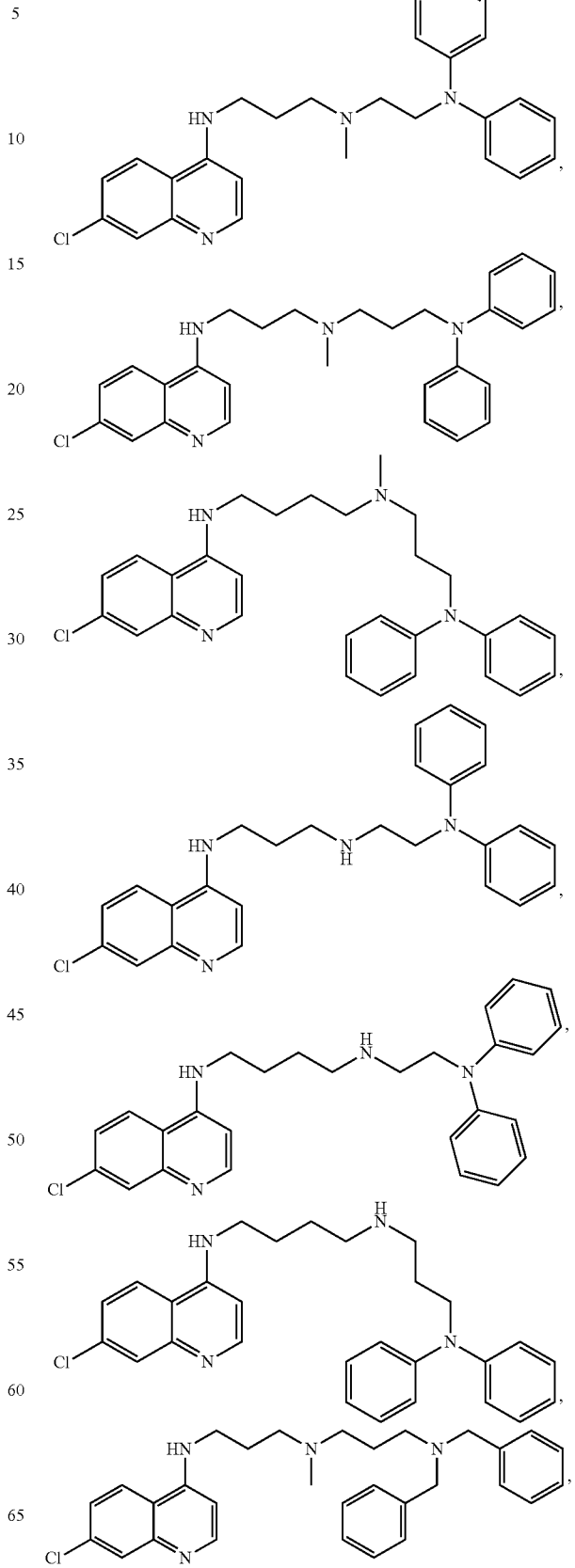

99
-continued
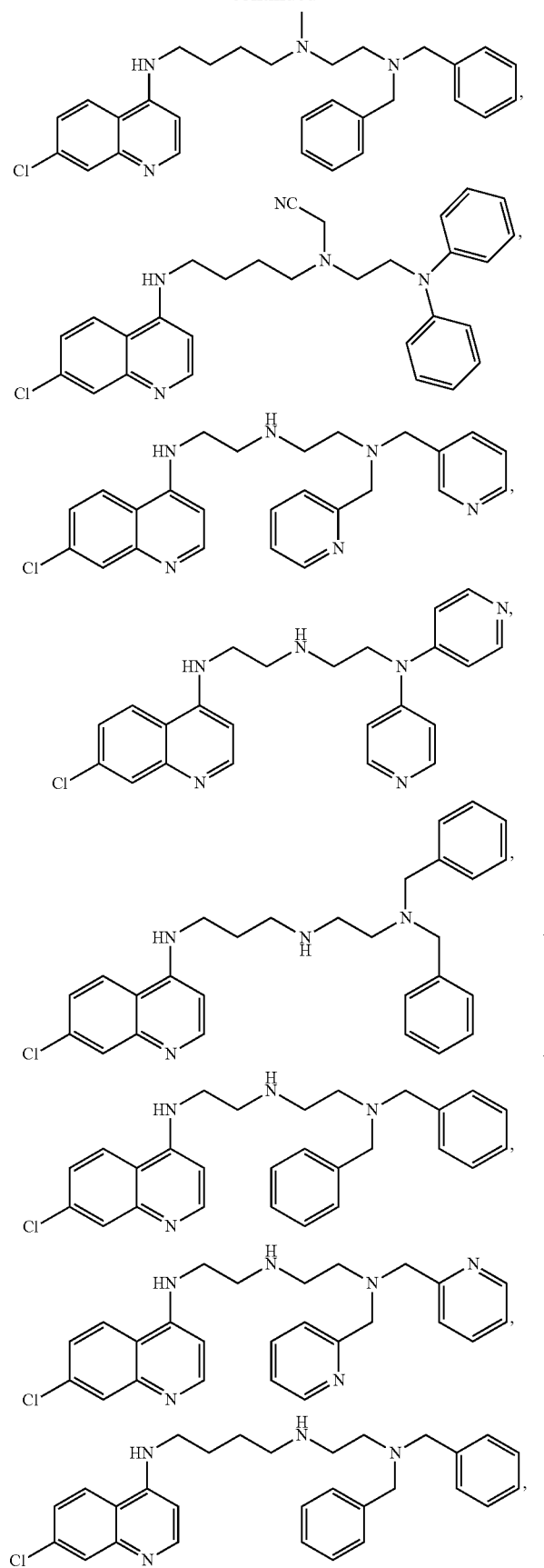
100
-continued
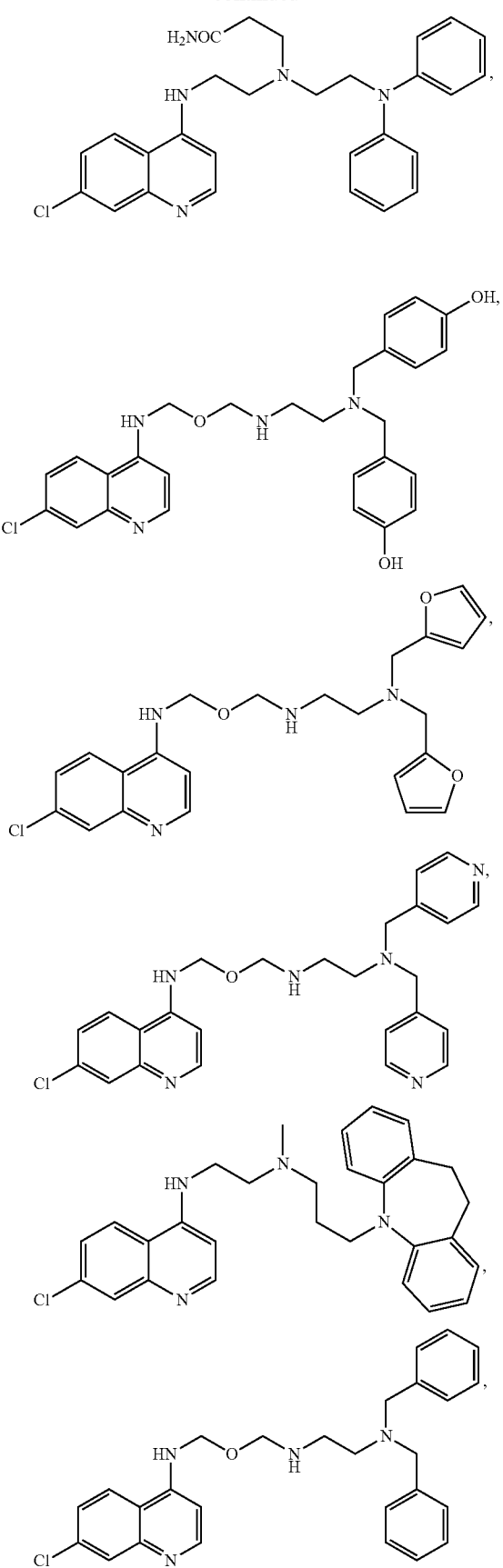

101
-continued
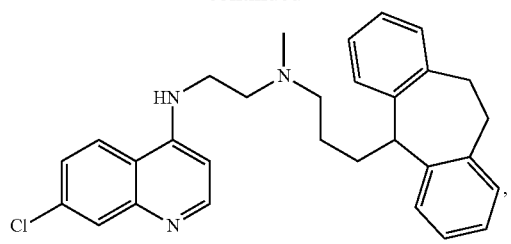
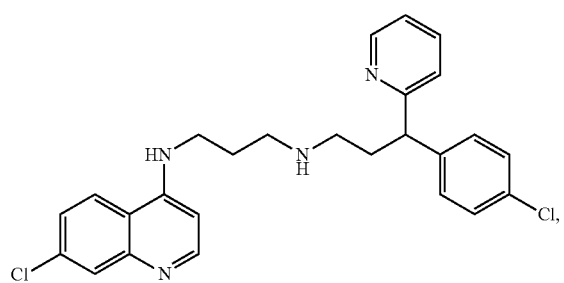
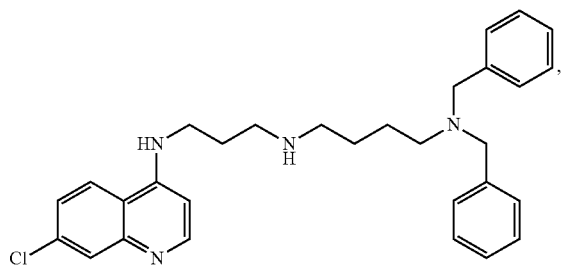
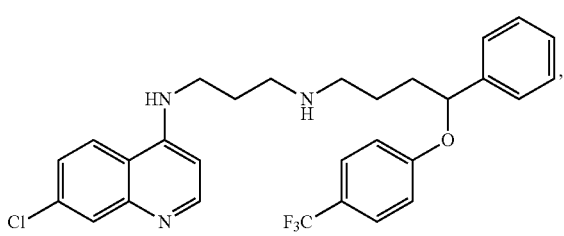
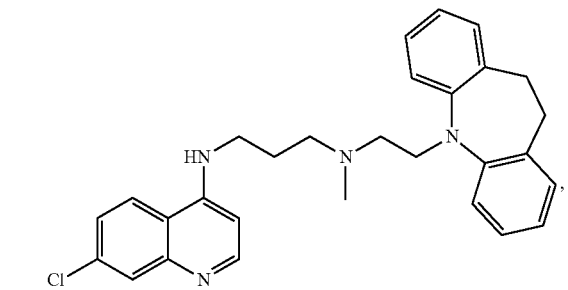
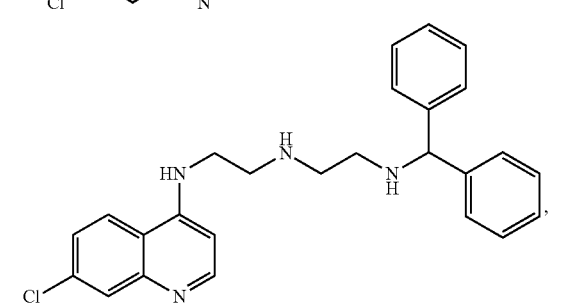
102
-continued
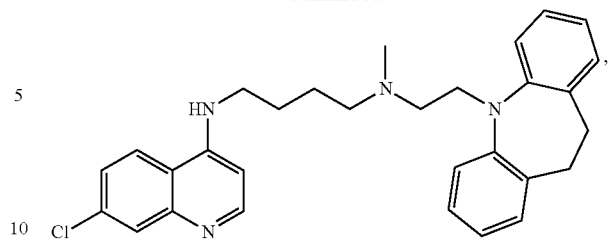
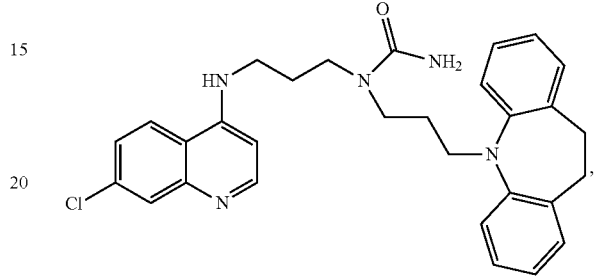
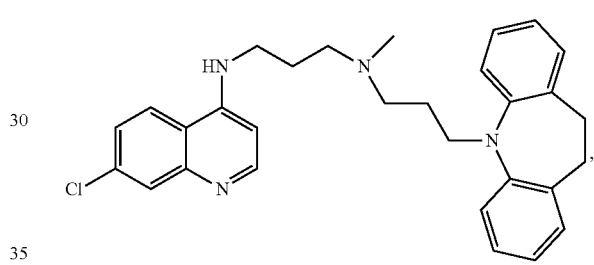
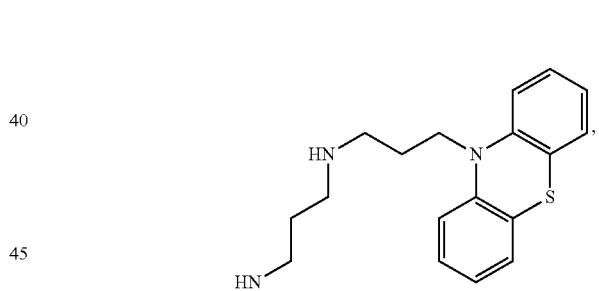
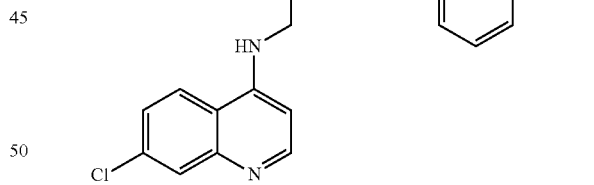
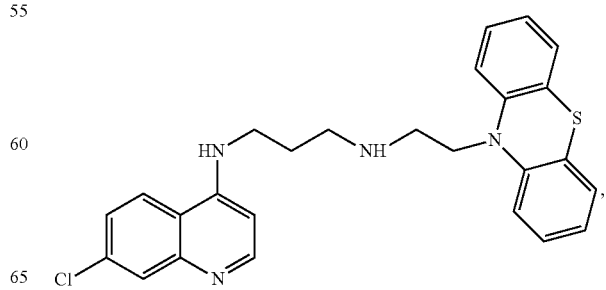

-continued

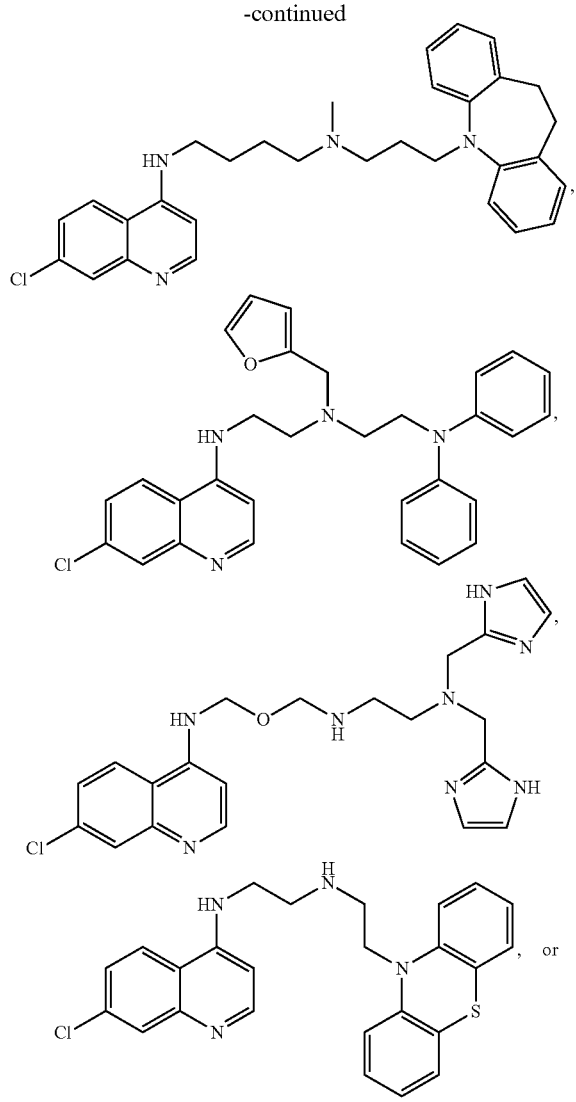

-continued

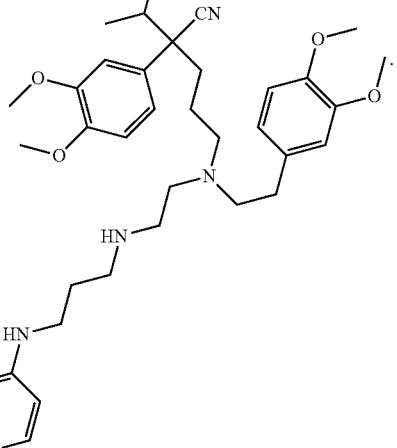

24. A pharmaceutical composition, the composition comprising a therapeutically effective amount of the compound of claim 1 and a pharmaceutically acceptable carrier.

25. The pharmaceutical composition of claim 24, further comprising at least one additional medicinal or pharmaceutical agent.

26. The pharmaceutical composition of claim 25, wherein the additional medicinal or pharmaceutical agent is an antimalarial therapeutic agent.

27. The pharmaceutical composition of claim 25, wherein the at least one additional medicinal or pharmaceutical agent is selected from the group consisting of artesunate, mefloquine, sulfadoxine, pyrimethamine, and combinations thereof.

28. A pharmaceutical composition, the composition comprising a therapeutically effective amount of the compound of claim 23 and a pharmaceutically acceptable carrier.

29. The pharmaceutical composition of claim 28, further comprising at least one additional medicinal or pharmaceutical agent.

* * * * *